United States Patent
Giannakakou et al.

(10) Patent No.: US 9,671,405 B2
(45) Date of Patent: Jun. 6, 2017

(54) IDENTIFYING TAXANE SENSITIVITY IN PROSTATE CANCER PATIENTS

(71) Applicants: Cornell University, Ithaca, NY (US); University of Washington, Seattle, WA (US)

(72) Inventors: Paraskevi Giannakakou, Tenafly, NJ (US); Stephen R. Plymate, Seattle, WA (US)

(73) Assignees: Cornell University, Ithaca, NY (US); University of Washington, Seattle, WA (US)

( * ) Notice: Subject to any disclaimer, the term of this patent is extended or adjusted under 35 U.S.C. 154(b) by 0 days.

(21) Appl. No.: 14/429,657

(22) PCT Filed: Sep. 19, 2013

(86) PCT No.: PCT/US2013/060616
§ 371 (c)(1),
(2) Date: Mar. 19, 2015

(87) PCT Pub. No.: WO2014/047285
PCT Pub. Date: Mar. 27, 2014

(65) Prior Publication Data
US 2015/0233927 A1 Aug. 20, 2015

Related U.S. Application Data

(60) Provisional application No. 61/702,983, filed on Sep. 19, 2012.

(51) Int. Cl.
*A61K 31/337* (2006.01)
*C12Q 1/68* (2006.01)
*G01N 33/574* (2006.01)

(52) U.S. Cl.
CPC ..... *G01N 33/57434* (2013.01); *A61K 31/337* (2013.01); *C12Q 1/6886* (2013.01); *G01N 33/57492* (2013.01); *C12Q 2600/106* (2013.01); *C12Q 2600/158* (2013.01); *G01N 2333/723* (2013.01)

(58) Field of Classification Search
None
See application file for complete search history.

(56) References Cited

U.S. PATENT DOCUMENTS

2010/0068802 A1  3/2010  Qiu et al.

FOREIGN PATENT DOCUMENTS

| WO | WO-2005020794 A2 | 3/2005 |
| WO | WO-2009128936 A2 | 10/2009 |
| WO | WO-2014047285 A1 | 3/2014 |

OTHER PUBLICATIONS

Tannock et al. (N. Engl. J. Med. Oct. 7, 2004).*
Sun et al. (J. Clinical Investigation Aug. 2010 120(8): 2715-2730).*
Sung et al. (Cancer Res. Apr. 15, 2012 72(8): Suppl.1 Ab No. 3634).*
Portella et al. (Cancer Research Apr. 15, 2013, 73(8) Ab. No. 4081).*
"International Application U.S. Appl. No. PCT/US2013/060616, International Search Report mailed Dec. 11, 2013", 7 pgs.
"International Application U.S. Appl. No. PCT/US2013/060616, Written Opinion mailed Dec. 11, 2013", 7 pgs.
Dehm, S. M, et al., "Alternatively spliced androgen receptor variants", Endocrine Related Cancer, vol. 18, No. 5, (Jul. 21, 2011), R183-R196.
Ericca, Pratt D, et al., "Rare cell capture in microfluidic devices", Chemical Engineering Science, Oxford, GB vol. 66, No. 7, (Sep. 8, 2010), 1508-1522.
Gang, Liu, et al., "AR Variant AR v567es Induces Carcinogenesis in a Novel Transgenic Mouse Model of Prostate Cancer 1,2", Neoplasia, (Jan. 1, 2013), 1009-1017.
Jason, Gleghorn, et al., "Capture of circulating tumor cells from whole blood of prostate cancer patients using geometrically enhanced differential immunocapture (GEDI) and a prostate-specific antibody", Lab on a Chip, vol. 10, No. 1 (Jan. 1, 2010), 27 pgs.
Nagalaxmi, Nadiminty, et al., "Mechanisms of persistent activation of the androgen receptor in CRPC: recent advances and future perspectives", World Journal of Urology, Springer, Berlin, DE, vol. 30, No. 3, (Oct. 19, 2011), 287-295.
"International Application U.S. Appl. No. PCT/US2013/060616, International Preliminary Report on Patentability mailed Apr. 2, 2015", 9 pgs.

* cited by examiner

*Primary Examiner* — Peter J Reddig
(74) *Attorney, Agent, or Firm* — Schwegman Lundberg & Woessner, P.A.

(57) ABSTRACT

The invention relates to detection and/or treatment of a subset of prostate cancer patients who may benefit from taxane treatment. The method comprises testing whether an androgen receptor (AR) splice variant is present in a test sample obtained from the patient, wherein the androgen receptor variant can be ARv5,6,7.

7 Claims, 30 Drawing Sheets

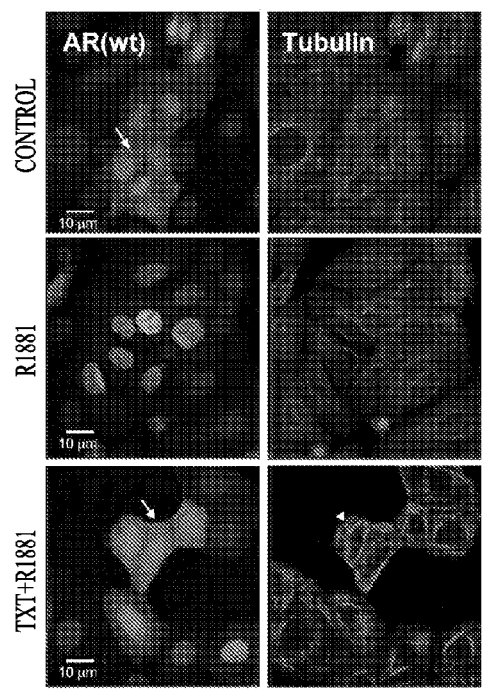
*FIG. 9A*
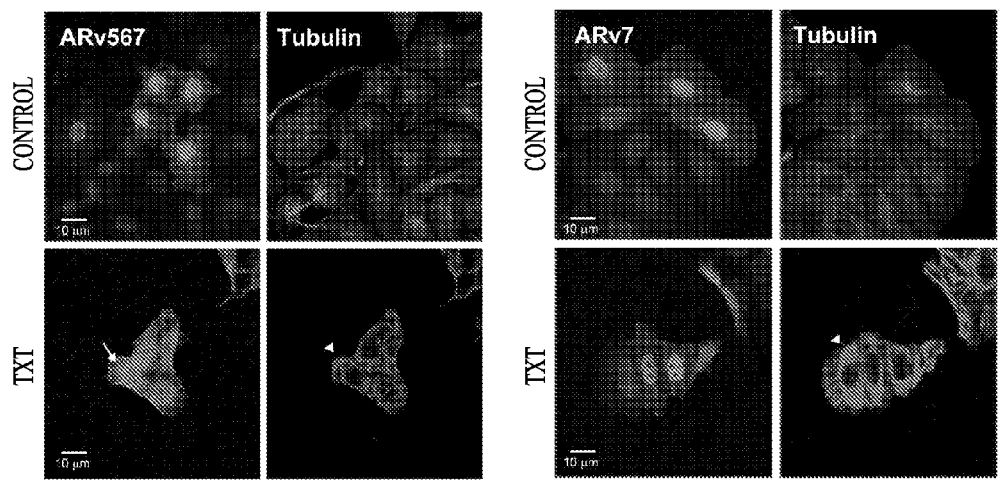
*FIG. 9B*  *FIG. 9C*

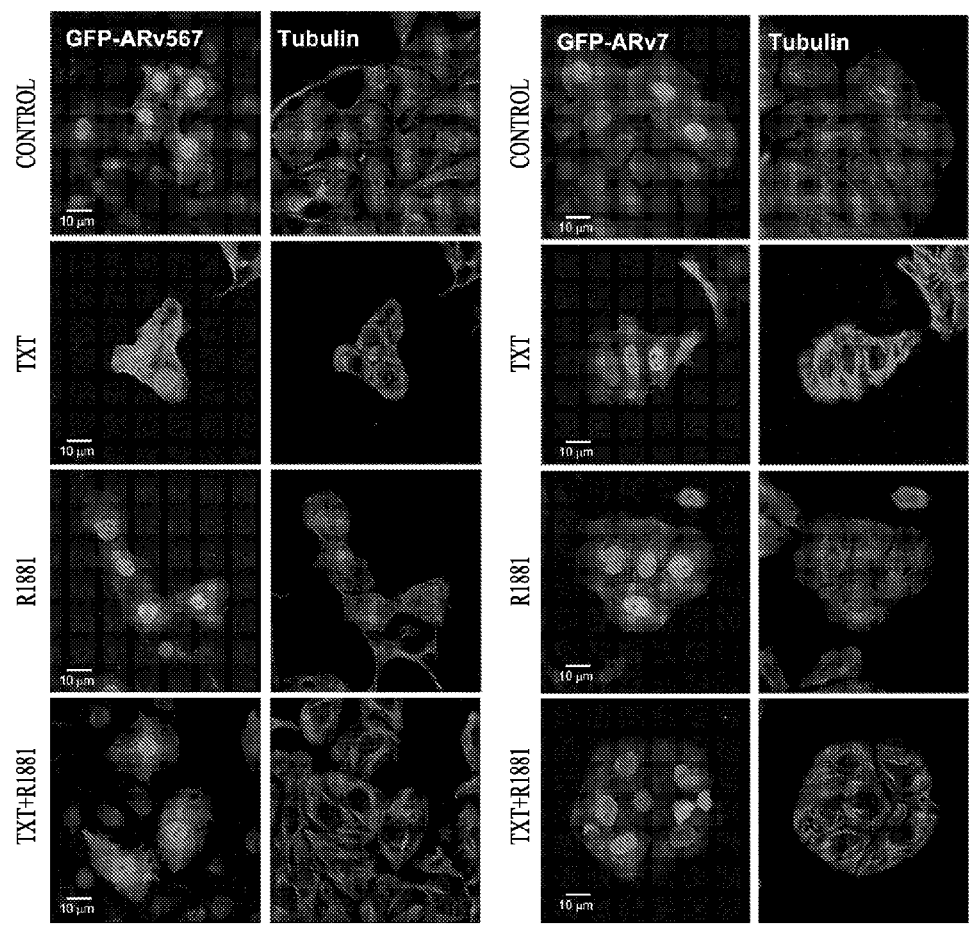
*FIG. 9I*  *FIG. 9J*

US 9,671,405 B2

IDENTIFYING TAXANE SENSITIVITY IN PROSTATE CANCER PATIENTS

CROSS-REFERENCE TO RELATED APPLICATION

This patent application is a national stage application under 35 U.S.C. §371 of PCT/US2013/060616, filed Sep. 19, 2013, and published as WO 2014/047285 A1 on Mar. 27, 2014, which claims the benefit of priority, under 35 U.S.C. Section §119(e), to U.S. Provisional Patent Application Ser. No. 61/702,983 filed on Sep. 19, 2012, which applications and publication are incorporated by reference as if reproduced herein and made a part hereof in their entirety, and the benefit of priority of each of which is claimed herein.

GOVERNMENT SUPPORT

This invention was made with government support under P50 CA 097186, PO1 CA163227, PO1 CA085859, and R01 CA137020-01 awarded by the National Institutes of Health; and under PC121152 awarded by the Defense Advanced Research Projects Agency. The government has certain rights in the invention.

SEQUENCE LISTING

This document incorporates by reference herein an electronic sequence listing text file, which is filed in electronic format via EFS-Web. The text file is named "143559.txt," is 32,090 bytes, and was created on Mar. 19, 2015.

BACKGROUND

Androgen ablation therapy is the mainstay for prostate cancer (PC) treatment. However, it is not curative, as many patients progress to a castration-resistant stage of prostate cancer (CRPC). In fact, prostate cancer progression is dependent on continuous androgen receptor (AR) signaling and transcriptional activity. Thus, strategies designed to effectively inhibit androgen receptor transcriptional activity and signaling, are at the forefront of current research in prostate cancer. The importance of the androgen receptor in prostate cancer disease progression is highlighted by the fact that many recent therapies are designed to target the androgen axis, such as the androgen receptor antagonist enzalutamide (formerly MDV3100) (see, e.g., Hoffman-Censits & Kelly, *Clin Cancer Res* 19, 1335 (Mar. 15, 2013); Tran et al., *Science* 324, 787 (May 8, 2009)), and the CYP17 inhibitor abiraterone (Bono et al., *N Engl J Med* 364, 1995 (May 26, 2011)), which inhibits androgen synthesis. However, resistance to all forms of androgen deprivation therapy, including these next-generation compounds, occurs eventually and results in disease progression. Despite androgen ablation, castration-resistant prostate cancer (CRPC) remains androgen receptor driven due to several mechanisms including androgen receptor gene amplification, in situ androgen production and the presence of ligand-independent AR splice variants which localize to the nucleus and are constitutively active (Nelson, *J Clin Oncol* 30, 644 (Feb. 20, 2012); Locke et al., *Cancer Res* 68, 6407 (Aug. 1, 2008); Chen et al., *Nat Med* 10, 33 (January, 2004); Nadiminty & Gao, *World J Urol* 30, 287 (June, 2012)).

A major challenge in the clinical management of castration-resistant prostate cancer is that currently there is no biomarker that predicts clinical efficacy of chemotherapy. The taxanes represent the only class of cancer chemotherapeutics demonstrated to prolong survival in castration-resistant prostate cancer. Despite the clinical success of taxanes, treatment efficacy can be transient and the development of clinical taxane resistance is the major cause of cancer-related death. An important clinical question remains as to why patients who fail treatment with one taxane respond to another, and how clinicians can anticipate progression and proactively switch treatment.

New methods for detecting what type of therapeutic intervention is appropriate for a particular patient are needed.

SUMMARY OF THE INVENTION

As described herein, two androgen receptor splice variants ARv5,6,7 and AR-v7 can be used as markers for identifying prostate cancer patients who will, or will not, respond to taxane chemotherapy. In particular, as described herein, expression of androgen receptor splice variant v5,6,7 correlates with taxane sensitivity to patients in vivo while expression of androgen receptor splice variant v7 is associated with drug resistance. The variants are constitutively active in the nucleus of various prostate cancer types, rise in response to castration, and can mediate disease progression in castration-resistant prostate cancer. The choice of which drug(s) to administer to a prostate cancer patient can therefore be resolved by detection of one or the other androgen receptor slice variants in patient samples.

The invention therefore relates to a method of determining whether a prostate cancer patient can benefit from taxane drug treatment that involves testing whether an androgen receptor splice selected from the group consisting of variant v5,6,7, variant v7, or a combination thereof is present in a test sample obtained from the patient. For example, the prostate cancer patient can benefit from taxane drug treatment when more androgen receptor splice variant v5,6,7 is present in a test sample than variant v7. However, a prostate cancer patient may not benefit from taxane drug treatment when more androgen receptor splice variant v7 is present in a test sample than variant v5,6,7. The method can include testing samples such as circulating tumor cells, prostate tissue samples, blood samples, serum samples, ascites fluid samples, urine samples, semen samples, or a combination thereof. The method can also include capturing circulating tumor cells from the test sample before the testing, for example, by using a microfluidic device such as the device described herein.

Testing can involve an immunoassay, cell sorting assay, sandwich immunoassay, competition inhibition immunoassay, ELISA (Enzyme-Linked Immunosorbent Assay), immunohistochemical assay, agglutination assay, precipitation assay, radioimmunoassay or antigen-down immunoassay, immunometric assay, competitive binding assay, a direct sandwich immunoassay, an indirect sandwich assay, an immunoprecipitation assay, a nuclear immunostaining assay, an immunoblot assay, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, in situ hybridization, nucleic acid amplification, reverse transcription, polymerase chain reaction, quantitative real time polymerase chain reaction (qRT-PCR), or a combination thereof.

In some embodiments, at least one probe or primer that specifically binds to an mRNA encoding the androgen receptor splice variant v5,6,7 can be used to detect and/or quantify mRNA expression levels of the androgen receptor splice variant v5,6,7. Alternatively, or in addition, at least one probe or primer that specifically binds to an mRNA encoding the androgen receptor splice variant v7 can be used to detect and/or quantify mRNA expression levels of the androgen receptor splice variant v7.

In other embodiments, an antibody specific for the androgen receptor splice variant v5,6,7 can be used in an immunological assay to detect whether the androgen receptor splice variant v5,6,7 is present in the patient's test sample. Alternatively, or in addition, an antibody specific for the androgen receptor splice variant v7 can be used in an immunological assay to detect whether the androgen receptor splice variant v7 is present in the patient's test sample.

Another aspect of the invention is a method of identifying whether a prostate cancer patient will benefit from taxane drug treatment comprising determining whether an androgen receptor splice variant v5,6,7 is expressed in a test sample from the patient, and identifying a patient who will benefit from taxane drug treatment when the androgen receptor splice variant v5,6,7 is expressed in the test sample.

In some embodiments, the methods further include administering a taxane drug to a patient when the androgen receptor splice variant v5,6,7 is expressed in the test sample obtained from that patient.

Another aspect of the invention is a device for detecting androgen receptor splice variant v5,6,7 or androgen receptor splice variant v7 in a test sample, comprising a solid surface and an antibody specific for the androgen receptor splice variant (e.g., either or both of the v5,6,7 or v7 variants). The antibody can be immobilized onto the solid surface. The device can be configured for flow of a test sample through the device and binding of androgen receptor splice variant v5,6,7 to the antibody specific for the androgen receptor splice variant v5,6,7. In some embodiments, the device can be configured for flow of a test sample through the device and capture of cells that express androgen receptor splice variant v5,6,7, for example, by binding such cells to antibodies specific for the androgen receptor splice variant v5,6,7.

The test sample can be a bodily fluid sample or a tissue sample from a patient. Such a fluid sample can be blood, serum, plasma, semen, urine, lymph, or a combination thereof. The tissue sample can be a biopsy tissue sample, for example, a sample of prostate tissue.

In some embodiments, the patient is a healthy patient being tested for a susceptibility to prostate cancer. In other embodiments, the patient is a patient with prostate cancer and the method is used to evaluate the progression of the cancer and whether treatment with a taxane drug would be beneficial.

DESCRIPTION OF THE FIGURES

FIG. 1A shows schematic of the GEDI device illustrating blood flow through device. FIG. 1B shows a schematic of a device that can have a gasket, a inlet and an outlet. FIG. 1C illustrates a surface functionalization scheme that can be used to attach a binding entity such as a J591 monoclonal anti-PMSA antibody to a solid surface of the device. FIG. 1D illustrates the cell capture performance of the device as a function of shear stress and antibody concentration. Titration curves for the anti-PSMA J591 antibody in a standardized geometry indicate optimal antibody concentration for cell capture.

FIG. 2A schematically illustrates flow through a microfluidic obstacle array with array geometric parameters. $\Delta$=obstacle offset. $\Lambda$=obstacle spacing in the direction of bulk flow. $\Gamma$=obstacle spacing in the direction orthogonal to bulk flow. $2r$=obstacle diameter. Flow is from left to right. Path lines denote trajectories of cells of different diameters. Obstacle array spacing and orientation parameters are also defined. FIG. 2B graphically illustrates that the rate of cell-wall collisions for cells traveling through the array is a strong function of the offset parameter of the array; the GEDI design methodology indicates what offset parameter leads to size-dependent collision rates. The results predicted for the flow through geometry illustrated in FIG. 2A are shown as a solid line in FIG. 2B. The four specific cell sizes lead to results denoted by the labeled dots in FIG. 2B. Other geometric arrangements of posts within the device lead to different results, shown at right in the dotted and dashed lines. FIG. 2C graphically illustrates the capture efficiency of straight arrays or arrays with small offsets ("Straight") is lower that the capture efficiency of the GEDI device described herein. FIG. 2D illustrates that straight arrays or arrays with small offsets exhibit size independent collision rates (boxed in area to by the origin of the graph). Carefully chosen offsets such as those provided in the GEDI device exhibit size dependent collision rates (boxed in area from about offset 6 to 12 µm). Capture rates shown in FIG. 2C-2D compare GEDI (7-µm offset) and straight (no offset) geometry performance as measured by LNCaP capture efficiency on J591-functionalized devices. Rates shown in the FIG. 2D describe simulated collision rates in these geometries. Both experimental results have the same surface-area-to-volume ratio. FIG. 2E schematically illustrates the offset array of the GEDI device versus a straight array. FIG. 2F graphically illustrates the average collision frequency of the GEDI device versus a device with a straight flow path. Devices with the same surface area to volume ratio give vastly different results: straight arrays lead to collisions that decrease as the blood travels through the device; GEDI arrays lead to collisions that increase with travel through the device.

FIG. 3A shows representative images of circulating tumor cells captured with the GEDI device from 1 mL of blood from prostate cancer patients. Circulating tumor cells are imaged on the device and are identified following immunostaining with DAPI, PSMA, CD45, and EpCAM. Intact, nucleated cells that are PSMA$^+$/CD45$^-$ are identified as circulating tumor cells. Leucocytes are identified as DAPI$^+$/PSMA$^-$/CD45$^+$ (bottom row, arrow). Note the heterogeneity of EpCAM expression in the PSMA$^+$ cell population (top and bottom rows, EpCAM−; middle row, EpCAM$^+$). Scale bar: 10 µm. FIG. 2B graphically illustrates disease-specific GEDI capture of circulating tumor cells. Circulating tumor cell enumeration (CTCs/ml) was performed using blood from healthy donors (median=3) and castration-resistant prostate cancer patients (median=54). ($p<0.001$; Wilcoxon) FIG. 3C graphically compares the circulating tumor cells per ml as enumerated by GEDI-based- and CellSearch®-based capture devices. This comparison was performed using same-day blood draws from 25 individual castration-resistant prostate cancer patients. * indicates that CellSearch-based enumeration was performed 1 week before the GEDI-based enumeration; ∉ indicates the same patient whose blood was drawn on two separate time points three months apart (blood draw no 14 occurred 3 months after blood draw no 19); # indicates the same patient whose blood was drawn on two separate time points 1 year apart (blood draw no 22 occurred 1 year before blood draw no 23). FIG. 3D graphically illustrates the effectiveness of the GEDI device versus the CellSearch® device. The graph shows a correlation between the numbers of circulating tumor cells detected by the CellSearch® system vs. the GEDI system from same day blood draws. A correlation coefficient of r=0.44 (outliers were removed with Cook's distance restriction) was determined. Hashtag and asterisk denote two pairs of data each taken on the same patient at two longitudinal time points. r is not changed significantly by inclusion or rejection of these points.

FIG. 4A shows that the population of captured cells is highly pure, enabling the identification of single point mutations in the genomes of cells within the population. The T868A (ACT-GCT; Thr-Ala) androgen receptor single-point mutation is detected from RNA extracted from fifty C4-2 cells spiked into 1 ml of healthy-donor blood and captured by the GEDI device (third row, arrow, sequence CATCAGTTC GCTTTTGACCT, SEQ ID NO:7). Sequencing results from 1 ml blood from the same healthy donor (top row; sequence CATCAGTTCACTTTTGACCT, SEQ ID NO:8) or from fifty C4-2 cells in culture (middle row; sequence CATCA-GTTCGCTTTTGACCT, SEQ ID NO:9) are also depicted. FIG. 4B illustrates that the TMPRSS2:ERG fusion protein is detected in GEDI-captured circulating tumor cells from a castration-resistant prostate cancer patient. PSMA-captured circulating tumor cells were stained on the device with an anti-ERG antibody. Representative examples of three PSMA$^+$/CD45$^-$ circulating tumor cells are shown, two of which are positive for ERG. Scale bars: 10 microns. FIG. 4C-4E illustrate TMPRSS2:ERG detection by immunofluorescence on GEDI-captured cells. FIG. 4C illustrates ERG antibody staining of TMPRSS2:ERG fusion-positive (vCaP) and fusion-negative (C4-2) prostate cancer cell lines. Representative images acquired by confocal microscopy are displayed. Note the nuclear ERG staining in fusion-positive vCaP cells. FIG. 4D shows immunostained cells captured by the GEDI device. Two hundred vCaP cells were spiked in 1 ml of healthy-donor blood, flown through the GEDI device and processed for ERG immunofluorescence labeling. Nuclear ERG staining was detected in the GEDI-captured vCaP cells, identified as PSMA$^+$/DAPI$^+$/CD45$^-$ cells. FIG. 4E shows a representative example of ERG-negative/CD45$^+$ leucocytes identified in the blood from a castration-resistant prostate cancer patient processed by the GEDI device as in FIG. 4B.

FIG. 5A shows images of C4-2 prostate cancer cells that were spiked (at 200 cells/ml) into a healthy-donor whole blood sample and then captured by the GEDI device. One ml of spiked blood was then passed through each of three GEDI devices. Captured cells were incubated on each device at 37° C. for 24 hr with either DMSO control (upper panel) or 100 nM docetaxel (DTX; middle panel) or 1 µM docetaxel (lower panel). Following drug treatment, cells were fixed and processed for immunofluorescence staining using antibodies against tubulin and CD45. DAPI was used as a DNA counterstain to evaluate nuclear integrity. Note the fine and intricate microtubule network in the DMSO control (top panel) and the distinct microtubule bundles in the docetaxel treated devices (arrows, middle and bottom panels). Apoptotic nuclei were observed at higher docetaxel concentrations (arrowhead, bottom panel). FIG. 5B shows images of GEDI-captured circulating tumor cells obtained from the blood of a castration-resistant prostate cancer patient after the cells were treated ex-vivo on the GEDI device with 100 nM docetaxel (top panel) or 100 nM paclitaxel (PTX; bottom panel) at 37° C. for 24 hr. Following drug treatment, the PSMA-captured cells were fixed and processed for immunofluorescence staining as in FIG. 5A with the addition of cytokeratin-18 as an alternative epithelial marker. In this patient, the presence of an unperturbed microtubule network following docetaxel treatment (FIG. 5B, top panels) indicates lack of efficient drug-target engagement. In contrast, addition of paclitaxel resulted in microtubule bundling (FIG. 5B, bottom panels). FIG. 5C-5E illustrate additional examples of on-chip assessment of effective drug-target engagement from different castration-resistant prostate cancer patients: taxane-induced microtubule bundling and mitotic defects as evidence of drug-target engagement in GEDI-captured CTCs. FIG. 5C shows GEDI-captured circulating tumor cells from the same patient as in FIG. 5B, after paclitaxel-induced prometaphase arrest of the GEDI-captured circulating tumor cells. These data provide additional evidence of effective drug-target engagement in the GEDI-captured cells. FIG. 5D shows that GEDI-captured circulating tumor cells from a patient (patient 3) following ex-vivo on-chip treatment with 100 nM DTX do not exhibit any evidence of a microtubule response (bundling) to drug treatment. FIG. 5E shows that GEDI-captured circulating tumor cells from a patient (patient 2) display microtubule bundling (arrow) following ex-vivo on-chip treatment with 100 nM or 1 uM paclitaxel (PTX). FIG. 5F shows GEDI-captured circulating tumor cells from a patient (patient 4) following ex-vivo on-chip treatment with 50 nM paclitaxel (PTX) exhibit a heterogeneous response to drug treatment. Note the distinct microtubule bundling in the PSMA$^+$ cells (middle panel, barbed arrow) and no detectable microtubule network in another PSMA$^+$ cells from the same patient (bottom panel, standard arrow). The adjacent leucocyte (PSMA$^-$) shows clear microtubule bundling in response to paclitaxel (PTX) treatment.

FIG. 6A shows schematic diagrams of a full-length human androgen receptor, of the N-terminal domain of the human androgen receptor, and of the C-terminal domain of the human androgen receptor used in experiments described herein. The numbers (positions) of amino acids are shown below the diagrams. FIG. 6C shows schematic diagrams of a full-length human androgen receptor, and a series of C-terminal androgen receptor fragments. FIGS. 6B and 6D show electrophoretically separated products of microtubule co-sedimentation assays of PC3:mCh-tub cells that transiently express GFP-AR(wt), GFP-N-terminal AR (N-ter AR) or GFP-C-terminal AR (C-ter AR) or each of the smaller deletion mutants as indicated. Following high-speed centrifugation equal volumes from each fraction (WP and WS) were resolved by SDS-PAGE and immunoblotted as indicated. WP: warm pellet containing microtubule polymers and associated proteins, WS: warm supernatant containing soluble tubulin dimers and proteins non-associated with microtubules. Boxes highlight the relative protein distribution between the WP and WS fractions from each condition. The percent protein present in the pellet fraction (% WP) was calculated using the following formula: % P=100*WP/(WP+WS) and is presented to the right of each immunoblot. For tubulin a range of values is shown in the % WP quantitation reflecting each of the three reactions performed. FIG. 6E shows electrophoretically separated products of microtubule co-sedimentation assays of the HEK293 cell line, showing the same results as shown in FIGS. 6B and 6D, namely that the C-terminal region of the androgen receptor mediates microtubule binding. The data shown in FIG. 6E was generated using HEK293 cells that were transiently transfected with full-length GFP-AR (wt), GFP-N-ter AR or GFP-C-ter AR and subjected to microtubule co-sedimentation as described earlier. Proteins from each respective fraction were resolved on SDS-PAGE and immunoblotted with the indicated antibodies. Wild-type and C-terminus-AR co-fractionated with the microtubule pellets (WP) whereas N-terminus AR remained in the WS, consistent with the results seen in the PC3:mCh-tub cells. Tubulin was detected in as microtubules in the WP in each condition.

FIG. 7A is a schematic diagram of the full-length androgen receptor as well as the splice variants ARv5,6,7, encoding exons 1-4 and the first 10 amino acids of exon 8, and ARv7, encoding exons 1-3 and a cryptic exon of 16 amino acids. FIGS. 7B and 7C show electrophoretically separated products of microtubule co-sedimentation assays of whole cell lysates from PC3:mCh-tub cells transfected with GFP-AR (wt), GFP-C-ter AR, HA-ARv5,6,7 and GFP-ARv7 as carried out as described for FIG. 6. AR-wt AR and C-ter AR were used as positive controls of microtubule-binding. Tubulin was detected as microtubules in the WP in each condition. The boxes indicate the distribution of each protein between WP and WS fractions per condition. The extent of each variant's association with the microtubule polymer (% WP) was quantified by densitometry as described for FIG. 6 and is displayed to the right of each immunoblot. For tubulin a range of values is shown in the % WP quantitation reflecting each of the eight reactions performed. Actin was used as a negative control for microtubule association and is found in the supernatant fractions (WS) in all conditions.

FIGS. 8A and 8B show time lapse images obtained with a spinning disk confocal microscope by acquiring an entire Z-stack at 10 min intervals for 2 hr. Maximum intensity projections are shown of representative PC3:mCherry-Tub cells expressing GFP-ARv5,6,7 (FIG. 8A) or GFP-ARv7 (FIG. 8B) at the indicated time points. The integrity of the microtubule cytoskeleton from untreated, 1 µM docetaxel (TXT) or 10 µM nocodazole (Noc) treated cells was visualized with mCherry-tagged tubulin at the beginning of the time-lapse recording and is shown in the far right panels. Arrowhead points at microtubule bundles. FIGS. 8C and 8D graphically illustrate nuclear accumulation of ARv5,6,7 (FIG. 8C) or ARv7 (FIG. 8D) over time following treatment in control versus docetaxel (TXT) pretreated cells or nocodazole (Noc) pretreated cells. Quantitative analysis of nuclear of GFP-AR was performed on each focal plane (0.5 µm Z-sections through the entire cell depth) using integrated pixel intensity values from the sum projection and the percentage of nuclear AR was calculated using the following formula: % Nuclear AR=100*Nuclear AR/Total AR. Number of individual cells imaged per condition (n) ARv5,6,7: Control 0, 10, 20 and 30 min: n=16; 40-120 min: n=15. TXT pretreated 0-80 min: n=12; 90-120 min: n=10. Noc pretreated 0-50 min: n=11; 60-110 min: n=10; 120 min: n=3. N values for ARv7: Control 0-120 min: n=9. TXT pretreated 0-120 min: n=9. Noc pretreated 0-100 min: n=21, 110-120 min: n=7. Statistical test: One-way ANOVA with equal variances followed by multiple comparisons with Bonferroni adjustments.

FIG. 9A-9J illustrate that taxane treatment inhibits trafficking to the nucleus in M12 cells by AR-wt AR and ARv5,6,7, but not by ARv7. FIG. 9A shows M12 cells stably expressing GFP-tagged AR-wt AR. FIG. 9B shows M12 cells stably expressing GFP-tagged ARv5,6,7. FIG. 9C shows M12 cells stably expressing GFP-tagged ARv7. The various cell types were treated with 1 µM docetaxel (TXT) for 4 h either alone or followed by 10 nM R1881 for 2 h as indicated in the figure. Cells were then fixed, immunostained for tubulin, and imaged for GFP-AR and tubulin by confocal microscopy. Androgen receptor is shown as lighter staining (green in the original), while tubulin staining is darker but visible as lighter areas in the images (red in the original). Representative, high-magnification images from each condition are shown. Arrows point to cytoplasmic androgen receptor proteins; arrowheads point to microtubule bundles. Scale bar: 10 µm. FIG. 9D is a bar graph depicting the ratio of cells with nuclear androgen receptor over those with cytoplasmic androgen receptor for each condition. Quantitation was performed in at least 100 GFP-positive cells. *p<0.05. FIG. 9E is a bar graph illustrating RNA expression of TMPRSS2 and FKBP51 in M12 cells expressing inducible AR-wt or AR variants after the cells were treated with 1 µM docetaxel (TXT) for 4 h either alone or followed by 10 nM R1881 overnight as indicated in the figure. Relative mRNA expression of TMPRSS2 and FKBP51 was assessed by qPCR. Values were corrected to GAPDH and normalized to untreated M12 cells expressing control lentivirus (M12 lenti). Bar graphs represent the average of three independent experiments. * p<0.05. FIG. 9F shows images of AR-wt expressing control (non-treated) M12 cells or AR-wt expressing M12 cells treated with µM docetaxel for 4 hr either alone or followed by 10 nM R1881 for 2 hr as indicated. The control and treated cells express GFP-AR-wt that can be detected after staining with anti-androgen receptor or anti-N-terminal androgen receptor antibodies (reactive with the first 21 amino acids of the androgen receptor protein; also referred to as anti-ARN21 antibodies. FIG. 9G shows images of GFP-ARv5,6,7 expressing control (non-treated) M12 cells or GFP-ARv5,6,7 expressing M12 cells treated with µM docetaxel for 4 hr either alone or followed by 10 nM R1881 for 2 hr as indicated. Staining with anti-androgen receptor or anti-ARN-21 antibodies illuminated areas of androgen receptor and ANR-21 expression in the cells. FIG. 9H shows images of GFP-ARv7 expressing control (non-treated) M12 cells or GFP-ARv7 expressing M12 cells treated with µM docetaxel for 4 hr either alone or followed by 10 nM R1881 for 2 hr as indicated. Androgen receptor protein expression was detected by staining with anti-androgen receptor or anti-ARN-21 antibodies. FIGS. 9I and 9J illustrate that R1881 of M12 cells transfected with ARv5,6,7 (FIG. 9I) and ARv7 (FIG. 9J) does not increase nuclear accumulation of androgen receptor protein. M12 cells stably expressing GFP-tagged ARv5,6,7 (A) and ARv7 (B) were treated with 1 µM docetaxel for 4 hr either alone or followed by 10 nM R1881 for 2 hr as indicated. Cells were then fixed, immunostained for tubulin, and imaged for GFP-AR and tubulin by confocal microscopy. GFP-Androgen receptor proteins are shown as lighter staining (green in the original), and tubulin expression is shown as darker staining (red in the original). Scale bar: 10 μm FIG. 10A-10D illustrate that dynein associates with and mediates the nuclear translocation of ARv5,6,7, but not ARv7.

FIG. 11A graphically illustrates that LuCaP 86.2 tumor growth is markedly suppressed by a low dose of docetaxel of 5 mg/kg (P<0.01 control versus docetaxel treated). However, LuCaP 23.1 tumor growth is unaffected by docetaxel treatment. FIG. 11B shows the tumor volume over time in mice with LuCap 86.2 xenografts after treatment with 5 mg/kg docetaxel (square symbols) or 20 mg/kg weekly docetaxel (diamond symbols) treatment. FIG. 11C shows the tumor volume over time in mice with LuCap 23.12 xenografts after treatment with 5 mg/kg docetaxel (square symbols) or 20 mg/kg weekly docetaxel (diamond symbols) treatment. LuCap 86.2 (FIG. 11B) and LuCap 23.12 (FIG. 11C) human prostate cancer xenografts were treated with docetaxel 5 mg/kg weekly intraperitoneally (square symbols) or 20 mg/kg weekly intraperitoneally (diamond symbols). The study was terminated when all mice in the 5 mg/kg group meet UW IACUC criteria for euthanasia. Note that both xenografts responded to high dose docetaxel but only LuCaP 86.2 responded to low dose docetaxel. The vertical bars indicate ±SEM. Note LuCaP 86.2, which expresses predominantly ARsv5,6,7es, responds to low and high dose docetaxel but LuCaP 23.1, which expresses ARwt and ARv7 responds only to high dose docetaxel. The tumor growth curve of untreated LuCaP 86.2 xenografts is characterized by the straight line (with no symbols) in FIG. 11B. There was no difference in LuCaP 23.12 xenograft growth between untreated xenografts and those treated with a 5 mg dose of docetaxel.

DESCRIPTION

Figure 1A:
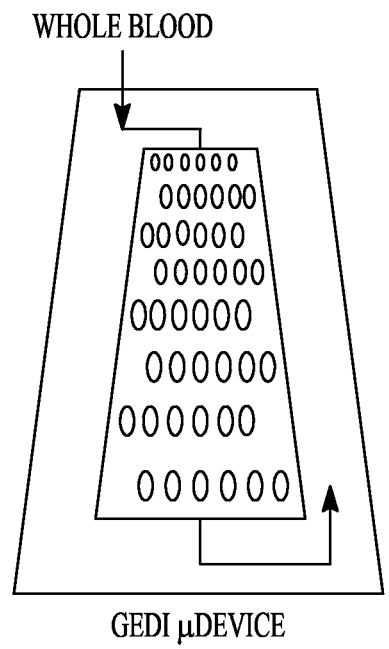
FIG. 1A-1D shows an exemplary GEDI microfluidic device.
Figure 1B:
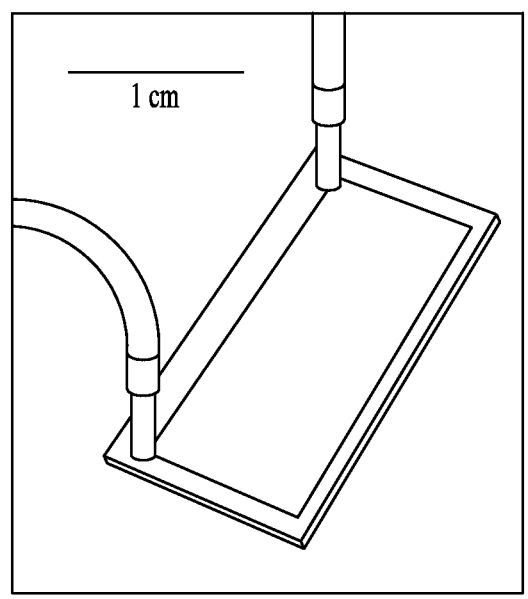

As described herein, two androgen receptor splice variants, androgen receptor variant v5,6,7 (ARv5,6,7) and androgen receptor variant v7 (AR-v7) can be used as markers for identifying prostate cancer patients who will or will not respond to taxane chemotherapy.

Androgen ablation therapy induces expression of constitutively active androgen receptor splice variants, which drive prostate cancer disease progression. The experimental data described herein indicate that patients that express the androgen receptor variant v5,6,7 (ARv5,6,7) are more sensitive to taxane chemotherapy than patients that express full-length androgen receptor or other androgen receptors. Moreover, these data also show that patients who express the androgen receptor variant v7 (AR-v7) will be resistant to taxane chemotherapy.

Androgen Receptors

Androgen receptor variants ARv5,6,7 and ARv7 (also known as AR3) appear to be the two most clinically prevalent splice variants. The ARv5,6,7 variant is present in 59% of tumor specimens from castration-resistant prostate cancer patients, and its expression arises in response to androgen deprivation therapy or abiraterone treatment (Sun et al., *J Clin Invest* 120, 2715 (August, 2010); Mostaghel et al., *Clin Cancer Res* 17, 5913 (Sep. 15, 2011)). The ARv7 variant is present in both benign and malignant prostate tissues but is generally enriched in metastatic disease (Gao et al., *Cancer Res* 69, 2305 (Mar. 15, 2009); Hornberg et al., *PLoS One* 6, e19059 (2011)). Thus, the presence of androgen receptor splice variants is common in castration-resistant prostate cancer patients and is associated with resistance to current androgen deprivation therapies.

Sequences for various androgen receptors are available, for example, from the National Center for Biotechnology Information (see website at ncbi.nlm.nih.gov).

For example, a full length human androgen receptor sequence is available from the database maintained by the National Center for Biotechnology Information (see website at ncbi.nlm.nih.gov), which has accession number P10275.2 (GI:113830), and is shown below as SEQ ID NO:1.

```
  1 MEVQLGLGRV YPRPPSKTYR GAFQNLFQSV REVIQNPGPR

41 HPEAASAAPP GASLLLLQQQ QQQQQQQQQQ QQQQQQQET

81 SPRQQQQQQG EDGSPQAHRR GPTGYLVLDE EQQPSQPQSA

121 LECHPERGCV PEPGAAVAAS KGLPQQLPAP PDEDDSAAPS

161 TLSLLGPTFP GLSSCSADLK DILSEASTMQ LLQQQQQEAV

181 SEGSSSGRAR EASGAPTSSK DNYLGGTSTI SDNAKELCKA

241 VSVSMGLGVE ALEHLSPGEQ LRGDCMYAPL LGVPPAVRPT

281 PCAPLAECKG SLLDDSAGKS TEDTAEYSPF KGGYTKGLEG

321 ESLGCSGSAA AGSSGTLELP STLSLYKSGA LDEAAAYQSR

361 DYYNFPLALA GPPPPPPPPH PHARIKLENP LDYGSAWAAA

401 AAQCRYGDLA SLHGAGAAGP GSGSPSAAAS SSWHTLFTAE

441 EGQLYGPCGG GGGGGGGGGG GGGGGGGGGG GGEAGAVAPY

481 GYTRPPQGLA GQESDFTAPD VWYPGGMVSR VPYPSPTCVK

521 SEMGPWMDSY SGPYGDMRLE TARDHVLPID YYFPPQKTCL

561 ICGDEASGCH YGALTCGSCK VFFKRAAEGK QKYLCASRND

601 CTIDKFRRKN CPSCRLRKCY EAGMTLGARK LKKLGNLKLQ

641 EEGEASSTTS PTEETTQKLT VSHIEGYECQ PIFLNVLEAI
```

```
681  EPGVVCAGHD  NNQPDSFAAL  LSSLNELGER  QLVHVVKWAK

721  ALPGFRNLHV  DDQMAVIQYS  WMGLMVFAMG  WRSFTNVNSR

761  MLYFAPDLVF  NEYRMHKSRM  YSQCVRMRHL  SQEFGWLQIT

801  PQEFLCMKAL  LLFSIIPVDG  LKNQKFFDEL  RMNYIKELDR

841  IIACKRKNPT  SCSRRFYQLT  KLLDSVQPIA  RELHQFTFDL

881  LIKSHMVSVD  FPEMMAEIIS  VQVPKILSGK  VKPIYFHTQ
```

The sequence of the androgen receptor can vary somewhat from one patient to another. For example, the number of the repetitive glutamine residues in androgen receptors (amino acids 58-89 of SEQ ID NO:1) can increase or decrease by any number between about 2-25 amino acids. Similarly, the number of repetitive glycine residues in androgen receptors (amino acids 446-472 of SEQ ID NO:1) can increase or decrease by any number between about 2-23 amino acids. Thus, the androgen receptor detected by the methods, reagents and devices described herein can have at least 75% sequence identity, or at least 80% sequence identity, or at least 85% sequence identity, or at least 90%, or at least 95% sequence identity sequence identity to SEQ ID NO:1.

Sequence identity can be evaluated using sequence analysis software (e.g., via the NCBI tools, or the Sequence Analysis Software Package of the Genetics Computer Group. University of Wisconsin Biotechnology Center. 1710 University Avenue. Madison, Wis. 53705). Such software matches similar sequences by assigning degrees of sequence identity to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Nucleotide sequences for the full-length human androgen receptor are also available from the NCBI database. For example, a cDNA sequence for the full length human androgen receptor is available as accession number M20132.1 (GI:178627), shown below as SEQ ID NO:2.

```
   1  TAATAACTCA  GTTCTTATTT  GCACCTACTT  CAGTGGACAC

41  TGAATTTGGA  AGGTGGAGGA  TTTTGTTTTT  TTCTTTTAAG

81  ATCTGGGCAT  CTTTTGAATC  TACCCTTCAA  GTATTAAGAG

121  ACAGACTGTG  AGCCTAGCAG  GGCAGATCTT  GTCCACCGTG

161  TGTCTTCTTC  TGCACGAGAC  TTTGAGGCTG  TCAGAGCGCT

201  TTTTGCGTGG  TTGCTCCCGC  AAGTTTCCTT  CTCTGGAGCT

241  TCCCGCAGGT  GGGCAGCTAG  CTGCAGCGAC  TACCGCATCA

281  TCACAGCCTG  TTGAACTCTT  CTGAGCAAGA  GAAGGGGAGG

321  CGGGGTAAGG  GAAGTAGGTG  GAAGATTCAG  CCAAGCTCAA

361  GGATGGAAGT  GCAGTTAGGG  CTGGGAAGGG  TCTACCCTCG

401  GCCGCCGTCC  AAGACCTACC  GAGGAGCTTT  CCAGAATCTG

441  TTCCAGAGCG  TGCGCGAAGT  GATCCAGAAC  CCGGGCCCCA

481  GGCACCCAGA  GGCCGCGAGC  GCAGCACCTC  CCGGCGCCAG

521  TTTGCTGCTG  CTGCAGCAGC  AGCAGCAGCA  GCAGCAGCAG

561  CAGCAGCAGC  AGCAGCAGCA  GCAGCAGCAG  CAGCAAGAGA

601  CTAGCCCCAG  GCAGCAGCAG  CAGCAGCAGG  GTGAGGATGG

641  TTCTCCCCAA  GCCCATCGTA  GAGGCCCCAC  AGGCTACCTG

681  GTCCTGGATG  AGGAACAGCA  ACCTTCACAG  CCGCAGTCGG

721  CCCTGGAGTG  CCACCCCGAG  AGAGGTTGCG  TCCCAGAGCC

761  TGGAGCCGCC  GTGGCCGCCA  GCAAGGGGCT  GCCGCAGCAG

801  CTGCCAGCAC  CTCCGGACGA  GGATGACTCA  GCTGCCCCAT

841  CCACGTTGTC  CCTGCTGGGC  CCCACTTTCC  CCGGCTTAAG

881  CAGCTGCTCC  GCTGACCTTA  AGACATCCT   GAGCGAGGCC

921  AGCACCATGC  AACTCCTTCA  GCAACAGCAG  CAGGAAGCAG

961  TATCCGAAGG  CAGCAGCAGC  GGGAGAGCGA  GGGAGGCCTC

1001  GGGGGCTCCC  ACTTCCTCCA  AGGACAATTA  CTTAGGGGGC

1041  ACTTCGACCA  TTTCTGACAA  CGCCAAGGAG  TTGTGTAAGG

1081  CAGTGTCGGT  GTCCATGGGC  CTGGGTGTGG  AGGCGTTGGA

1121  GCATCTGAGT  CCAGGGGAAC  AGCTTCGGGG  GGATTGCATG

1161  TACGCCCCAC  TTTTGGGAGT  TCCACCCGCT  GTGCGTCCCA

1201  CTCCTTGTGC  CCCATTGGCC  GAATGCAAAG  GTTCTCTGCT

1241  AGACGACAGC  GCAGGCAAGA  GCACTGAAGA  TACTGCTGAG

1281  TATTCCCCTT  TCAAGGGAGG  TTACACCAAA  GGGCTAGAAG

1321  GCGAGAGCCT  AGGCTGCTCT  GGCAGCGCTG  CAGCAGGGAG

1361  CTCCGGGACA  CTTGAACTGC  CGTCTACCCT  GTCTCTCTAC

1401  AAGTCCGGAG  CACTGGACGA  GGCAGCTGCG  TACCAGAGTC

1441  GCGACTACTA  CAACTTTCCA  CTGGCTCTGG  CCGGACCGCC

1481  GCCCCCTCCG  CCGCCTCCC   ATCCCCACGC  TCGCATCAAG

1521  CTGGAGAACC  CGCTGGACTA  CGGCAGCGCC  TGGGCGGCTG

1561  CGGCGGCGCA  GTGCCGCTAT  GGGGACCTGG  CGAGCCTGCA

1601  TGGCGCGGGT  GCAGCGGGAC  CCGGTTCTGG  GTCACCCTCA

1641  GCCGCCGCTT  CCTCATCCTG  GCACACTCTC  TTCACAGCCG

1681  AAGAAGGCCA  GTTGTATGGA  CCGTGTGGTG  GTGGTGGGGG

1721  TGGTGGCGGC  GGCGGCGGCG  GCGGCGGCGG  CGGCGGCGGC

1761  GGCGGCGGCG  GCGGCGGCGA  GGCGGGAGCT  GTAGCCCCCT

1801  ACGGCTACAC  TCGGCCCCCT  CAGGGGCTGG  CGGGCCAGGA

1841  AAGCGACTTC  ACCGCACCTG  ATGTGTGGTA  CCCTGGCGGC

1881  ATGGTGAGCA  GAGTGCCCTA  TCCCAGTCCC  ACTTGTGTCA

1921  AAAGCGAAAT  GGGCCCCTGG  ATGGATAGCT  ACTCCGGACC

1961  TTACGGGGAC  ATGCGTTTGG  AGACTGCCAG  GGACCATGTT

2001  TTGCCCATTG  ACTATTACTT  TCCACCCCAG  AAGACCTGCC

2041  TGATCTGTGG  AGATGAAGCT  TCTGGGTGTC  ACTATGGAGC

2081  TCTCACATGT  GGAAGCTGCA  AGGTCTTCTT  CAAAAGAGCC

2121  GCTGAAGGGA  AACAGAAGTA  CCTGTGCGCC  AGCAGAAATG
```

```
2161 ATTGCACTAT TGATAAATTC CGAAGGAAAA ATTGTCCATC
2201 TTGTCGTCTT CGGAAATGTT ATGAAGCAGG GATGACTCTG
2241 GGAGCCCGGA AGCTGAAGAA ACTTGGTAAT CTGAAACTAC
2281 AGGAGGAAGG AGAGGCTTCC AGCACCACCA GCCCCACTGA
2321 GGAGACAACC CAGAAGCTGA CAGTGTCACA CATTGAAGGC
2361 TATGAATGTC AGCCCATCTT TCTGAATGTC CTGGAAGCCA
2401 TTGAGCCAGG TGTAGTGTGT GCTGGACACG ACAACAACCA
2441 GCCCGACTCC TTTGCAGCCT TGCTCTCTAG CCTCAATGAA
2481 CTGGGAGAGA GACAGCTTGT ACACGTGGTC AAGTGGGCCA
2521 AGGCCTTGCC TGGCTTCCGC AACTTACACG TGGACGACCA
2561 GATGGCTGTC ATTCAGTACT CCTGGATGGG GCTCATGGTG
2601 TTTGCCATGG GCTGGCGATC CTTCACCAAT GTCAACTCCA
2641 GGATGCTCTA CTTCGCCCCT GATCTGGTTT TCAATGAGTA
2681 CCGCATGCAC AAGTCCCGGA TGTACAGCCA GTGTGTCCGA
2721 ATGAGGCACC TCTCTCAAGA GTTTGGATGG CTCCAAATCA
2761 CCCCCCAGGA ATTCCTGTGC ATGAAAGCAC TGCTACTCTT
2801 CAGCATTATT CCAGTGGATG GGCTGAAAAA TCAAAAATTC
2841 TTTGATGAAC TTCGAATGAA CTACATCAAG GAACTCGATC
2881 GTATCATTGC ATGCAAAAGA AAAAATCCCA CATCCTGCTC
2921 AAGACGCTTC TACCAGCTCA CCAAGCTCCT GGACTCCGTG
2961 CAGCCTATTG CGAGAGAGCT GCATCAGTTC ACTTTTGACC
3001 TGCTAATCAA GTCACACATG GTGAGCGTGG ACTTTCCGGA
3041 AATGATGGCA GAGATCATCT CTGTGCAAGT GCCCAAGATC
3081 CTTTCTGGGA AAGTCAAGCC CATCTATTTC CACACCCAGT
3121 GAAGCATTGG AAACCCTATT TCCCCACCCC AGCTCATGCC
3161 CCCTTTCAGA TGTCTTCTGC CTGTTATAAC TCTGCACTAC
3201 TCCTCTGCAG TGCCTTGGGG AATTTCCTCT ATTGATGTAC
3241 AGTCTGTCAT GAACATGTTC CTGAATTCTA TTTGCTGGGC
3281 TTTTTTTTTC TCTTTCTCTC CTTTCTTTTT CTTCTTCCCT
3321 CCCTATCTAA CCCTCCCATG GCACCTTCAG ACTTTGCTTC
3361 CCATTGTGGC TCCTATCTGT GTTTTGAATG GTGTTGTATG
3401 CTTTAAATC TGTGATGATC CTCATATGGC CCAGTGTCAA
3441 GTTGTGCTTG TTTACAGCAC TACTCTGTGC CAGCCACACA
3481 AACGTTTACT TATCTTATGC CACGGGAAGT TTAGAGAGCT
3521 AAGATTATCT GGGGAAATCA AAACAAAAA CAAGCAAACA
3561 AAAAAAAA
```

A sequence for androgen receptor variant 5,6,7es [*Homo sapiens*] is also available from the NCBI database National Center for Biotechnology Information (see website at ncbi.nlm.nih.gov). This androgen receptor variant lacks exons 5, 6, and 7. The NCBI database provides a sequence for a human androgen receptor variant 5,6,7es with accession number ACZ81436.1 (GI:270358642) (SEQ ID NO:3).

```
  1 MEVQLGLGRV YPRPPSKTYR GAFQNLFQSV REVIQNPGPR
 41 HPEAASAAPP GASLLLLQQQ QQQQQQQQQQ QQQQQQQQQQ
 81 QETSPRQQQQ QQGEDGSPQA HRRGPTGYLV LDEEQQPSQP
121 QSALECHPER GCVPEPGAAV AASKGLPQQL PAPPDEDDSA
161 APSTLSLLGP TFPGLSSCSA DLKDILSEAS TMQLLQQQQQ
201 EAVSEGSSSG RAREASGAPT SSKDNYLGGT STISDNAKEL
241 CKAVSVSMGL GVEALEHLSP GEQLRGDCMY APLLGVPPAV
281 RPTPCAPLAE CKGSLLDDSA GKSTEDTAEY SPFKGGYTKG
321 LEGESLGCSG SAAAGSSGTL ELPSTLSLYK SGALDEAAAY
361 QSRDYYNFPL ALAGPPPPPP PPHPHARIKL ENPLDYGSAW
401 AAAAAQCRYG DLASLHGAGA AGPGSGSPSA AASSSWHTLF
441 TAEEGQLYGP CGGGGGGGGG GGGGGGGGGG GGGGGGGEA
481 GAVAPYGYTR PPQGLAGQES DFTAPDVWYP GGMVSRVPYP
521 SPTCVKSEMG PWMDSYSGPY GDMRLETARD HVLPIDYYFP
561 PQKTCLICGD EASGCHYGAL TCGSCKVFFK RAAEGKQKYL
601 CASRNDCTID KFRRKNCPSC RLRKCYEAGM TLGARKLKKL
641 GNLKLQEEGE ASSTTSPTEE TTQKLTVSHI EGYECQPIFL
681 NVLEAIEPGV VCAGHDNNQP DSFAALLSSL NELGERQLVH
721 VVKWAKALPD CERAASVHF
```

The sequence of the androgen receptor splice variant v5,6,7 can vary somewhat from one patient to another. For example, the androgen receptor splice variant v5,6,7 detected by the methods, reagents and devices described herein can have at least 75% sequence identity, or at least 80% sequence identity, or at least 85% sequence identity, or at least 90%, or at least 95% sequence identity sequence identity to SEQ ID NO:3.

Nucleotide sequences for the human androgen receptor variant v5,6,7 are also available from the NCBI database. For example, a cDNA sequence for the SEQ ID NO:3 human androgen receptor variant v5,6,7 is available as accession number GU208210.1 (GI:270358641), shown below as SEQ ID NO:4.

```
  1 AGGATGGAAG TGCAGTTAGG GCTGGGAAGG GTCTACCCTC
 41 GGCCGCCGTC CAAGACCTAC CGAGGAGCTT TCCAGAATCT
 81 GTTCCAGAGC GTGCGCGAAG TGATCCAGAA CCCGGGCCCC
121 AGGCACCCAG AGGCCGCGAG CGCAGCACCT CCCGGCGCCA
161 GTTTGCTGCT GCTGCAGCAG CAGCAGCAGC AGCAGCAGCA
201 GCAGCAGCAG CAGCAGCAGC AGCAGCAGCA GCAGCAGCAG
241 CAGCAAGAGA CTAGCCCCAG GCAGCAGCAG CAGCAGCAGG
281 GTGAGGATGG TTCTCCCCAA GCCCATCGTA GAGGCCCCAC
321 AGGCTACCTG GTCCTGGATG AGGAACAGCA ACCTTCACAG
361 CCGCAGTCGG CCCTGGAGTG CCACCCCGAG AGAGGTTGCG
401 TCCCAGAGCC TGGAGCCGCC GTGGCCGCCA GCAAGGGGCT
441 GCCGCAGCAG CTGCCAGCAC CTCCGGACGA GGATGACTCA
```

```
481   GCTGCCCCAT CCACGTTGTC CTGCTGGGC CCCACTTTCC
521   CCGGCTTAAG CAGCTGCTCC GCTGACCTTA AAGACATCCT
561   GAGCGAGGCC AGCACCATGC AACTCCTTCA GCAACAGCAG
601   CAGGAAGCAG TATCCGAAGG CAGCAGCAGC GGGAGAGCGA
641   GGGAGGCCTC GGGGGCTCCC ACTTCCTCCA AGGACAATTA
681   CTTAGGGGGC ACTTCGACCA TTTCTGACAA CGCCAAGGAG
721   TTGTGTAAGG CAGTGTCGGT GTCCATGGGC CTGGGTGTGG
761   AGGCGTTGGA GCATCTGAGT CCAGGGGAAC AGCTTCGGGG
801   GGATTGCATG TACGCCCCAC TTTTGGGAGT TCCACCCGCT
841   GTGCGTCCCA CTCCTTGTGC CCCATTGCC GAATGCAAAG
881   GTTCTCTGCT AGACGACAGC GCAGGCAAGA GCACTGAAGA
921   TACTGCTGAG TATTCCCCTT TCAAGGGAGG TTACACCAAA
961   GGGCTAGAAG GCGAGAGCCT AGGCTGCTCT GGCAGCGCTG
1001  CAGCAGGGAG CTCCGGGACA CTTGAACTGC CGTCTACCCT
1041  GTCTCTCTAC AAGTCCGGAG CACTGGACGA GGCAGCTGCG
1081  TACCAGAGTC GCGACTACTA CAACTTTCCA CTGGCTCTGG
1121  CCGGACCGCC GCCCCCTCCG CCGCCTCCCC ATCCCACGC
1161  TCGCATCAAG CTGGAGAACC CGCTGGACTA CGGCAGCGCC
1201  TGGGCGGCTG CGGCGGCGCA GTGCCGCTAT GGGGACCTGG
1241  CGAGCCTGCA TGGCGCGGGT GCAGCGGGAC CCGGTTCTGG
1281  GTCACCCTCA GCCGCCGCTT CCTCATCCTG GCACACTCTC
1321  TTCACAGCCG AAGAAGGCCA GTTGTATGGA CCGTGTGGTG
1361  GTGGTGGGGG TGGTGGCGGC GGCGGCGCG GCGGCGGCGG
1401  CGGCGGCGGC GGCGGCGGCG GCGGCGGCGG CGGCGGCGAG
1441  GCGGGAGCTG TAGCCCCCTA CGGCTACACT CGGCCCCCTC
1481  AGGGGCTGGC GGGCCAGGAA AGCGACTTCA CCGCACCTGA
1521  TGTGTGGTAC CCTGGCGGCA TGGTGAGCAG AGTGCCCTAT
1561  CCCAGTCCCA CTTGTGTCAA AAGCGAAATG GGCCCCTGGA
1601  TGGATAGCTA CTCCGGACCT TACGGGGACA TGCGTTTGGA
1641  GACTGCCAGG GACCATGTTT TGCCCATTGA CTATTACTTT
1681  CCACCCCAGA AGACCTGCCT GATCTGTGGA GATGAAGCTT
1721  CTGGGTGTCA CTATGGAGCT CTCACATGTG GAAGCTGCAA
1761  GGTCTTCTTC AAAAGAGCCG CTGAAGGGAA ACAGAAGTAC
1801  CTGTGCGCCA GCAGAAATGA TTGCACTATT GATAAATTCC
1841  GAAGGAAAAA TTGTCCATCT TGTCGTCTTC GGAAATGTTA
1881  TGAAGCAGGG ATGACTCTGG GAGCCCGGAA GCTGAAGAAA
1921  CTTGGTAATC TGAAACTACA GGAGGAAGGA GAGGCTTCCA
1961  GCACCACCAG CCCCACTGAG GAGACAACCC AGAAGCTGAC
2001  AGTGTCACAC ATTGAAGGCT ATGAATGTCA GCCCATCTTT
2041  CTGAATGTCC TGGAAGCCAT TGAGCCAGGT GTAGTGTGTG
2081  CTGGACACGA CAACAACCAG CCCGACTCCT TTGCAGCCTT
2121  GCTCTCTAGC CTCAATGAAC TGGGAGAGAG ACAGCTTGTA
2161  CACGTGGTCA AGTGGGCCAA GGCCTTGCCT GATTGCGAGA
2201  GAGCTGCATC AGTTCACTTT TGACCTGCTA ATCAAGTCAC
2241  ACATGGTGAG CGTGGACTTT CCGGAAATGA TGGCAGAGAT
2281  CATCTCTGTG CAAGTGCCCA AGATCCTTTC TGGGAAAGTC
2321  AAGCCCATCT ATTTCCACAC CCAGTGAAGC ATTGGAAACC
2361  CTATTTCCCC ACCCCAGCTC ATGCCCCCTT TCAGATGTCT
2401  TCTGCCTGTT ATAACTCTGC ACTACTCCTC TGCAGTGCCT
2441  TG
```

A sequence for human androgen receptor variant 7 is also available from the NCBI database with accession number ACN39559.1 (GI:224181614) (SEQ ID NO:5).

```
  1 MEVQLGLGRV YPRPPSKTYR GAFQNLFQSV REVIQNPGPR
 41 HPEAASAAPP GASLLLQQQQ QQQQQQQQQQ QQQQQQQQQ
 61 QQQQQETSPR QQQQQQGEDG SPQAHRRGPT GYLVLDEEQQ
121 PSQPQSALEC HPERGCVPEP GAAVAASKGL PQQLPAPPDE
161 DDSAAPSTLS LLGPTFPGLS SCSADLKDIL SEASTMQLLQ
201 QQQQEAVSEG SSSGRAREAS GAPTSSKDNY LGGTSTISDN
241 AKELCKAVSV SMGLGVEALE HLSPGEQLRG DCMYAPLLGV
281 PPAVRPTPCA PLAECKGSLL DDSAGKSTED TAEYSPFKGG
321 YTKGLEGESL GCSGSAAAGS SGTLELPSTL SLYKSGALDE
361 AAAYQSRDYY NFPLALAGPP PPPPPHPHA RIKLENPLDY
401 GSAWAAAAAQ CRYGDLASLH GAGAAGPGSG SPSAAASSSW
441 HTLFTAEEGQ LYGPCGGGGG GGGGGGGGG GGGGEAGAVA
481 PYGYTRPPQG LAGQESDFTA PDVWYPGGMV SRVPYPSPTC
521 VKSEMGPWMD SYSGPYGDMR LETARDHVLP IDYYFPPQKT
561 CLICGDEASG CHYGALTCGS CKVFFKRAAE GKQKYLCASR
601 NDCTIDKFRR KNCPSCRLRK CYEAGMTLGE KFRVGNCKHL
641 KMTRP
```

The sequence of the androgen receptor splice variant v7 can vary somewhat from one patient to another. For example, the androgen receptor splice variant v7 detected by the methods, reagents and devices described herein can have at least 75% sequence identity, or at least 80% sequence identity, or at least 85% sequence identity, or at least 90%, or at least 95% sequence identity sequence identity to SEQ ID NO:5.

Nucleotide sequences for the human androgen receptor variant v7 are also available from the NCBI database. For example, a cDNA sequence for the SEQ ID NO:5 human androgen receptor variant v7 is available as accession number FJ235916.1 (GI:224181613), shown below as SEQ ID NO:6.

```
   1 GACACTGAAT TTGGAAGGTG GAGGATTTTG TTTTTTTCTT
  41 TTAAGATCTG GGCATCTTTT GAATCTACCC TTCAAGTATT
  81 AAGAGACAGA CTGTGAGCCT AGCAGGGCAG ATCTTGTCCA
 121 CCGTGTGTCT TCTTCTGCAC GAGACTTTGA GGCTGTCAGA
 161 GCGCTTTTTG CGTGGTTGCT CCCGCAAGTT TCCTTCTCTG
 201 GAGCTTCCCG CAGGTGGGCA GCTAGCTGCA GCGACTACCG
 241 CATCATCACA GCCTGTTGAA CTCTTCTGAG CAAGAGAAGG
 281 GGAGGCGGGG TAAGGGAAGT AGGTGGAAGA TTCAGCCAAG
 321 CTCAAGGATG GAAGTGCAGT TAGGGCTGGG AAGGGTCTAC
 361 CCTCGGCCGC CGTCCAAGAC CTACCGAGGA GCTTTCCAGA
 401 ATCTGTTCCA GAGCGTGCGC GAAGTGATCC AGAACCCGGG
 441 CCCCAGGCAC CCAGAGGCCG CGAGCGCAGC ACCTCCCGGC
 481 GCCAGTTTGC TGCTGCAGCA GCAGCAGCAG CAGCAGCAGC
 521 AGCAGCAGCA GCAGCAGCAG CAGCAGCAGC AGCAGCAGCA
 561 GCAGCAGCAG CAGCAGCAGC AAGAGACTAG CCCCAGGCAG
 601 CAGCAGCAGC AGCAGGGTGA GGATGGTTCT CCCCAAGCCC
 641 ATCGTAGAGG CCCCACAGGC TACCTGGTCC TGGATGAGGA
 681 ACAGCAACCT TCACAGCCGC AGTCGGCCCT GGAGTGCCAC
 721 CCCGAGAGAG GTTGCGTCCC AGAGCCTGGA GCCGCCGTGG
 761 CCGCCAGCAA GGGGCTGCCG CAGCAGCTGC CAGCACCTCC
 801 GGACGAGGAT GACTCAGCTG CCCCATCCAC GTTGTCCCTG
 841 CTGGGCCCCA CTTTCCCCGG CTTAAGCAGC TGCTCCGCTG
 881 ACCTTAAAGA CATCCTGAGC GAGGCCAGCA CCATGCAACT
 921 CCTTCAGCAA CAGCAGCAGG AAGCAGTATC CGAAGGCAGC
 961 AGCAGCGGGA GAGCGAGGGA GGCCTCGGGG CTCCCACTT
1001 CCTCCAAGGA CAATTACTTA GGGGCACTT CGACCATTTC
1041 TGACAACGCC AAGGAGTTGT GTAAGGCAGT GTCGGTGTCC
1081 ATGGGCCTGG GTGTGGAGGC GTTGGAGCAT CTGAGTCCAG
1121 GGAACAGCT TCGGGGGAT TGCATGTACG CCCCACTTTT
1161 GGGAGTTCCA CCCGCTGTGC GTCCCACTCC TTGTGCCCCA
1201 TTGGCCGAAT GCAAAGGTTC TCTGCTAGAC GACAGCGCAG
1241 GCAAGAGCAC TGAAGATACT GCTGAGTATT CCCCTTTCAA
1281 GGGAGGTTAC ACCAAAGGGC TAGAAGGCGA GAGCCTAGGC
1321 TGCTCTGGCA GCGCTGCAGC AGGGAGCTCC GGGACACTTG
1361 AACTGCCGTC TACCCTGTCT CTCTACAAGT CCGGAGCACT
1401 GGACGAGGCA GCTGCGTACC AGAGTCGCGA CTACTACAAC
1441 TTTCCACTGG CTCTGGCCGG ACCGCCGCCC CCTCCGCCGC
1481 CTCCCCATCC CCACGCTCGC ATCAAGCTGG AGAACCCGCT
1521 GGACTACGGC AGCGCCTGGG CGGCTGCGGC GGCGCAGTGC
1561 CGCTATGGGG ACCTGGCGAG CCTGCATGGC GCGGGTGCAG
1601 CGGGACCCGG TTCTGGGTCA CCCTCAGCCG CCGCTTCCTC
1641 ATCCTGGCAC ACTCTCTTCA CAGCCGAAGA AGGCCAGTTG
1681 TATGGACCGT GTGGTGGTGG TGGGGGTGGT GGCGGCGGCG
1721 GCGGCGGCGG CGGCGGCGGC GGCGGCGGCG AGGCGGGAGC
1761 TGTAGCCCCC TACGGCTACA CTCGGCCCCC TCAGGGGCTG
1801 GCGGGCCAGG AAAGCGACTT CACCGCACCT GATGTGTGGT
1841 ACCCTGGCGG CATGGTGAGC AGAGTGCCCT ATCCCAGTCC
1881 CACTTGTGTC AAAAGCGAAA TGGGCCCCTG GATGGATAGC
1921 TACTCCGGAC CTTACGGGGA CATGCGTTTG GAGACTGCCA
1961 GGGACCATGT TTTGCCCATT GACTATTACT TCCACCCCA
2001 GAAGACCTGC CTGATCTGTG GAGATGAAGC TTCTGGGTGT
2041 CACTATGGAG CTCTCACATG TGGAAGCTGC AAGGTCTTCT
2081 TCAAAAGAGC CGCTGAAGGG AAACAGAAGT ACCTGTGCGC
2121 CAGCAGAAAT GATTGCACTA TTGATAAATT CCGAAGGAAA
2161 AATTGTCCAT CTTGTCGTCT TCGGAAATGT TATGAAGCAG
2201 GGATGACTCT GGGAGAAAAA TTCCGGGTTG GCAATTGCAA
2241 GCATCTCAAA ATGACCAGAC CTGAAGAAAA GGCTGACTTG
2281 CCTCATTCAA AATGAGGGCT CTAGAGGGCT CTAGTGGATA
2321 GTCTGGAGAA ACCTGGCGTC TGAGGCTTAG GAGCTTAGGT
2361 TTTTGCTCCT CAACACAGAC TTTGACGTTG GGGTTGGGGG
2401 CTACTCTCTT GATTGCTGAC TCCCTCCAGC GGGACCAATA
2441 GTGTTTTCCT ACCTCACAGG GATGTTGTGA GGACGGGCTG
2481 TAGAAGTAAT AGTGGTTACC ACTCATGTAG TTGTGAGTAT
2521 CATGATTATT GTTTCCTGTA ATGTGGCTTG GCATTGGCAA
2561 AGTGCTTTTT GATTGTTCTT GATCACATAT GATGGGGGCC
2601 AGGCACTGAC TCAGGCGGAT GCAGTGAAGC TCTGGCTCAG
2641 TCGCTTGCTT TTCGTGGTGT GCTGCCAGGA AGAAACTTTG
2681 CTGATGGGAC TCAAGGTGTC ACCTTGGACA AGAAGCAACT
2721 GTGTCTGTCT GAGGTTCCTG TGGCCATCTT TATTTGTGTA
2761 TTAGGCAATT CGTATTTCCC CCTTAGGTTC TAGCCTTCTG
2801 GATCCCAGCC AGTGACCTAG ATCTTAGCCT CAGGCCCTGT
2841 CACTGAGCTG AAGGTAGTAG CTGATCCACA GAAGTTCAGT
2881 AAACAAGGAC CAGATTTCTG CTTCTCCAGG AGAAGAAGCC
2921 AGCCAACCCC TCTCTTCAAA CACACTGAGA GACTACAGTC
2961 CGACTTTCCC TCTTACATCT AGCCTTACTG TAGCCACACT
3001 CCTTGATTGC TCTCTCACAT CACATGCTTC TCTTCATCAG
3041 TTGTAAGCCT CTCATTCTTC TCCCAAGCCA GACTCAAATA
3081 TTGTATTGAT GTCAAAGAAG AATCACTTAG AGTTTGGAAT
3121 ATCTTGTTCT CTCTCTGCTC CATAGCTTCC ATATTGACAC
3161 CAGTTTCTTT CTAGTGGAGA AGTGGAGTCT GTGAAGCCAG
3201 GGAAACACAC ATGTGAGAGT CAGAAGGACT CTCCCTGACT
```

```
-continued
3241 TGCCTGGGGC CTGTCTTTCC CACCTTCTCC AGTCTGTCTA

3281 AACACACACA CACACACACA CACACACACA CACACACACA

3321 CACACGCTCT CTCTCTCTCT CCCCCCCCAA CACACACACA

3361 CTCTCTCTCT CACACACACA CACATACACA CACACTTCTT

3401 TCTCTTTCCC CTGACTCAGC AACATTCTGG AGAAAAGCCA

3441 AGGAAGGACT TCAGGAGGGG AGTTTCCCCC TTCTCAGGGC

3481 AGAATTTTAA TCTCCAGACC AACAAGAAGT TCCCTAATGT

3521 GGATTGAAAG GCTAATGAGG TTTATTTTTA ACTACTTTCT

3561 ATTTGTTTGA ATGTTGCATA TTTCTACTAG TGAAATTTTC

3601 CCTTAATAAA GCCATTAATA CACCCAAAAA AAAAAAAAA

3641 A
```

The inventors have recently determined that the androgen receptor (AR) binds cellular microtubules (MTs) and utilizes them as tracks for nuclear translocation, with the aid of the microtubule-associated motor protein dynein (Darshan et al., Taxane-Induced Blockade to Nuclear Accumulation of the Androgen Receptor Predicts Clinical Responses in Metastatic Prostate Cancer. Cancer research. (2011)). In this application, the inventors extend these observations to the clinical setting by analyzing the subcellular androgen receptor localization in circulating tumor cells (CTCs) isolated from castration-resistant prostate cancer patients (e.g., about 30 patients) receiving taxane chemotherapy. These analyses revealed a significant relationship between androgen receptor cytoplasmic sequestration and clinical response to taxane treatment using PSAWG2 or Prostate Cancer Working Group 2 criteria. The Prostate Cancer Working Group 2 criteria are generally described, for example, by Bubley et al. (J. Clin. Oncol. 17:3461-67 (1999)); and Scher et al. (J. Clin. Oncol. 26(7): 1148-59 (2008)), which are both specifically incorporated herein by reference in their entireties. Taken together, the results challenge the existing paradigm in which the clinical activity of the taxanes is largely attributed to their antimitotic effects.

As described herein, the ARv5,6,7 and AR-v7 androgen receptors were evaluated for their ability to bind microtubules, translocate to the nucleus with dynein and respond to taxane treatment. Data described herein shows that the two variants behave differently in all aspects. Microtubule co-sedimentation revealed that ARv5,6,7 is associated with microtubules, in contrast to the significantly reduced association displayed by AR-v7. Dynamitin overexpression inhibited the nuclear accumulation of full length androgen receptor and ARv5,6,7 but had no effect on AR-V7, indicating that AR-v7's nuclear translocation is independent of dynein-based microtubules transport.

To examine the impact of taxane treatment on variant activity we microinjected GFP-tagged full length androgen receptor, or variants into the nucleus of PC3 prostate cancer cells and monitored the dynamics of nuclear translocation of androgen receptor proteins using live-cell confocal microscopy and androgen receptor transcriptional activity using a luciferase reporter assay. The data described herein shows that taxanes significantly inhibited the nuclear accumulation and activity of full length androgen receptor and ARv5,6,7 but not that of AR-v7. Moreover, the tumor volume of human xenografts models expressing the ARv5,6,7 were significantly reduced in response to taxane treatment as compared with xenografts expressing either full length androgen receptor or other variants. Taken together these data reveal that functional microtubules are required for ARv5,6,7 nuclear transport, but this not so for AR-v7, which is not under microtubule control and thus, remains insensitive to taxane treatment.

Clinically, the taxanes (e.g., paclitaxel, docetaxel and cabazitaxel), represent the only class of chemotherapy drugs that improve survival in castration-resistant prostate cancer patients. However, not all patients respond and the clinical efficacy of taxanes can be transient. Currently, there are two clinical questions that remain to be answered:

1) how can we predict which patients will benefit the most from taxane-based chemotherapy and can we identify patients more likely to respond to paclitaxel, docetaxel or cabazitaxel 2) what are the mechanisms contributing to the development of clinical taxane resistance in metastatic prostate cancer.

As described herein, the presence of distinct androgen receptor splice variants that were identified in castration-resistant prostate cancer patients can be used as a predictive biomarker of taxane sensitivity. The new data show that the commonly expressed ARv5,6,7 (which lacks exons 5, 6 and 7 harboring the ligand-binding domain) binds microtubules and is sensitive to taxane-induced inhibition of its nuclear accumulation; while the ARv7 variant does not bind microtubules and its nuclear accumulation is not affected by taxane treatment.

Further work has demonstrated that xenografts with tumors expressing the ARv5,6,7 variant are much more sensitive to docetaxel treatment compared with xenografts whose tumors express full-length wild-type androgen receptor.

Detection Methods

A variety of methods can be used for identifying patients for treatment with taxanes, and for avoiding taxane treatment when it will likely have no beneficial effects.

Prostate cancer patients who can benefit from administration of one or more taxanes can be identified by observation that the androgen variant v5,6,7 is expressed by cells within samples taken from the patient(s). Such taxane responsive patients can be identified through detection of the ARv5,6,7 variant in RNA molecules or via the encoded ARv5,6,7 variant protein in a biological sample comprising tumor cells obtained from the patient.

A patient population of individuals who are likely to be resistant or non-respondent to taxane treatment can be identified by observation that the androgen variant v7 is expressed by cells within samples taken from the individual(s). Such non-taxane responsive patients can be identified through detection of the ARv7 variant in RNA molecules or via the encoded ARv7 variant protein in a biological sample comprising tumor cells obtained from the patient.

The biological sample can, for example, be circulating tumor cells, or prostate tissue sample. The biological sample can also, for example, be a fresh or frozen or archived paraffin-embedded and fixed (e.g. formalin-fixed) tissue sample, routinely prepared and preserved in everyday clinical practice. The biological sample can also be a different sample obtained from the patient, such as a biological fluid, including, without limitation, blood, urine, saliva, ascites fluid, or derivatives such as blood serum and blood plasma, and the like.

Various methods for determining expression of mRNA or protein include, but are not limited to, gene expression profiling, polymerase chain reaction (PCR) including quantitative real time PCR (qRT-PCR), microarray analysis that can be performed by commercially available equipment, following manufacturer's protocols, such as by using the Affymetrix GenChip technology, serial analysis of gene expression (SAGE) (Velculescu et al, Science 270:484-487 (1995); and Velculescu el al, Cell 88:243-51 (1997)), MassARRAY, Gene Expression Analysis by Massively Parallel Signature Sequencing (MPSS) (Brenner et al, Nature Biotechnology 18:630-634 (2000)), proteomics, immunohistochemistry (IHC), etc. For example, methods for detecting and/or quantifying expression of mRNA can include Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, and combinations thereof.

The mRNA levels encoding the androgen receptor variant can be quantified. Such mRNA analysis is can be performed using the technique of polymerase chain reaction (PCR), or by microarray analysis. Quantitative real time PCR (qRT-PCR) can be used to quantify the mRNA levels.

Polynucleotide microarrays can be used to simultaneously measure whether or not any of several microRNAs are expressed. Generally, microarrays include probes for a plurality of microRNAs informative for benign/malignancy determination, for a particular disease or condition, and, in particular, for individuals having specific combinations of genotypic or phenotypic characteristics of the disease or condition (i.e., that are prognosis-informative for a particular patient subset).

A standard Northern blot assay can be used to ascertain an RNA transcript size, and the relative amounts of mRNA in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., a microRNA from a different species or genomic DNA fragments that might contain an exon) may be used as probes. The labeled probe can be a labeled cDNA; a full-length, single stranded labeled RNA or DNA, or a labeled fragment of that RNA or DNA sequence.

Such a RNA or DNA (or fragments therefore) may serve as a probe, for example, when it is at least 9, at least 10, at least 11, at least 12, at least 13, at least 14, at least 15, or at least 16 consecutive nucleotides in length. In some embodiments, the probe is about 9, about 10, about 11, about 12, about 13, about 14, about 15, about 16, about 17, about 18, about 19, about 20, about 21 or about 22 consecutive nucleotides in length. In further embodiments, the probe may be at least 20, at least 30, at least 50, or at least 70 consecutive nucleotides in length. The primers and/or probes can be less than about 80, less than about 70, less than about 60, less than about 50, less than about 45, less than about 40, less than about 39, less than about 38, less than about 37, less than about 36, less than about 35, less than about 34, less than about 33, less than about 32, less than about 31, or less than about 30 consecutive nucleotides in length.

The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow.

Methods for profiling gene expression using fixed, paraffin-embedded tissues as the RNA source can also be employed. Such methods can include mRNA isolation, purification, primer extension and amplification are given in various published journal articles (for example: Godfrey et al J. Molec. Diagnostics 2: 84-91 (2000); Specht et al, Am. J. Pathol 158:419-29 (2001)). Briefly, a representative process starts with cutting about 10 microgram thick sections of paraffin-embedded tumor tissue samples. The mRNA is then extracted, and protein and DNA are removed. General methods for mRNA extraction are well known in the art and are disclosed in standard textbooks of molecular biology, including Aiisubel et al, Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al, BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation. After analysis of the RNA concentration, RNA repair and/or amplification steps may be included, if necessary, and RNA is reverse transcribed using gene specific promoters followed by PCR. Nuclease protection assays such as ribonuclease protection assays and S1 nuclease assays can be used to detect and quantify specific microRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

A ribonuclease protection assay employs RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Serial Analysis Gene Expression (SAGE), which is described in e.g., Velculescu et al., 1995, *Science* 270:484-7; Carulli, et al., 1998, *Journal of Cellular Biochemistry Supplements* 30/31:286-96, can also be used to determine RNA abundances in a cell sample.

Quantitative reverse transcriptase PCR (qRT-PCR) can also be used to determine the expression profiles of microRNA genes (see, e.g., U.S. Patent Application Publication No. 2005/0048542A1). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

An assay involving PCR can use a variety of thermostable DNA-dependent DNA polymerases. Commonly employed polymerases include the Taq DNA polymerase, which has a 5'-3' nuclease activity but lacks a 3'-5' proofreading endonuclease activity. Taq Man® PCR typically utilizes the 5'-nuclease activity of Taq or Tth polymerase to hydrolyze a hybridization probe bound to its target amplicon, but any enzyme with similar or equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 77QQ™. Sequence Detection System™ (Perkin-Elmer-Applied Biosystems, Foster City, Calif., USA), or Lightcycler (Roche Molecular Biochemicals, Mannheim, Germany). In one embodiment, the 5' nuclease procedure is run on a real-time quantitative PCR device such as the ABI PRISM 77QQ™ Sequence Detection System™. The system consists of a thermocycler, laser, charge-coupled device (CCD), camera and computer. The system includes software for running the instrument and for analyzing the data.

For example, the following primers and/or probes can be used to detect the v5,6,7 variant of the human androgen receptor:

```
Probe:
                                           (SEQ ID NO: 10)
5'-CCTTGCCTGATTGCGAGA-3'.

Forward primer:
                                           (SEQ ID NO: 11)
5'-CCTTGCTCTCTAGCCTCAATGAA-3'.

Reverse primer:
                                           (SEQ ID NO: 12)
5'-CTTGATTAGCAGGTCAAAAGTGAACT-3'.
```

To minimize errors and the effect of sample-to-sample variation, RT-PCR is often performed using an internal standard. The ideal internal standard is expressed at a constant level among different tissues, and is unaffected by the experimental treatment. RNAs most frequently used to normalize patterns of gene expression are 18S rRNA or mRNAs for the housekeeping genes such as glyceraldehyde-3-phosphate-dehydrogenase (GAPDH) or β-actin.

Real time PCR can be used in the methods, which is compatible both with quantitative competitive PCR, where internal competitor for each target sequence is used for normalization, and with quantitative comparative PCR using a normalization gene contained within the sample, or a housekeeping gene for RT-PCR. For further details see, e.g. "PCR: The Polymerase Chain Reaction", Miillis et al., eds., 1994; and Held et al, Genome Research 6:986-994 (1996); Held et al., Genome Research 6:986-994 (1996). Finally, the data are analyzed to identify the best treatment option(s) available to the patient on the basis of the characteristic gene expression pattern identified in the tumor sample examined.

In some embodiments, the quantitative RT-PCR assay data are presented as Ct values, also referred to as $\Delta Ct$ thresholds. The $\Delta Ct$ (cycle threshold) is defined as the number of cycles required for the fluorescent signal to cross a detectable threshold. The $\Delta Ct$ is a measure of when the amount of RNA expressed exceeds background levels. Ct threshold levels are inversely proportional to the amount of target nucleic acid in the sample (i.e., the lower the Ct threshold the greater the amount of target nucleic acid in the sample). Fluorescence values are recorded during every cycle and represent the amount of product amplified to that point in the amplification reaction. The point when the fluorescent signal is first recorded as statistically significant is the threshold cycle ($\Delta Ct$).

Thus, many of the RNA detection and quantification methods involve hybridization to a probe (e.g., probe(s) or primer(s) selected from a segment of a nucleic acid encoding androgen variant v5,6,7 or androgen variant v7). Nucleic acid hybridization involves contacting a probe and target nucleic acid under conditions where the probe and its complementary target can form stable hybrid duplexes through complementary base pairing (see Lockhart et al., 1999, WO 99/32660, for example). The target of hybridization is an androgen receptor mRNA, such as a wild type, androgen receptor mRNA, an androgen variant v5,6,7 mRNA, an androgen variant v7, or a combination thereof. The nucleic acids that do not form hybrid duplexes during hybridization are washed away during a washing step, leaving the hybridized nucleic acids to be detected, for example, through detection of a label that intercalates into the hybrid or that is attached to the probe or primer. It is generally recognized that nucleic acids are denatured by increasing the temperature and/or decreasing the salt concentration of the buffer containing the nucleic acids.

Under low stringency conditions (e.g., low temperature and/or high salt) hybrid duplexes (e.g., DNA-DNA, RNA-RNA or RNA-DNA) will form even where the annealed sequences are not perfectly complementary. Thus specificity of hybridization is reduced at lower stringency. Conversely, at higher stringency (e.g., higher temperature or lower salt) successful hybridization occurs with fewer mismatches.

One of skill in the art will appreciate that hybridization conditions may be selected to provide any degree of stringency. Stringency can also be increased by addition of agents such as formamide. Hybridization specificity may be evaluated by comparison of hybridization to the test probes with hybridization to the various controls that can be present (e.g., expression level control, normalization control, mismatch controls, etc.). For example, one control can be a normalization control such as a housekeeping gene. Examples of controls for normalization of expression include expression of 18S rRNA, actin, or GAPDH.

In general, there is a tradeoff between hybridization specificity (stringency) and signal intensity. Thus, in some embodiments, the wash is performed at the highest stringency that produces consistent results and that provides a signal intensity greater than approximately 10% of the background intensity. To better distinguish between the signal and the background, the hybridized sequences (e.g., on a microarray) may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al. (1989); Nucleic Acid Hybridization, A Practical Approach, IRL Press, Washington D.C. 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed. In general, the stringency of hybridization is determined by the wash step. Hence, a wash step involving 0.1×SSPE, 1.0% SDS at a temperature of at least 42° C. can yield a high stringency hybridization product. In some instances the high stringency hybridization conditions include a wash in 1×SSPE, 1.0% SDS at a temperature of at least 50° C., or at about 65° C.

"Medium stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed. Hence, a wash step involving 1.0×SSPE, 1.0% SDS at a temperature of 42° C. can yield a medium stringency hybridization product.

"Low stringency conditions" include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed. Hence, a wash step involving 5×SSPE, 1.0% SDS at a temperature of 42° C. can yield low stringency hybridization product.

Expression levels can also be determined at the protein level, for example, using various types of immunoassays or proteomics techniques.

In immunoassays, the target diagnostic protein marker (e.g., ARv5,6,7 and/or ARv7) is detected by using an binding entity or antibody that specifically binds to the marker(s). The antibody can be labeled with a detectable moiety. Numerous labels are available which can be generally grouped into the following categories. A variety of immunoassay procedures can be employed such as a cell sorting assay (where cells are labeled with a selected binding entity or antibody), sandwich immunoassay, competition inhibition immunoassay, ELISA (Enzyme-Linked Immunosorbent Assay), agglutination assay, precipitation assay, radioimmunoassay or antigen-down immunoassay or immunometric assay.

Fluorescent labels such as rare earth chelates (europium chelates) or fluorescein and its derivatives, rhodamine and its derivatives, dansyl. Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

The antibody can be labeled with the radioisotope such as $^{35}S$, $^{14}C$, $^{125}I$, $^{3}H$, and $^{131}I$, using the techniques described in Current Protocols in Immunology, Volumes 1 and 2, Coligen et al. (1991) Ed. Wiley-Interscience, New York, N.Y., Pubs, for example, and radioactivity can be measured using scintillation counting.

Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are available in the art. The chemiluminescent substrate becomes electronically excited by a chemical reaction and may then emit light which can be measured (using a chemiluminometer, for example) or donates energy to a fluorescent acceptor.

Examples of enzymatic labels include luciferases (e.g., firefly Luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases {e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) Methods for the Preparation of Enzyme-Antibody Conjugates for use in Enzyme Immunoassay, in Methods in Enzymol. (eds. J. Langone & H. Van Vunakis), Academic press, New York 73: 147-166.

Examples of enzyme-substrate combinations include, for example: horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and β-D-galactosidase (β-O-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In other versions of immunoassay techniques, the antibody need not be labeled, and the presence thereof can be detected using a labeled antibody which binds to the antibody. Thus, the diagnostic immunoassays herein may be in any assay format, including, for example, competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyze is bound by a first antibody which is immobilized on a solid support, and thereafter a second antibody binds to the analyze, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Protein levels can also be detected using proteomics techniques. The term "proteome" refers to the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-dimensional gel electrophoresis (e.g., 2-D PAGE); (2) identification of the individual proteins within or recovered from the gel, e.g. immunoblotting, by mass spectrometry, or N-terminal sequencing, and (3) analysis of the data using bioinformatics. Proteomics methods are valuable alternatives or supplements to other methods of gene expression profiling, and can be used, alone or in combination with other methods, to detect the products of the tumor resistance markers of the present invention.

Measurement of biomarker expression levels can be performed by using a software program executed by a suitable processor. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware by available procedures.

Following the measurement of the expression levels of the genes identified herein, or their expression products, and the determination that a subject is likely or not likely to respond to treatment with taxane, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

A diagnosis, prediction and/or treatment recommendation based on the expression of a particular marker (e.g., ARv5, 6,7 or ARv7), or upon the level of a marker in a test subject is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, electronic forms of communication, such as email, or telephone.

In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system.

The taxane sensitivity of a patient, and the expression of an androgen receptor variant, can also be detected by whether genes normally regulated by wild type androgen receptor are normally expressed. For example, the following genes normally interact with androgen receptors: AKT1, BAG1, Beta-catenin, BRCA1, C-jun, Calmodulin 1, Caveolin 1, CDK9, COX5B, CREB-binding protein, Cyclin D1, Cyclin-dependent kinase 7, Death associated protein 6, Deleted in Colorectal Cancer, EFCAB6, Epidermal growth factor receptor, FOXO1, GAPDH, Gelsolin, GNB2L1, GSK3B, HDAC1, HSP90AA1, HTATIP, MAGEA11, MED1, MYST2, NCOA1, NCOA2, NCOA3, NCOA4, NCOA6, NCOR2, NONO, PA2G4, PAK6, PATZ1, PIAS2, PRPF6, PTEN, RAD9A, RANBP9, RCHY1, Retinoblastoma protein, RNF14, RNF4, SART3, SMAD3, Small heterodimer partner, Src, SRY, STAT3, SVIL, Testicular receptor 2, Testicular receptor 4, TGFB1I1, TMF1, TRIM68, UBE2I, UXT, ZMIZ1, and any combination thereof. These genes are referred to herein as "androgen receptor regulated genes." When an androgen receptor variant (e.g., ARv5,6,7 or Arv7) is expressed instead of, or in addition to, the wild type androgen receptor, the expression of these androgen receptor regulated genes is altered. Thus, the expression of an androgen receptor variant (e.g., ARv5,6,7 or Arv7) can be detected by detecting alternations in the expression of one or more androgen receptor-related genes in a test sample relative to expression levels of these androgen receptor-related genes in a wild type, healthy sample of cells.

Capture and Detection of Markers in Circulating Tumor Cells

The development of metastases in patients with solid tumor malignancies can result from tumor cells entering the circulatory system and migrating to distant organs, where they extravasate and multiply. Circulating tumor cells (CTCs) are rare—as few as one cell per 100 million blood cells.

A variety of technologies has been developed to improve the detection and capture of circulating tumor cells from the peripheral blood. These include density gradient centrifugation, immunomagnetic bead separation using monoclonal antibodies targeting epithelial cell-surface antigens, cell sorting using flow cytometry, filtration based size separation and microfluidic devices. Although advances in circulating tumor cell capture have been made, the low frequency of circulating tumor cells in cancer patients, their heterogeneity, the lack of organ-specific capture approaches, and the plasticity of the circulating tumor cell population has limited the ability to capture and track all circulating tumor cells. Currently, the epithelial cell-adhesion molecule (EpCAM), represents an antigen of choice for the majority of microfluidic devices that have been developed to capture circulating tumor cells.

However, accumulating evidence indicates that the expression of EpCAM during cancer progression and, in particular, during epithelial-to-mesenchymal transition has not been well characterized, raising concerns about the universality of this antigen for immunocapture systems (Mani et al., Cell 133: 704-715 (2008); Polyak & Weinberg, Nature reviews Cancer 9: 265-273 (2009)). EpCAM has been reported to have oncogenic potential and its presence can correlate with proliferation in cell lines. However, it is down-regulated during epithelial-to-mesenchymal transition, and epithelial-to-mesenchymal transition markers have been shown to be more important than epithelial markers (e.g., cytokeratin) in predicting cancer progression (Gradilone et al., J. Cell. Molec. Med. 15: 1066-1070 (2011)). Thus, while EpCAM is clearly useful in identifying circulating tumor cell populations in many cancers, the biases associated with EpCAM enrichment are currently unknown.

In addition to the uncertainties regarding surface antigens, the specificity of immunocapture from the blood is confounded by the non-specific adhesive properties of leukocytes on most antibody surfaces. Because of the presence of numerous leukocytes in blood at an approximately $10^4$-$10^5$:1 ratio with respect to the circulating tumor cells, immunospecific surfaces enrich circulating tumor cells but cannot isolate them from contaminating leukocytes entirely. Identifying circulating tumor cells requires additional steps and often involves staining with DAPI to ensure the presence of an intact nucleus and immunostaining to identify the presence of epithelial markers (i.e., cytokeratin) and the lack of the leukocytic marker CD45. Such immunostaining has identified a family of criteria that correlate circulating tumor cell number with patient prognosis (Coumans et al., J. Eur. Soc. Med. Oncol. 21: 1851-57 (2010), but these criteria are based upon fixation and staining procedures for circulating tumor cell identification, as in the commercial CellSearch® system (Danila et al., Clin. Cancer Res. 13:7053-58 (2007; Scher et al., The Lancet Oncol. 10: 233-239 (2009)). Although enumeration of circulating tumor cells from patients with advanced prostate cancer receiving chemotherapy using the commercially available circulating tumor cell capture system by CellSearch® can be useful as a prognostic indicator of patient survival, the presence of contaminating leukocytes impede the downstream utility of circulating tumor cell capture devices, in that assays based on RNA or protein quantification are obfuscated by the need for fixation and material of leukocytic origin.

To facilitate high-efficiency capture of prostate circulating tumor cells, a microfluidic device is described herein that employs an approach termed 'geometrically enhanced differential immunocapture' (GEDI). This device combines a geometry that reduces capture of contaminating leukocytes by generating size-dependent cell-wall collisions. This geometric approach is combined with a prostate-specific immunocapture surface using the J591 monoclonal antibody that recognizes the extracellular domain of prostate-specific membrane antigen (PSMA) (Gleghorn et al., Lab on a Chip 10: 27-29 (2010)).

The microfluidic device includes a solid support with a length and width, and with rows of posts configured for flow of a cell sample through the length of the device from a cell sample application area, to an outlet; wherein each row is perpendicular to the length of the device; and where the posts of one row do not align with the posts of adjacent rows.

The microfluidic device can have a cover sheet on top of the posts, so that each post is linked to the solid support and the cover sheet. Thus, when sample is introduced through the cell sample application area, the sample flow is constrained to channels between the posts, and does not flow on top or below the posts.

The posts of one row do not align with the posts of one or two adjacent rows because the posts of one row are offset across the width of the device, relative to posts in the one or two adjacent rows by 0.1 to 100 microns. The term "offset" when used to describe the position of posts in a row relative to the one or two adjacent rows, means that a line drawn from each post in the row to its nearest neighbor in the one or two adjacent rows is not parallel to the length of the device. Instead, each post in a row is shifted (offset) along the width of the device, relative to its nearest neighbor in the one or two adjacent rows. The offset can be about 0.1 to 100 microns, or about 0.2 to 75 microns, or about 0.5 to 50 microns, or about 0.75 to 10 microns, or about 1 microns to about 25 microns.

The solid support and/or the cover sheet can include silicon, silica, glass, polydimethylsiloxane (PDMA), cellulose, ethylcellulose, methylcellulose, nitrocellulose, hydroxypropylcellulose, hydroxypropyl methylcellulose, polystyrene, polyethylene, nylon, rayon, cotton, Teflon, mica, sephadex, sepharose, polyacrylonitrile, glass, glass-fiber paper, gold, metal, paper, and combinations thereof. In some embodiments, the solid support is silicon, glass, metal (e.g., gold or gold plated), or a combination thereof. The cover sheet can, for example, be polydimethylsiloxane (PDMA), polystyrene, polyethylene, nylon, rayon, Teflon, mica, glass.

The device can include one or more types of binding entities immobilized to at least one section of the solid support and/or the cover sheet of the device. The binding entities can be specific for the cell type of interest. For example, the binding entities can selectively bind to circulating tumor cells. In some embodiments, the binding entities can be an anti-PMSA antibody. For example, the binding entity can be the monoclonal antibody J591 developed at Weill Cornell Medical College. PSMA is a cell surface peptidase highly expressed by malignant prostate epithelial cells. PSMA is an attractive target for prostate cancer circulating tumor cell capture, as it is expressed on virtually all prostate cancer cells and expression increases following castration.

The Examples further describe the utility of the GEDI device, including a comparison of circulating tumor cell enumeration with CellSearch®, the detection of a specific androgen receptor mutation from blood samples spiked with only 50 cells; the identification of the TMPRSS2-ERG fusion by immunostaining, and the ex-vivo assessment of circulating tumor cell sensitivity to taxane-treatment using microtubule bundling as a marker of drug-target engagement.

Circulating tumor cells are typically large, nucleated, PSMA$^+$/CD45$^-$ cells. Enumeration and analysis of circulating tumor cells optimally focuses on intact cells that fulfill such circulating tumor cell criteria while ignoring cell fragments, and non-nucleated cells that might qualify as circulating tumor cells (despite a recent report suggesting that enumeration of such events can impact the prognostic value of the circulating tumor cell assay (Coumans et al., Annals of Oncology: official journal of the European Society for Medical Oncology/ESMO 21: 1851-1857 (2010)). A microfluidic device such as the device described herein can be used to provide substantially pure, intact circulating tumor cells for determining whether an androgen receptor splice variant (e.g., one with SEQ ID NO:3 or 5) is expressed in patient test samples that contain circulating tumor cells.

When circulating tumor cells are captured by the device, the cells can be evaluated by any of the methods and assays described herein, either while the captured cells are within the device or after removal of the captured cells from the device.

Binding Entities

As used herein, "binding entities" include any molecule that can specifically bind to an androgen receptor or an androgen receptor splice variant. Each binding entity binds a its target androgen receptor or splice variant with specificity. Binding entities are typically binding regions of affinity molecules available in the biological sciences including, but not limited to, antibodies, antibody fragments, leucine zippers, histones, complementary determining regions (CDRs), single chain variable fragments (scFv's), receptors, ligands, aptamers, lectins, nucleic acid probes and the like. Binding entities can include binding regions that are generated, for example, of full sized versions of an affinity molecule, fragments of an affinity molecule, or the smallest portion of the affinity molecule providing binding that is useful in the detection of a target of interest (an androgen receptor or an androgen receptor splice variant).

In a one embodiment, the devices include binding entities which are members of the immunoglobulin family of proteins, or derivatives thereof. For example, the binding entity can be a complete immunoglobulin or antibody, a fragment, a single chain variable fragment (scFv), a heavy or light chain variable region, a CDR peptide sequence, and/or the like.

As used herein, "antibody" refers to an immunoglobulin molecule, and fragments thereof, which are immunologically reactive with a particular antigen. The term "antibodies" refers to a plurality of such molecules and is not limited to homogeneous populations of a single type of antibody. The term "antibody" also includes genetically engineered forms such as chimeric antibodies, heteroconjugate antibodies (e.g., bispecific antibodies), and recombinant single chain Fv fragments (scFv), and disulfide stabilized (dsFv) Fv fragments (see, for example U.S. Pat. No. 5,747,654). The term "antibody" also includes antigen binding forms of antibodies (e.g., Fab', F(ab')2, Fab, Fv and IgG. See also, Pierce Catalog and Handbook, 1994-1995 (Pierce Chemical Co., Rockford, Ill.). The term "antibody," includes immunologically-active fragment of an immunoglobulin molecule such as the Fab or F(ab')2 fragment generated by, for example, cleavage of the antibody with an enzyme such as pepsin or co-expression of an antibody light chain and an antibody heavy chain in bacteria, yeast, insect cell or mammalian cell. The antibody can also be an IgG, IgD, IgA, IgE or IgM antibody.

Antibodies for use in the methods and devices described herein can be obtained commercially or can be generated by available methods. Methods of making antibody fragments are available in the art (see for example, Harlow and Lane, *Antibodies: A Laboratory Manual*, Cold Spring Harbor Laboratory, New York, (1988), specifically incorporated herein by reference in its entirety). For example, antibodies suitable for use the devices can be obtained by immunizing an animal such as a rabbit, goat, sheep, horse, or guinea pig. Such antibodies are present in the blood (e.g., serum) of immunized animals.

Antibody fragments can be prepared by proteolytic hydrolysis of the antibody or by expression of nucleic acids encoding the antibody fragment in a suitable host. Antibody fragments can be obtained by pepsin or papain digestion of whole antibodies conventional methods. For example, antibody fragments can be produced by enzymatic cleavage of antibodies with pepsin to provide a 5S fragment described as F(ab')$_2$. This fragment can be further cleaved using a thiol reducing agent, and optionally using a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated herein by reference in their entireties.

A number of proteins can serve as protein scaffolds to which binding domains can be attached and thereby form a suitable binding entity. The binding domains bind or interact with androgen receptors while the protein scaffold merely holds and stabilizes the binding domains so that they can bind. A number of protein scaffolds can be used. For example, phage capsid proteins can be used. See Review in Clackson & Wells, Trends Biotechnol. 12:173-184 (1994). Phage capsid proteins have been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of Streptococcus (O'Neil et al., Techniques in Protein Chemistry V (Crabb, L., ed.) pp. 517-524, Academic Press, San Diego (1994)). These scaffolds have displayed a single randomized loop or region that can be modified to include binding domains for androgen receptor or an androgen receptor splice variants.

Fibronectin type III domain has also been used as a protein scaffold to serve as a binding entity platform. Fibronectin type III is part of a large subfamily (Fn3 family or s-type Ig family) of the immunoglobulin superfamily. Sequences, vectors and cloning procedures for using such a fibronectin type III domain as a protein scaffold portion of a binding entity (e.g. that includes CDR peptides) are provided, for example, in U.S. Patent Application Publication 20020019517. See also, Bork, P. & Doolittle, R. F. (1992) Proposed acquisition of an animal protein domain by bacteria. Proc. Natl. Acad. Sci. USA 89, 8990-8994; Jones, E. Y. (1993) The immunoglobulin superfamily Curr. Opinion Struct. Biol. 3, 846-852; Bork, P., Horn, L. & Sander, C. (1994) The immunoglobulin fold. Structural classification, sequence patterns and common core. J. Mol. Biol. 242, 309-320; Campbell, I. D. & Spitzfaden, C. (1994) Building proteins with fibronectin type III modules Structure 2, 233-337; Harpez, Y. & Chothia, C. (1994).

It can be useful to employ a binding entity that binds to a selected androgen receptor or androgen receptor splice variant with specificity. For example, the binding entity can have an affinity for an androgen receptor or an androgen receptor splice variant of about 1×10$^7$ M$^{-1}$ to about 1×10$^{10}$ M$^{-1}$, or about 1×10$^8$ M$^{-1}$ to about 1×10$^9$ M$^{-1}$. For example, the affinity of a binding entity can be measured by detecting and quantifying the formation of a binding entity-androgen receptor complex, generally referred to as an antigen-antibody complex [Ag-Ab]. The formation of such an antigen-antibody complex [Ag-Ab] is illustrated by the following reaction.

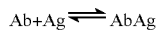

The formation of such an Ag-Ab complex is therefore at equilibrium with its dissociation, and the equilibrium association constant ($K_A$) of the complex can be calculated as follows:

$K_A = 1/k_d = [Ag\text{-}Ab]/[Ag][Ab]$

As used herein, the term "binds specifically" or "specifically binds," in reference to a binding entity or antibody interaction with an androgen receptor or androgen receptor variant protein, means that the binding entity or antibody binds with a particular antigen (e.g., androgen receptor splice variant v5,6,7, such as one with SEQ ID NO:3, or androgen receptor splice variant v7, such as one with SEQ ID NO:5) without substantially binding to a full-length androgen receptor or other androgen receptor isoform.

For example, in some embodiments, selected binding entities can bind with greater affinity or selectivity to androgen receptor splice variant v5,6,7 (such as one with SEQ ID NO:3) than to full-length androgen receptor, or the androgen receptor splice variant v7. Thus, for example, a binding entity binds to androgen receptor splice variant v5,6,7 (such as one with SEQ ID NO:3) with at least 50% or greater affinity (or selectivity), or 60% greater affinity (or selectivity), or 70% greater affinity (or selectivity), or 80% greater affinity (or selectivity), or 85% greater affinity (or selectivity), or 90% greater affinity (or selectivity), or 95% greater affinity (or selectivity) for androgen receptor splice variant v5,6,7 (such as one with SEQ ID NO:3) than to full-length androgen receptor or to other androgen receptor isoforms. Similarly, for example, a binding entity binds to androgen receptor splice variant v7 (such as one with SEQ ID NO:5) with at least 50% or greater affinity (or selectivity), or 60% greater affinity (or selectivity), or 70% greater affinity (or selectivity), or 80% greater affinity (or selectivity), or 85% greater affinity (or selectivity), or 90% greater affinity (or selectivity), or 95% greater affinity (or selectivity) for androgen receptor splice variant v7 (such as one with SEQ ID NO:5) than to full-length androgen receptor or to other androgen receptor isoforms.

Binding entities can be separated from impurities before incorporation into the devices. For example, the binding entities can be purified or isolated using purification methods such as electrophoretic, molecular, immunological and chromatographic techniques, including ion exchange, hydrophobic, affinity, and reverse-phase HPLC chromatography, and chromatofocusing, and the like. The degree of purification necessary will vary depending on the contaminants present with the binding entities. In some instances no purification will be necessary (e.g., when binding entities are commercially available and provided in purified form).

Antibodies directed against androgen receptor splice variants (such as ARv5,6,7, e.g., with SEQ ID NO:3; or ARv7, e.g., with SEQ ID NO:5) are generally monoclonal antibodies.

A monoclonal antibody is a population of molecules having a common antigen binding site that binds specifically with a particular antigenic epitope. A monoclonal antibody can be obtained by selecting an antibody-producing cell from a mammal that has been immunized with a selected androgen receptor splice variant (such as ARv5,6,7, e.g., with SEQ ID NO:3; or ARv7, e.g., with SEQ ID NO:5) and fusing the antibody-producing cell, e.g. a B cell, with a myeloma to generate an antibody-producing hybridoma. A monoclonal antibody can also be obtained by screening a recombinant combinatorial library such as an antibody phage display library. See, for example, PHAGE DISPLAY—A LABORATORY MANUAL, Barbas, et al., eds.

Cold Spring Harbor Laboratory Press, Cold Spring Harbor, N.Y., 2001; and Kontermann & Dübel, ANTIBODY ENGINEERING, Heidelberg: Springer-Verlag. Berlin, 2001. Techniques for preparing monoclonal antibody-secreting hybridoma cells are also described, for example, by Kohler and Milstein, Nature 256:495-97 (1975) and Kozbor et al. Immunol Today 4: 72 (1983).

A monoclonal antibody against androgen receptor splice variant v5,6,7 or androgen receptor splice variant v7 can also be prepared using other methods available in the art. For example, the antibodies can be obtained by screening of a recombinant combinatorial immunoglobulin library using a selected androgen receptor splice variant protein (such as ARv5,6,7, e.g., with SEQ ID NO:3; or ARv7, e.g., with SEQ ID NO:5). Immunoglobulins that selectively bind to a selected androgen receptor protein can be produced by recombinant expression from cells encoding the immunoglobulin of interest.

The antibodies can be evaluated for affinity to a selected androgen receptor splice variant (such as ARv5,6,7, e.g., with SEQ ID NO:3; or ARv7, e.g., with SEQ ID NO:5) using standard procedures including, for example, enzyme linked immunosorbent assay (ELISA) to determine antibody titer and protein A chromatography to obtain the antibody-containing an IgG fraction.

Another method for generating antibodies involves a Selected Lymphocyte Antibody Method (SLAM). The SLAM technology permits the generation, isolation and manipulation of monoclonal antibodies without needing to generate a hybridoma. The methodology principally involves the growth of antibody forming cells, the physical selection of specifically selected antibody forming cells, the isolation of the genes encoding the antibody and the subsequent cloning and expression of those genes.

The nucleic acids encoding the antibodies can be mutated to optimize the affinity, selectivity, binding strength or other desirable property of an antibody. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

Labels

A variety of different labels can be used in the methods, kits, and devices described herein. Labels can be covalently attached to any of the binding entities, primers or probes described herein. Alternatively, the labels can non-covalently associate with a hybridized probe or primer that is specifically bound to a target nucleic acid (e.g., an mRNA encoding an androgen receptor or androgen receptor variant protein). Similarly, a label can be non-covalently or indirectly bound to a binding entity. For example, the label can be an enzyme substrate that is transformed by an enzyme bound to a binding entity into a colored signal.

So called "direct labels" are detectable labels that are directly attached to or incorporated into a binding entity that then can bind to an androgen receptor or androgen receptor variant. In contrast, so-called "indirect labels" are joined to a complex formed between an androgen receptor or androgen receptor variant, and a binding entity after complex formation. For example, an indirect label can be attached to a secondary antibody that binds to a different epitope on an androgen receptor or androgen receptor variant, than does a primary antibody.

Examples of labels include, but not limited to, fluorophores, chromophores, radiophores, enzymatic tags, antibodies, chemiluminescence, electroluminescence, and affinity labels. One of skill in the art will recognize that these and other labels can be used with success in this invention. Examples of enzyme labels include enzymes such as urease, alkaline phosphatase or peroxidase to mention a few. Colorimetric indicator substrates can be employed to provide a detection means visible to the human eye or spectrophotometrically. Examples of fluorophores include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Means of detecting such labels are well known to those of skill in the art. For example, fluorescent markers may be detected using a microscope, photodetector or fluorimeter to detect emitted light. In still further examples, enzymatic labels can be detected by providing the enzyme with a substrate and detecting the reaction product produced by the action of the enzyme on the substrate, and colorimetric labels are detected by simply visualizing the colored label or reaction product; or by use of spectrometer.

Taxanes

A variety of taxanes can be used in the methods, devices and compositions described herein.

Taxanes refer to a class of compounds having a core ring system of three rings, A, B and C, as shown below.

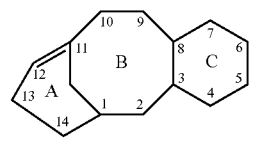

Examples of taxanes that can be used in the methods, devices and compositions described herein include paclitaxel, docetaxel, cabazitaxel, baccatin III, 10-deacetylbaccatin, hongdoushan A, hongdoushan B, hongdoushan C, and combinations thereof. In some instances, the taxane is paclitaxel, docetaxel, or a combination thereof.

Kits

Kits are also described here for use in the diagnostic and therapeutic applications described or suggested above. The kits can include a carrier means for the devices and reagents as well as other components of the kits. Such a carrier can be a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can separately contain, for example, one or nucleic acid probes, one or more binding entities, one or more devices, as well as positive and/or negative control samples or solutions.

For example, at least one of the containers can include at least one binding entity that binds with specificity or selectivity to an androgen receptor or androgen receptor variant protein. In another embodiment, one of the containers can include a nucleic acid probe or primer that selectively hybridizes to an androgen receptor or androgen receptor variant mRNA. The binding entities, probes and primers are or can be detectably labeled. For example, the binding entities, probes and primers can be packaged separately from the labels, and the label can be added to the binding entities, probes and primers during or after performance of an assay for an androgen receptor or androgen receptor variant.

Kits can also contain vials, needles, syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing biological samples. Kits may also optionally contain implements useful for introducing samples into an assay chamber or a cell capturing device, including, for example, droppers, Dispo-pipettes, capillary tubes, rubber bulbs (e.g., for capillary tubes), and the like. Other components can also be present in the kits such as disposal means for discarding used devices and/or other items used with the device (such as patient samples, etc.). Such disposal means can include, without limitation, containers that are capable of containing leakage from discarded materials, such as plastic, metal or other impermeable bags, boxes or containers.

The kits can include instructions for use of a cell capturing device, or for performing an assay such as an immunoassay, cell sorting assay, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, in situ hybridization, nucleic acid amplification, reverse transcription, polymerase chain reaction, quantitative real time polymerase chain reaction (qRT-PCR), and the like.

The following non-limiting Examples illustrate some of the experimental work involved in developing the invention.

Example 1

Materials and Methods

This Example describes some of the materials and methods employed in the development of the invention.
Device Fabrication All device fabrication was carried out at the Cornell NanoScale Science and Technology Facility (Ithaca, N.Y.). Standard photolithography techniques were used to define array geometries on silicon wafers. The wafers were etched with an oxygen plasma deep reactive ion etcher (Uniaxis SLR770) to a depth of 100 μm, and cleaned using sulfuric acid and hydrogen peroxide prior to antibody surface functionalization. The J591 monoclonal antibody (manufactured by Lonza plc (Slough, England) for BZL Biologics, Inc.) was immobilized on the device surfaces using MPTMS-GMBS-NeutrAvidin-biotin chemistry (Gleghorn et al., Lab on a chip 10: 27-29 (2010); see FIG. 1C). Polydimethylsiloxane (PDMS) sheets (5:1 base:curing agent), approximately 3 mm thick, were polymerized for 18 hours at 60° C. and trimmed to form covers for the GEDI device. A PDMS sheet was clamped to the top of the device with a custom jig to create closed channels populated with post arrays. Inlet and outlet holes were created with a biopsy punch, and 23-gauge metal tubes were inserted into the PDMS to connect inlet and outlets to external tubing. Devices were primed with a 50/50 isopropanol/water mixture, and then flushed with DI water and PBS before experiments.
Sample Collection and Microfluidic Capture Peripheral blood samples were collected in tubes containing sodium citrate anticoagulant (Becton-Dickinson) from healthy volunteers and patients with metastatic castrate-resistant prostate cancer under a clinical protocol entitled "Analysis of circulating tumor cells in prostate cancer. Predicting response to taxanes: a pilot study" which was approved by the Institutional Review Board (IRB) of Weill Cornell Medical College of Cornell University. Blood was obtained from patients or healthy donors following written informed consent, which was also approved by the IRB committee of Weill Cornell Medical College of Cornell University. As previously described by Gleghorn et al. (Lab on a chip 10: 27-29 (2010)), 1 ml of blood from each specimen was processed through the GEDI chip within 24 h of blood draw by pushing the blood through the device at a volumetric flow rate of 1 ml/hr (Chemyx syringe pump).
Cell Staining and Analysis The cell lines used in these experiments as controls for staining or in spiked experiments are: the human leukemia cell line U937, and the human prostate cancer cell lines PC-3, LNCaP and C4-2. All cell lines were purchased from ATCC. Post-capture, cells were fixed on-chip with PHEMO fixative at 37° C. (PHEMO buffer: PIPES acid, HEPES acid, EGTA disodium salt, Mg—Cl2-6H20, 10% DMSO), glutaraldehyde, and 3.7% formaldehyde. Cells were then blocked (10% Normal Goat Serum—Jackson Immuno Research) and immunostained with FITC-conjugated humanized mAb J591 to detect PSMA expression. Monoclonal mouse anti-CD-45 (BD Biosciences) followed by AlexaFluor568 labeled goat anti-mouse secondary (Invitrogen) and mouse anti-EpCAM directly conjugated to AlexaFluor647 (Biolegend). For the detection of intracellular antigens, cells were permeabilized with 0.1% Triton X-100 (Sigma-Aldrich) in PBS and stained by use of rat anti-alpha tubulin (YL1/2, Millipore) and rabbit anti-ERG monoclonal antibody (clone EPR 3864; Epitomics, Burlingame, Calif.). The anti-ERG antibody was a generous gift from Dr. Mark Rubin (Weill Cornell Medical College, New York, N.Y.). All primary antibodies were incubated for 1 hour at room temperature; secondary antibodies were stained at room temperature for 30 minutes. DAPI was used for DNA counterstaining. GEDI devices were mounted to coverslips with Mowiol and stored at −20° C. before analysis.
Circulating Tumor Cells Enumeration Blinded circulating tumor cell enumeration following antibody labeling was performed by use of a Zeiss LSM-700 point scanning confocal microscope, equipped with 405-, 488-, 555-, and 632-nm laser lines. All PSMA$^+$/CD45$^-$ nucleated cells were identified as circulating tumor cells. Initial validation of circulating tumor cell enumeration was accomplished by two independent, blinded testers. Positive and negative controls for antibody performance and staining were included in each experiment: U937 human leukemia cells (CD45$^+$/PSMA$^-$/EpCAM$^-$), and the human prostate cancer cell lines (C4-2 and LNCaP: PSMA$^+$/CD45−/EpCAM$^+$ and PC-3 (PSMA−/Cd45−/EpCAM dim). Individual z-stacks were acquired using 100×/NA 1.46 and 63×/NA 1.3 Plan-Apo Zeiss objectives controlled by Zen software (Zeiss) and presented as maximum intensity projections.

RNA Extraction

Following cell capture, the GEDI device was rinsed by flowing PBS for 30 min at a rate of 1 ml/hr. Cells were lysed with 700 µl of RLT Lysis buffer supplemented with 1% β-mercaptoethanol at a flow rate of 15 ml/hr. The lysate was collected, and RNA was extracted using the QiagenRNEasy Micro Plus Kit (Qiagen Inc, Valencia, Calif.) according to the manufacturer's instructions.

Ex-Vivo Drug Treatments and Analysis

For ex-vivo drug treatment experiments, the blood sample from each patient was divided and 1 ml was flown to each of three GEDI devices simultaneously. After circulating tumor cell capture and subsequent PBS wash, each GEDI microdevice was gently placed in a culture dish with RPMI-1640 media containing 2% serum and supplemented with either 0.1% DMSO control or paclitaxel at concentrations of 100 nM or 1 µM and incubated at 37° C. for 24 hr. At the end of treatment, the GEDI-captured cells were fixed with PHEMO buffer and processed for multiplex confocal microscopy following immunostaining with different cell surface and cytoplasmic antibodies as indicated. All circulating tumor cells ($PSMA^+/CD45-/DAPI^+$) were assessed for the presence of microtubule bundles as evidence of effective drug-target engagement. The percent of circulating tumor cells with evidence of microtubule bundling was calculated. In all samples analyzed, bundling was clearly apparent by the distinct shape, width, orientation and increased fluorescence intensity of microtubule bundles as compared with microtubules from untreated cells. In addition, DAPI counterstain was used to assess the presence of mitotic or apoptotic nuclei following drug treatment.

Statistical Analysis

Statistical analysis was performed to compare the mean circulating tumor cell counts obtained from castration-resistant prostate cancer patients and healthy donors. We used a non-parametric (Wilcoxon signed-rank) analysis, as circulating tumor cell counts did not exhibit normal distribution. Statistical significance was defined with $\alpha=0.05$.

Example 2

Cell Capturing Device

Figure 1C:
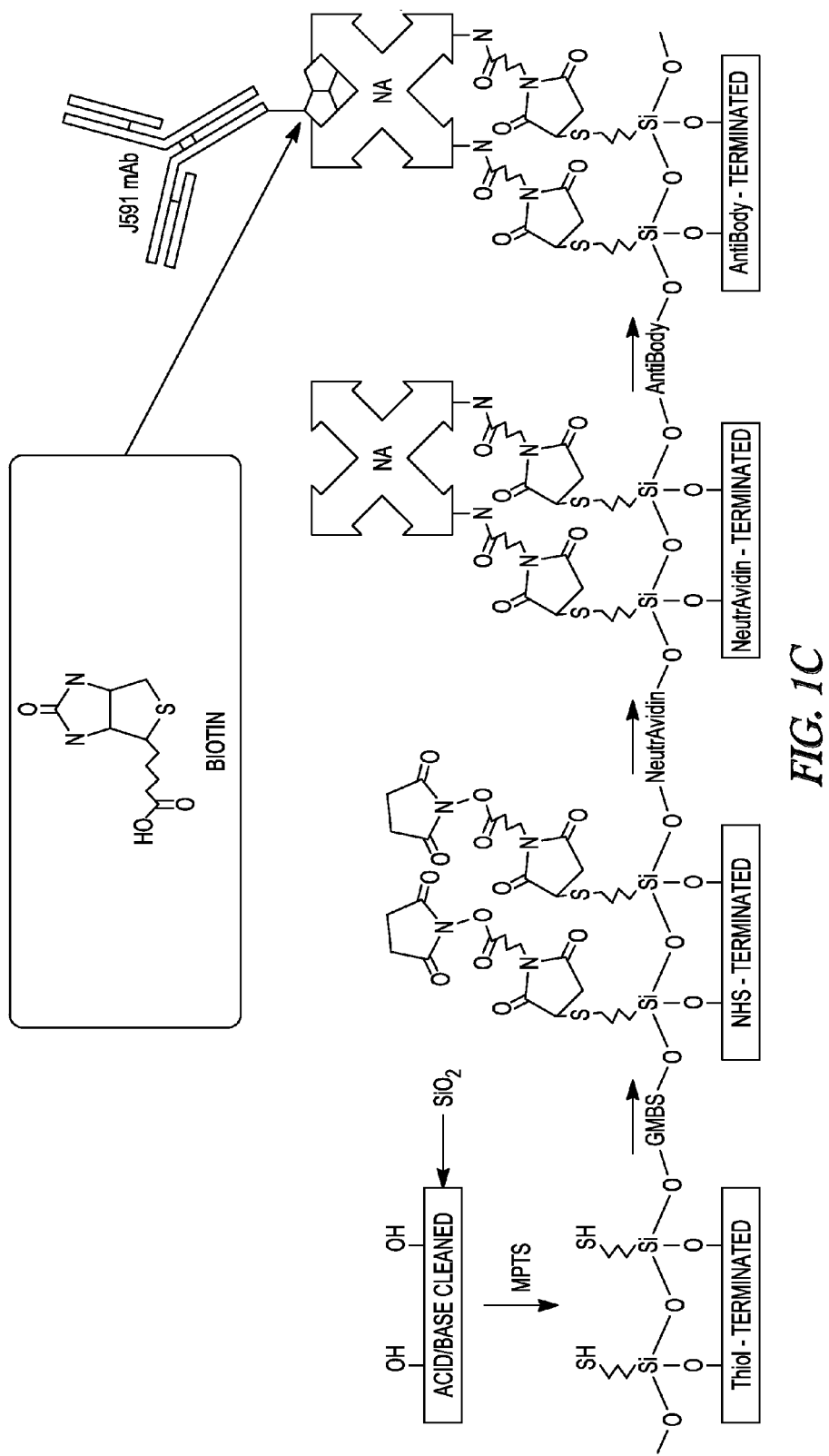
Figure 1D:
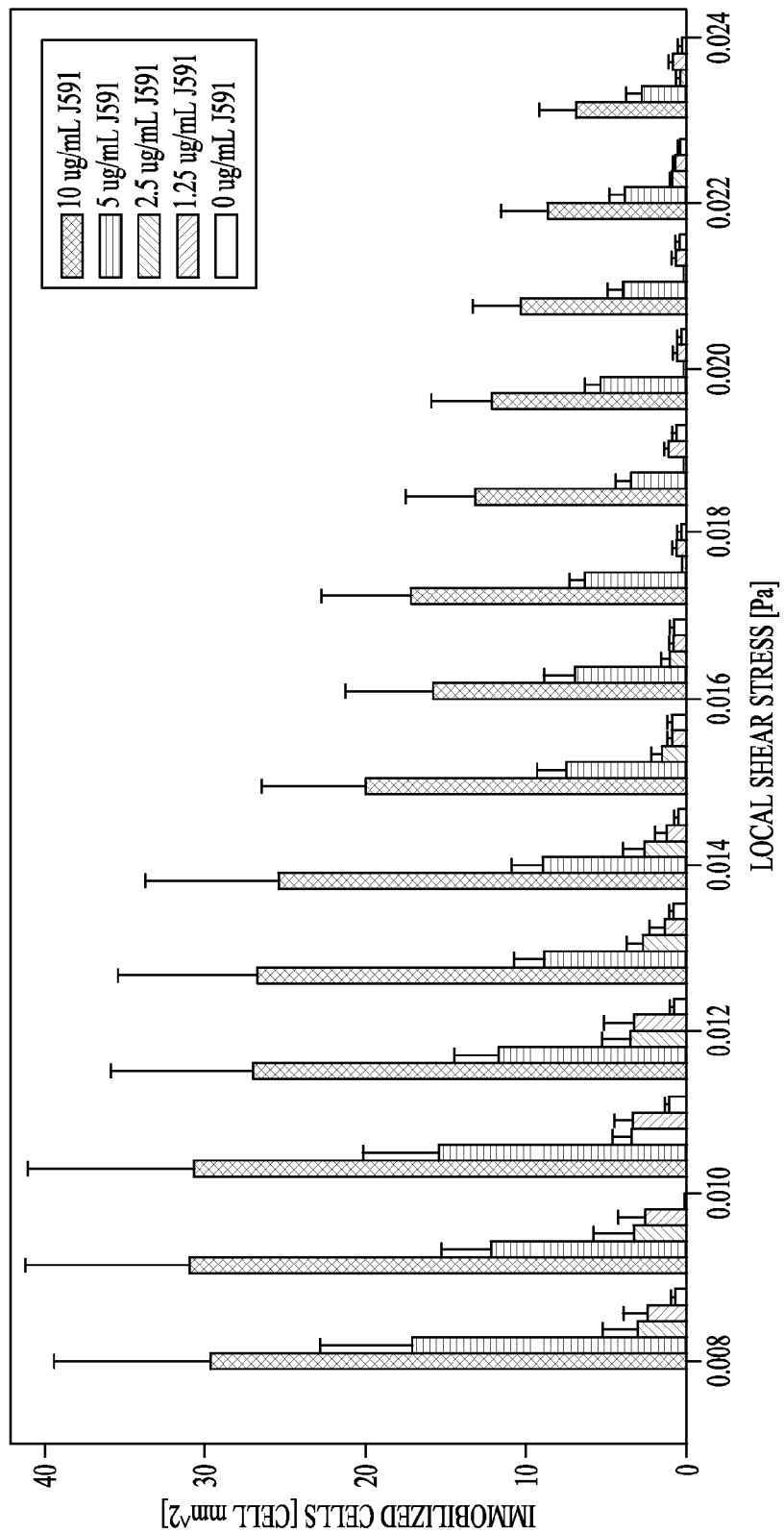

The cell capture rates of PSMA-positive cancer cells were determined to evaluate the performance of the device depicted in FIG. 1A. Cell capture was determined as a function of varying mAb J591 concentrations (1.5-20 ug/ml) using shear stress magnitudes representative of those experienced by the functionalized surfaces of the device (0.08-0.24 Pa). These experiments revealed a dose-dependent increase in cell capture up to mAb concentration of 10 ug/ml, which was used for all subsequent experiments (FIG. 1D).

Figure 2A:
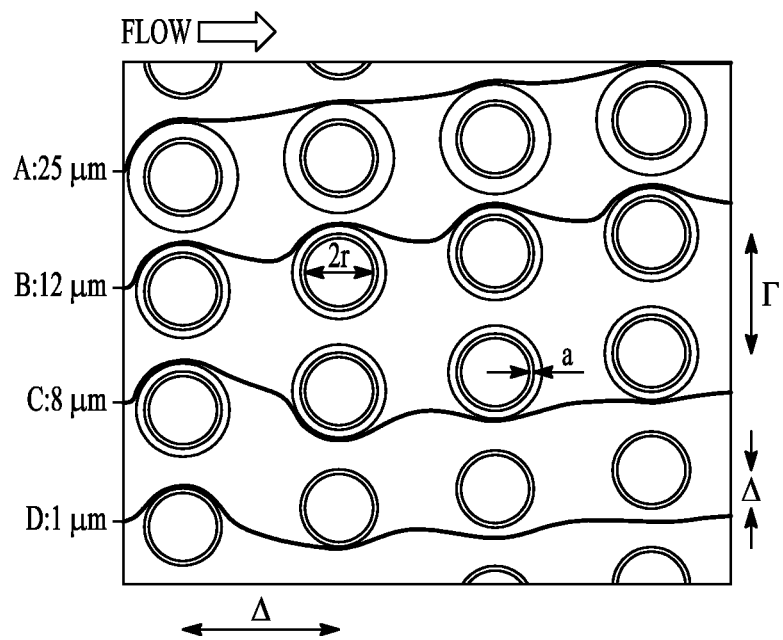
FIG. 2A-2F illustrate cell separation of differently sized cells by a straight-flow device versus non-linear flow pattern of the GEDI microfluidic device.
Figure 2B:
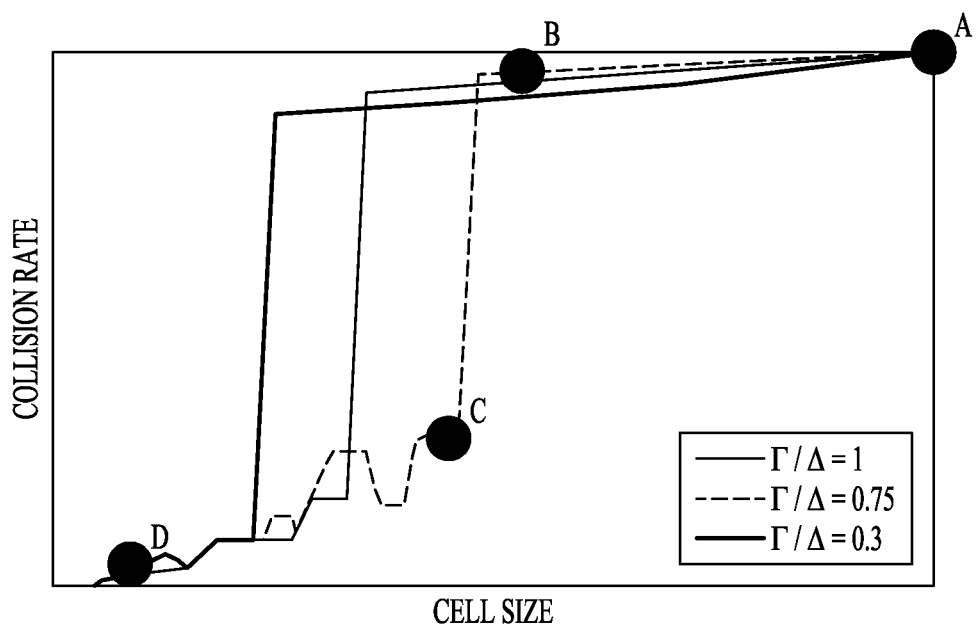

Although the J591 antibody is specific for PSMA-expressing cells, non-specific leukocyte adhesion has been a major problem for all blood-based immunocapture techniques. To minimize leukocyte adhesion, a parametric study was conducted to characterize collision rate (CpR; collision per row) as a function of cell size and obstacle offset. Collision rates from a subset of these offsets exhibit a sharp cutoff according to cell size, as shown in FIG. 2B. Hence an obstacle offset (7 µm) was selected that generates a sharp cutoff at the cell diameter of 14 µm. The physics describing this cutoff is illustrated by the size-dependent cell path lines (FIG. 2A), which show how large cells experience repeated collision whereas small cells separate from the obstacles and escape capture.

Figure 2C:
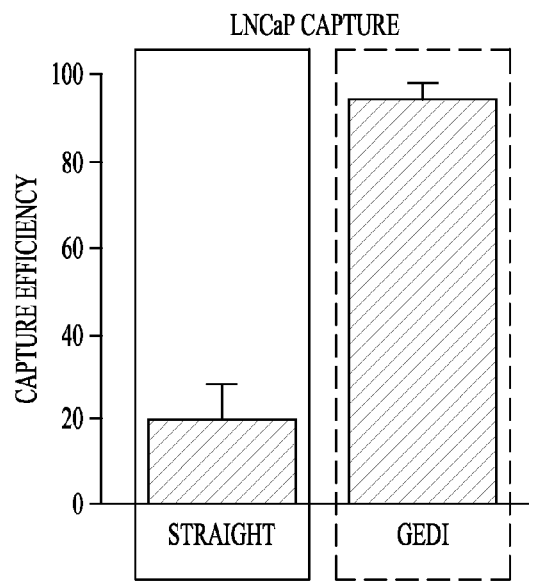
Figure 2D:
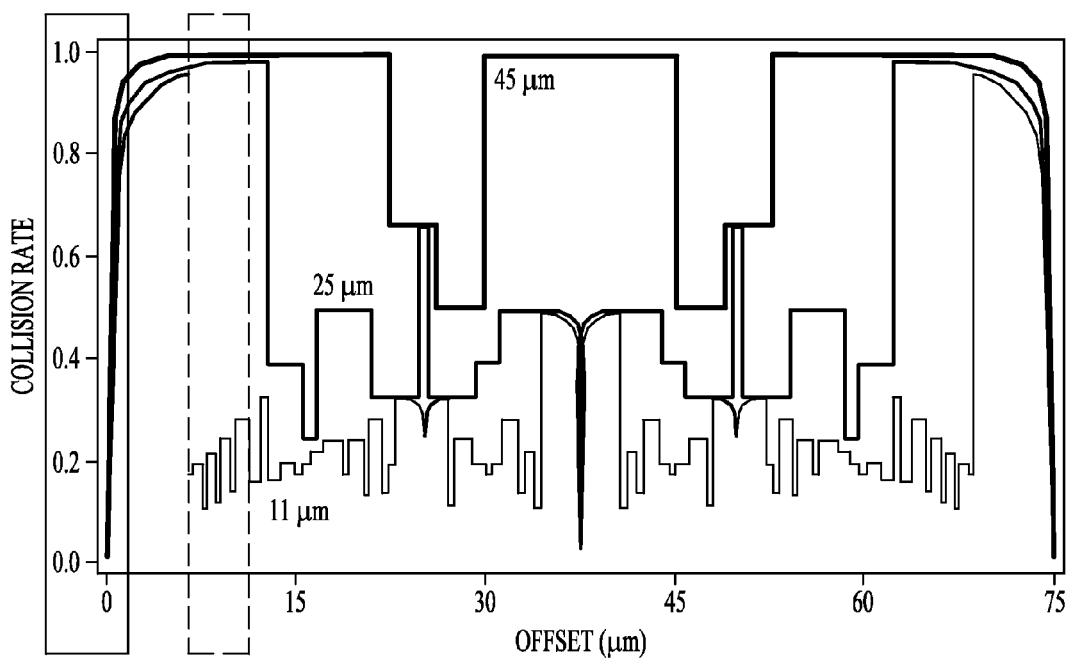

This hypothesis was then tested by measuring capture of LNCaP prostate cancer cells (FIG. 2C). In this experiment, spiked LNCaP cells were flown into J591-functionalized devices that had a 7 µm offset (GEDI) versus those that had no offset (straight). Although these two devices have the same surface-area-to-volume ratio, the GEDI geometry greatly increased cell capture efficiency, as measured by captured and enumerated cells normalized by input cell counts.

Figure 2E:
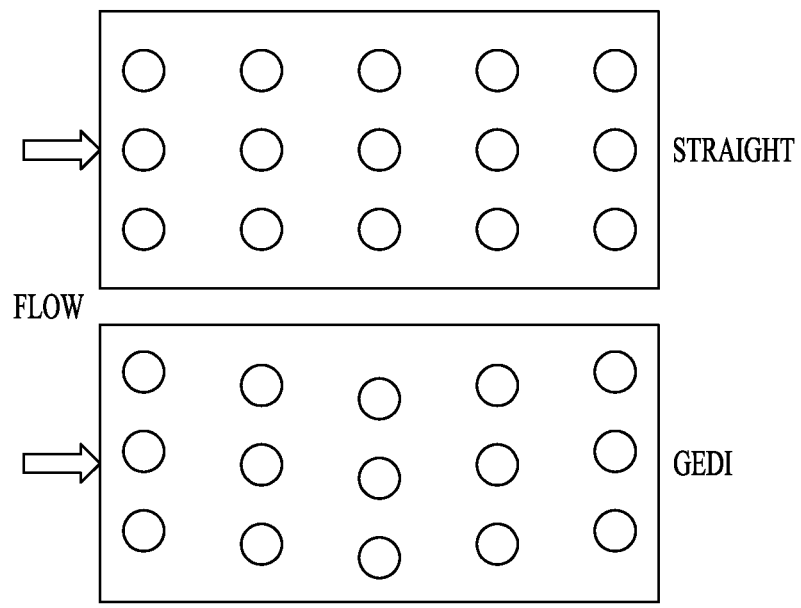
Figure 2F:
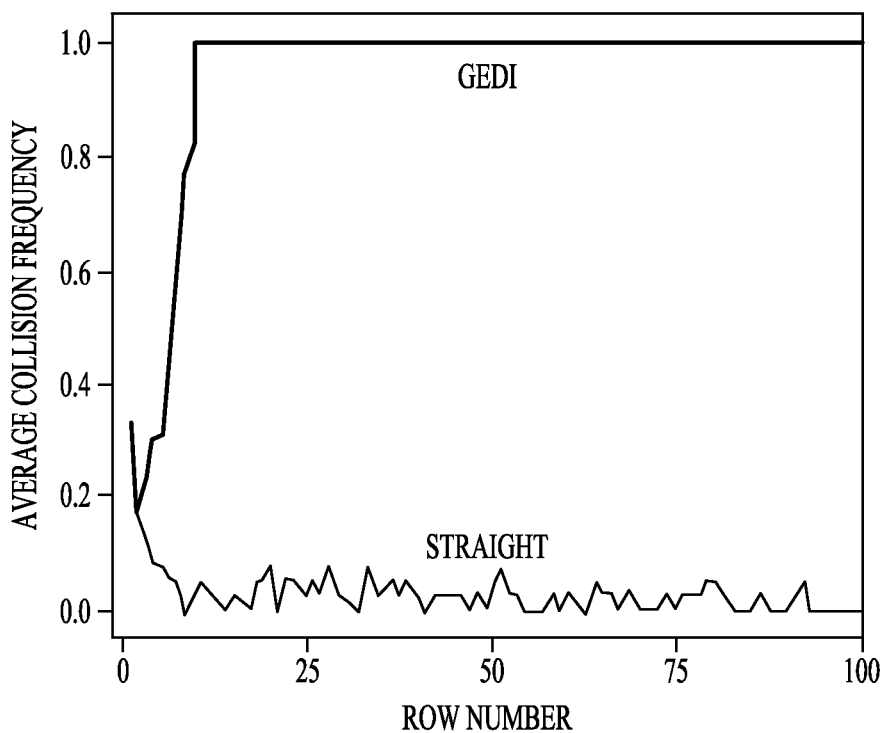

Because of the dependence of cell trajectory on cell diameter, collision rates are a complicated function of both cell diameter and array parameters such as row offsets. The collision rate per row (CpR) is a strong function of the row offset, exhibiting discontinuities, size dependence, and startup effects related to the finite array size (FIG. 2E). The dramatic difference between the performance of different designs is caused by the deflection of particles—in poorly-chosen geometries, the deflection causes cells to deflect onto streamlines that do not come into proximity with later obstacles, whereas in well-chosen geometries, the deflection causes cells to deflect onto streamlines that do come into proximity with later obstacles. Thus the collision rate increases as the cells proceed through the device for the GEDI design, and decreases for poorly chosen designs such as straight arrays (FIG. 2E). This cutoff allows the user to identify a cutoff between hematocytes (<14 µm) and the cell population that will experience maximum collisions (>15 µm).

Example 3

Cell Capture, Imaging, and Enumeration of Circulating Tumor Cells from Metastatic Prostate Cancer Patients This Example describes use of the GEDI device to capture and characterize circulating tumor cells (CTCs) from the blood of patients with metastatic castration-resistant prostate cancer.

One ml of peripheral blood was passed through the device, captured cells were fixed and immunostained for PSMA, CD45, EpCAM and DAPI, and the captured cells were analyzed by confocal microscopy. Circulating tumor cells were defined as intact, nucleated, $PSMA^+/CD45^-$ cells. Different cell lines were used as controls for antibody staining for PSMA, CD45, and EpCAM, as follows: the C4-2 prostate cancer cells are $PSMA^+/EpCAM^+/CD45^-$ while the PC3 prostate cancer cells are $PSMA^-/EpCAM^-/CD45^-$. The U937 leukemic cell line was used as a positive control for the leukocyte marker CD45. DAPI was used to stain the DNA.

Figure 3A:
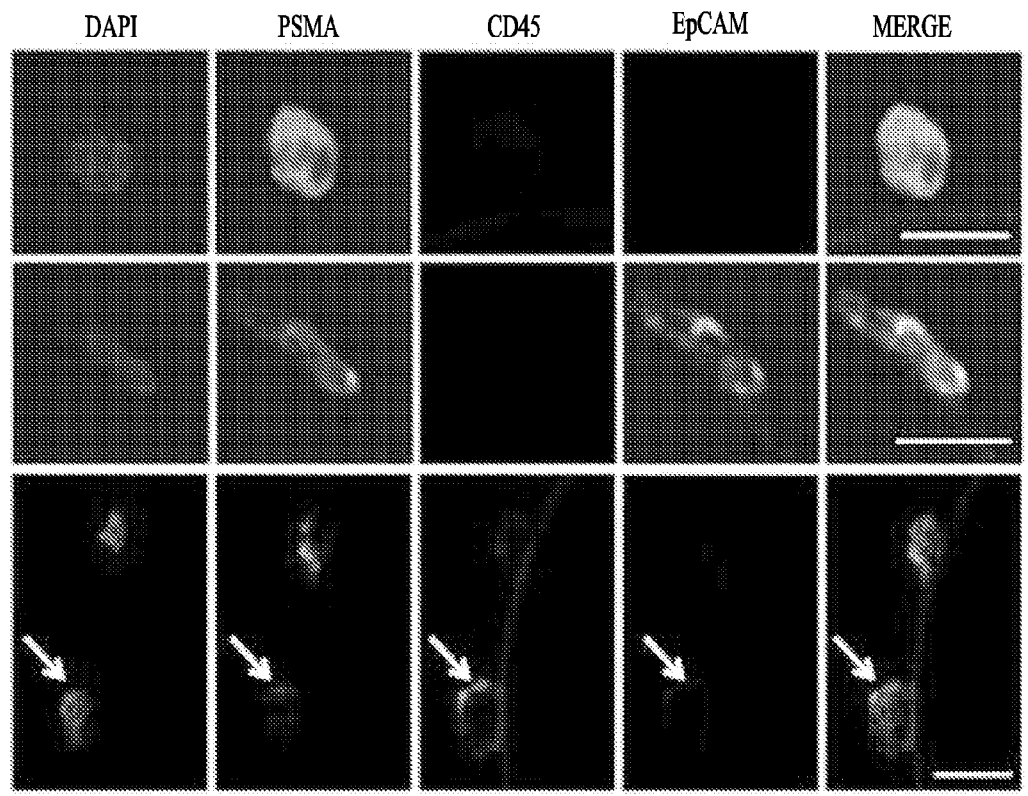
FIG. 3A-3D illustrate circulating tumor cell enumeration using the GEDI in comparison to capture by a CellSearch® device.

Representative examples of circulating tumor cells and leucocytes are shown in FIG. 3A. Interestingly, $PSMA^+$ cells had variable EpCAM staining, ranging from highly-positive to weak to negative in terms of EpCAM fluorescent intensity. In a subset of patients, the percent of PSMA-captured circulating tumor cells was quantitated that were EpCAM positive. About 40-70% of GEDI-captured circulating tumor cells were positive for both markers, with the median being 60% (data not shown). Controls for antibody performance were included with every experiment using two prostate cancer cell lines expressing different levels of PSMA and EpCAM (C4-2:PSMA$^+$/EpCAM$^+$/CD45$^-$ and PC3: PSMA$^-$/EpCAM$^-$/CD45$^-$) and the CD45$^+$ leukemia cell line U937.

Figure 3B:
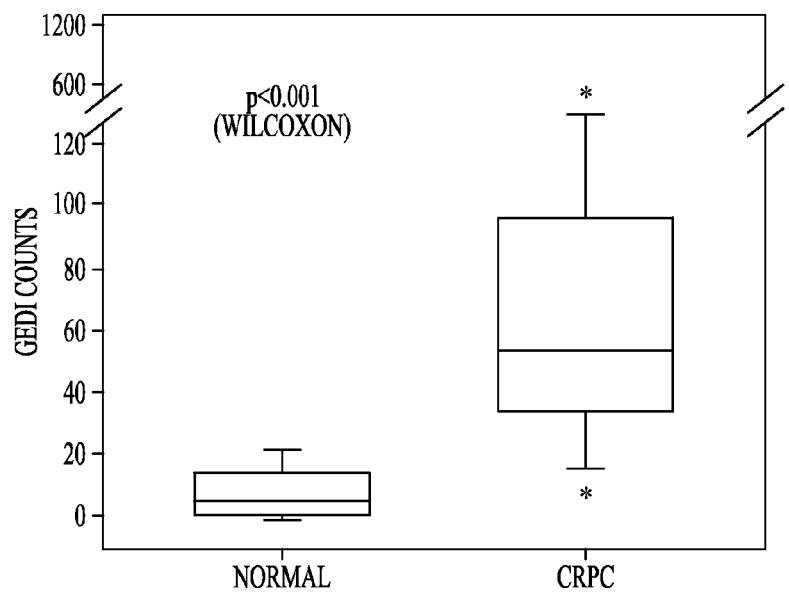

Blood samples obtained from 10 healthy donors (controls) and 30 patients with metastatic castration-resistant prostate cancer were processed using the GEDI device. The median number of circulating tumor cells/ml detected was 3 (range 0 to 22) and 54 (range 0 to 1200), respectively (p<0.001; FIG. 3B).

Figure 3C:
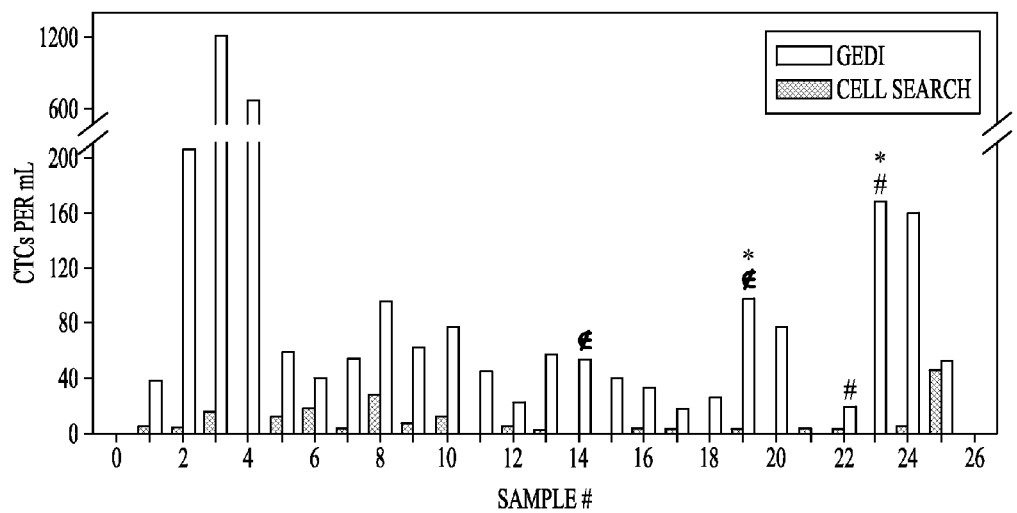
Figure 3D:
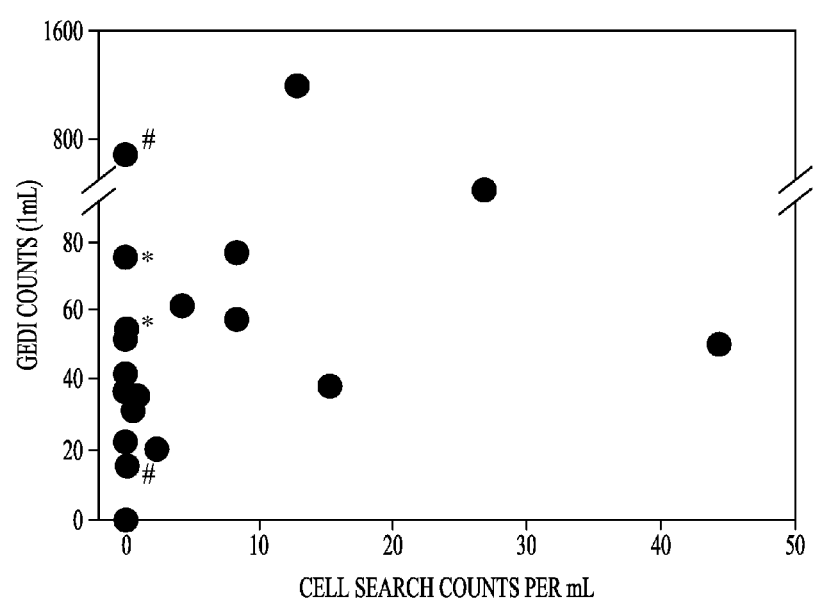

A direct comparison of circulating tumor cell capture and enumeration was then performed by comparing the GEDI microdevice with the FDA-approved EpCAM-based Cell-Search® CTC Test on same-day blood draws from 25 castration-resistant prostate cancer patients (FIG. 3C). A 2 to 400-fold increase was detected in the number of circulating tumor cells/ml reported with the GEDI microdevice relative to the CellSearch® CTC Test (FIG. 3C; p<0.0001, calculated with Wilcoxon test). A weak correlation (r=0.44; outliers removed with Cook's distance restriction) between GEDI circulating tumor cell counts and CellSearch® (FIG. 3D).

Example 4

Markers for Circulating Tumor Cells

This Example provides a comparison of cell capture by the GEDI device and the CellSearch® device.

The results presented in FIG. 3 illustrate both that the EpCAM expression level of captured PSMA$^+$/DAPI$^+$/CD45$^-$ cells is variable and that the correlation between GEDI PSMA$^+$ capture and CellSearch® EpCAM$^+$ capture is only weak. The two capture methodologies both correlate with the disease state, but the population captured by the GEDI device is different from that captured by the currently available CellSearch® device, presumably owing to different expression levels of EpCAM and PSMA in the circulating tumor cell population. The data described herein shows detection of a significantly higher circulating tumor cell population using the GEDI microfluidic device compared with CellSearch®. Thus the GEDI microdevice has enhanced sensitivity for detecting circulating tumor cells in samples obtained from prostate cancer patients. Because circulating tumor cells expressing low EpCAM levels are frequently missed using CellSearch® (Scher et al., Journal of clinical oncology: official journal of the American Society of Clinical Oncology 29: 2191-2198 (2011)), it is likely that anti-PSMA capture maybe be a more consistent methodology for circulating tumor cell isolation in metastatic prostate cancer patients.

To further investigate the distribution of the two antigens in castration-resistant prostate cancer isolated circulating tumor cells, in an unbiased manner (i.e. no antibody-specific circulating tumor cell capture) circulating tumor cells were isolated from castration-resistant prostate cancer patient sample by performing immuno-magnetic CD45 depletion of Ficoll-isolated peripheral blood mononuclear cells. These immuno-depleted cells were subsequently labeled with antibodies against PSMA (J591), EpCAM and CD45. In this assay, circulating tumor cells were classified as nucleated CD45– cells that were positive for PSMA, EpCAM, or both PSMA and EpCAM. A total of eleven patient samples were analyzed and circulating tumor cells were identified in seven patients. Over 80% of dual PSMA$^+$/EpCAM$^+$ circulating tumor cells in six of the seven patients (Table 1).

TABLE 1

Circulating Tumor Cell Counts

| Patient | PSMA | EpCAM | PSMA + EpCaM | Total |
|---|---|---|---|---|
| 1 | 176 | 172 | 169 (94.4%) | 179 |
| 2 | 125 | 130 | 119 (87.5%) | 136 |
| 3 | 104 | 103 | 96 (86.4%) | 111 |
| 4 | 1 | 0 | 0 | 1 |
| 5 | 2 | 1 | 1 (50%) | 2 |
| 6 | 1 | 1 | 1 (100%) | 1 |
| 7 | 6 | 6 | 6 (100%) | 6 |
| 8 | 0 | 0 | NA | 0 |
| 9 | 0 | 0 | NA | 0 |
| 10 | 0 | 0 | NA | 0 |
| 11 | 0 | 0 | NA | 0 |

Interestingly, using this technique, the EpCAM staining intensity was variable which is consistent with the data obtained using the GEDI-microdevice (FIG. 3).

Taken together these data indicate that an important contributing factor to the enhanced sensitivity of the GEDI is that the GEDI microdevice is designed to optimize circulating tumor cell capture and minimize leukocyte capture; it does this by inducing a fluid flow that generates size-dependent trajectories of cells that lead to size-dependent collision rates. Spatial separation of cells based on size alone would be of limited use in circulating tumor cell capture from blood—although circulating tumor cells tend to be larger on average that hematological cells, the sizes of cells and cell fragments of epithelial origin has a broad distribution, and size is much less specific to the circulating tumor cell phenotype than surface markers such as EpCAM, PSMA, or EGFR. However, when a surface antibody is present, size-dependent particle trajectories enable the captured cell population to be biased to reject nonspecific leukocyte adhesion. The surface collision rate and capture rate (FIG. 2) can be made size-specific, enhancing the receiver-operator characteristic of the rare cell capture. By capturing circulating tumor cells at high efficiency and purity, functional and molecular assays, exemplified by the ERG and SNP measurements in FIG. 4 and the tubulin measurements in FIG. 5 can be applicable in a clinical setting.

Example 5

Molecular Characterization of Captured Cells: Detection of a Single Point Mutation in the Androgen Receptor and Expression of the TMPRSS2-ERG Fusion in Spiked Cells and Circulating Tumor Cells This Example describes proof of principle experiments performed to assess the GEDI device.

To molecularly characterize the GEDI-captured circulating tumor cells, proof-of-principle experiments were performed in which prostate cancer cells were spiked into 1 ml of blood from a healthy donor, captured by the device and analyzed for the presence of androgen receptor (AR) point mutations or expression of a TMPRSS2:ERG gene fusion protein. To detect the T868A (ACT-GCT) single point mutation in the AR ligand-binding domain, fifty C4-2 cells were added into 1 ml of healthy donor blood that had passed through the GEDI device. RNA was extracted from the captured cells by direct lysis on the device followed by cDNA sequencing. In parallel, sequencing was performed on RNA extracted from 1 ml of the same healthy donor blood processed similarly (negative control) and on RNA extracted from fifty C4-2 cells (positive control).

Figure 4A:
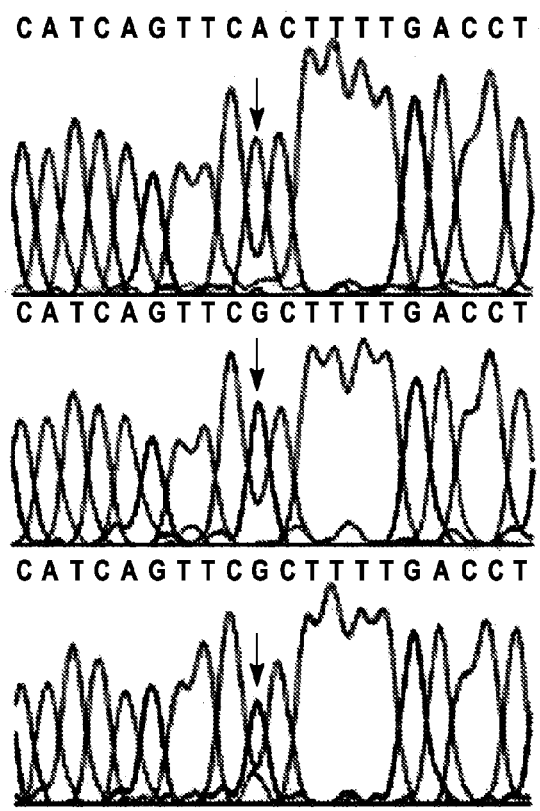
FIG. 4A-4E illustrate functional characterization and detection of genetic alterations in GEDI-captured cells.
Figure 4B:
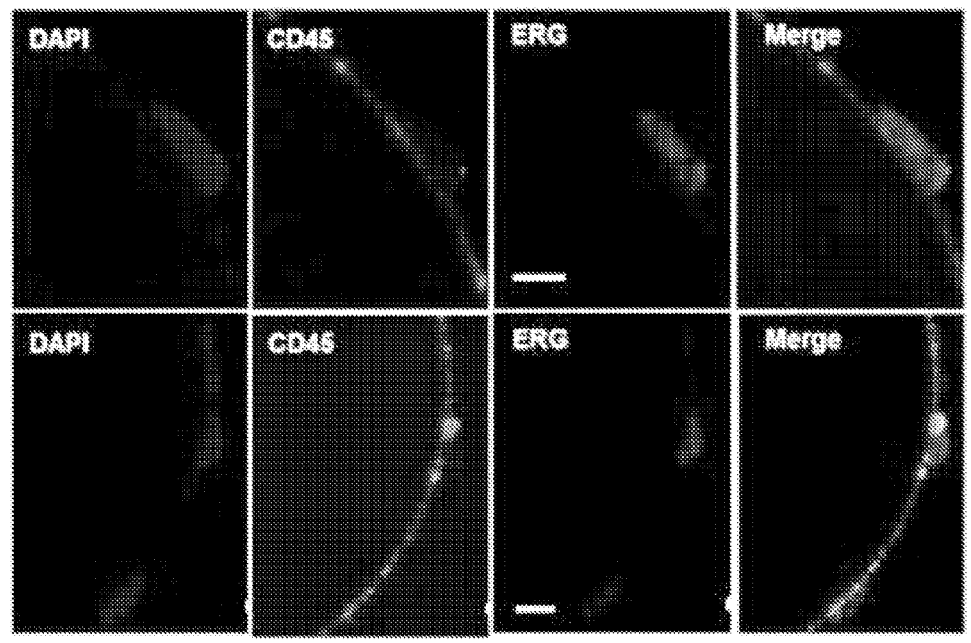

The sequencing results are illustrated in FIG. 4A. As expected, the T868A mutation was clearly detected in the C4-2 cells (FIG. 4A, top and middle panel) but absent from the negative control. The point mutation was also detected in the spiked blood sample, with the mutant peak (A) accounting for 70% of the nucleotide present at this position and the wild-type (T) for 30%. This result is consistent with the previously reported cell capture purity rate of 68% obtained with fluorescently labeled prostate cancer cells spiked into 1 ml peripheral blood from a healthy donor and flown through the GEDI microdevice (Gleghorn et al., Lab on a chip 10: 27-29 (2010).

Figure 4C:
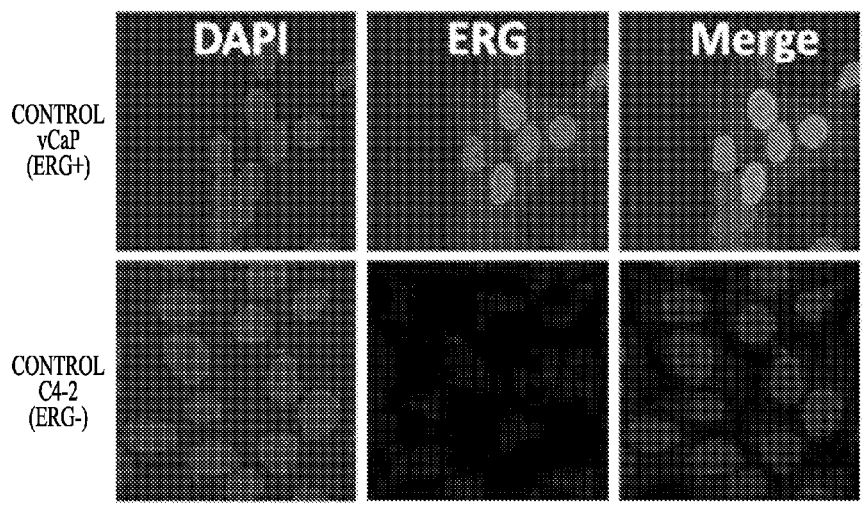
Figure 4D:
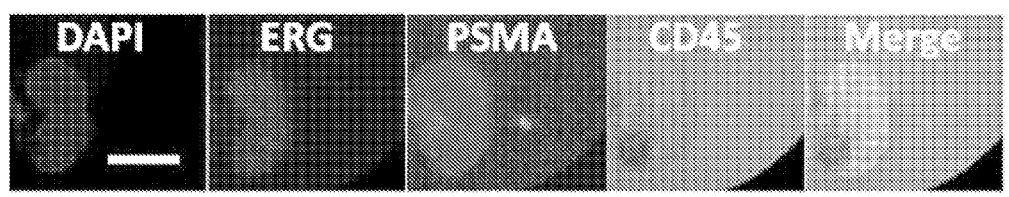

In addition, the presence of the TMPRSS2:ERG fusion protein could be detected by immunostaining with the rabbit monoclonal anti-ERG antibody (Park et al., Neoplasia 12: 590-598 (2010)) in fusion-positive vCaP prostate cancer cells captured by the device and analyzed by multiplex confocal microscopy (FIG. 4C-4D). Similar analysis on GEDI-captured circulating tumor cells from a castration-resistant prostate cancer patient revealed the presence of both ERG positive and ERG negative cells, while CD45+ leucocytes were negative for ERG protein (FIG. 4E), indicating the specificity of ERG staining for prostate cancer-derived cells.

Example 6

Tubulin Bundling Upon Exposure to Taxanes

This Example describes experiments showing that taxanes chemosensitivity can be detected in cells captured on the GEDI microdevice.

GEDI-captured circulating tumor cells are highly pure and viable, which is desirable for detection of drug resistance and/or drug sensitivity. The GEDI-captured circulating tumor cells were tested in situ (i.e., while in the GEDI device) to evaluate their chemosensitivity to taxanes, and predict a patient's clinical response to therapy. Taxanes (paclitaxel, docetaxel and cabazitaxel), which are commonly used to treat castration-resistant prostate cancer patients, act by stabilizing microtubule polymers and inducing the formation of microtubule bundles. Microtubule bundling is readily detectable by immunofluorescence staining, due to their increased fluorescence intensity, distinct shape and cytoplasmic organization when viewed in maximum signal projection (Marcus et al., J. Biol. Chem. 280: 11569-11577 (2005)). Microtubule bundling is the first event induced by taxane treatment, resulting in downstream mitotic arrest and apoptotic cell death, and is therefore an appropriate marker of efficient taxane drug-target engagement.

Figure 5A:
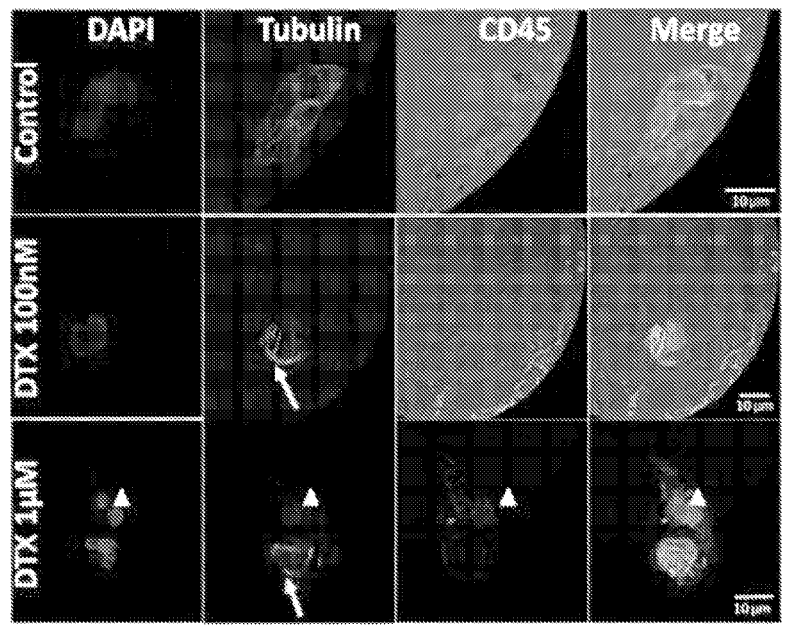
FIG. 5A-5F illustrates on-chip assessment of effective drug-target engagement in viable GEDI-captured circulating tumor cells, and that tubulin responses to taxane treatment can be assessed in GEDI-captured cells.

To first determine the optimal concentration and duration of ex-vivo on-chip treatment of patient-derived circulating tumor cells, 200 C4-2 cells were spiked into 1 ml of blood from a healthy donor, processed the sample in the GEDI device, and then incubated the captured cells on the device for 24 h in media containing 100 nM or 1 µM of docetaxel (DTX) at 37° C. Docetaxel treatment with 100 nM resulted in distinct microtubule bundles in captured C4-2 cells (FIG. 5A, middle panel arrows), in contrast to the fine and intricate microtubule network of the untreated GEDI-captured cells (FIG. 5A, upper panel). Treatment with 1 µM docetaxel resulted in robust microtubule bundling and induction of apoptotic events (FIG. 5A, lower panel arrowheads). Apoptotic events were determined by the presence of bright and fragmented nuclei accompanied by loss of tubulin staining. Similar results were obtained with 48 hour, on-chip, ex-vivo treatment (data not shown). These results, together with the fact that the AUC of serum docetaxel concentration for patients administered 55-100 mg/m$^2$ of docetaxel is approximately equal to 1.5-5 hours mg/l, indicated that 24 hour treatment with 100 nM of a taxane (1.92 hours mg/l) can be used to evaluate the ex-vivo response of patient-derived circulating tumor cells.

Figure 4E:
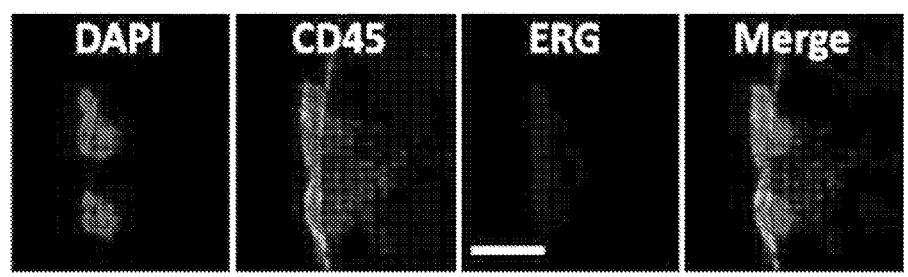
Figure 5B:
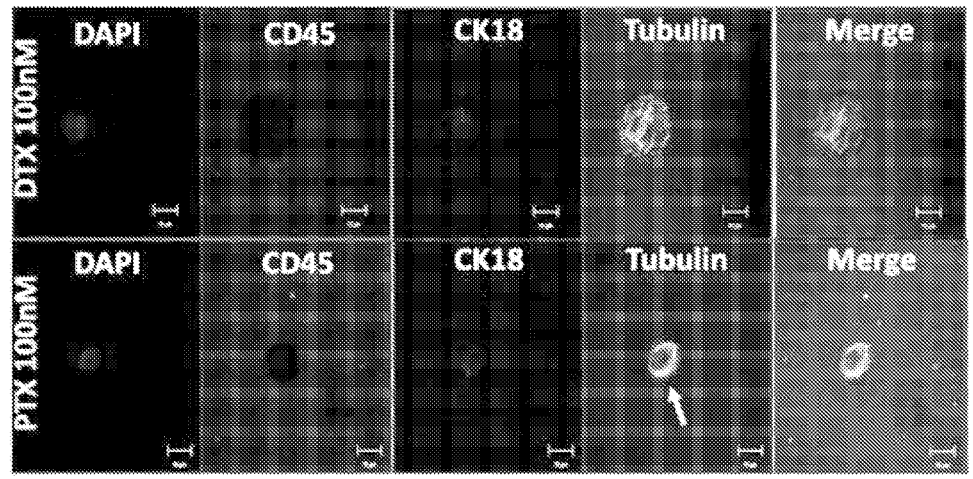
Figure 5C:
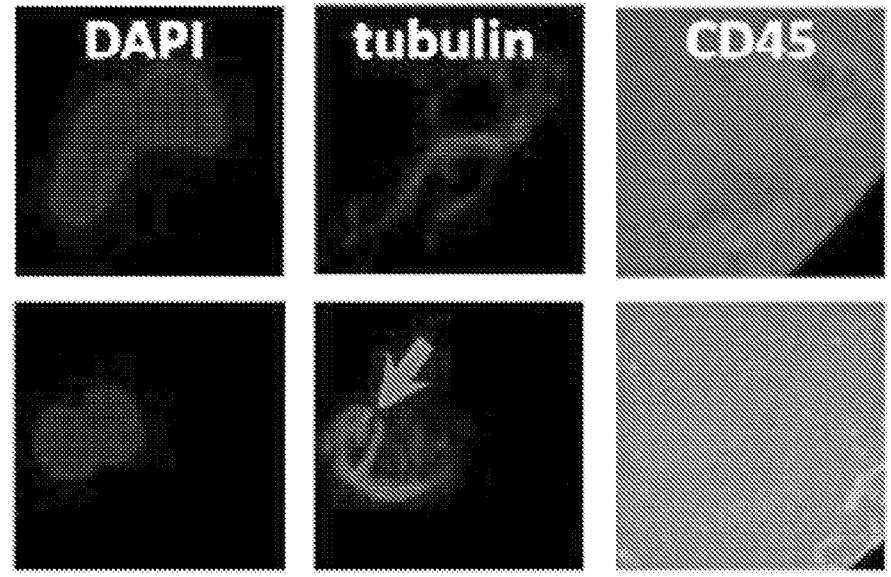
Figure 5D:
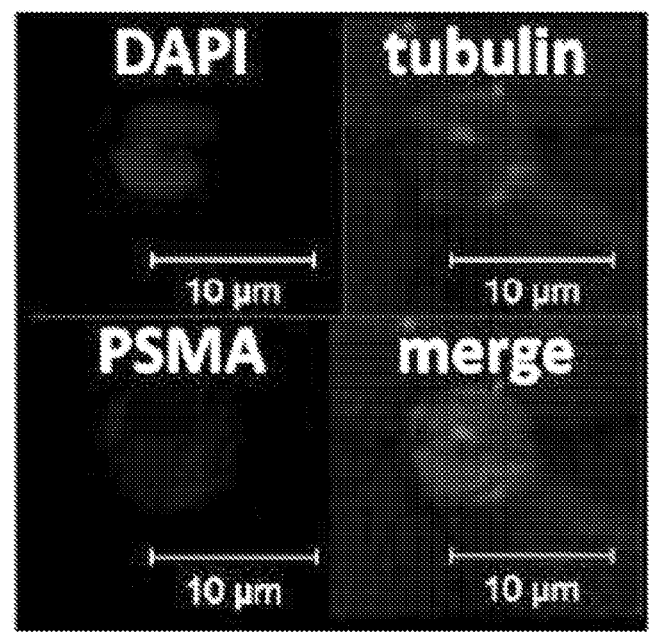
Figure 5E:
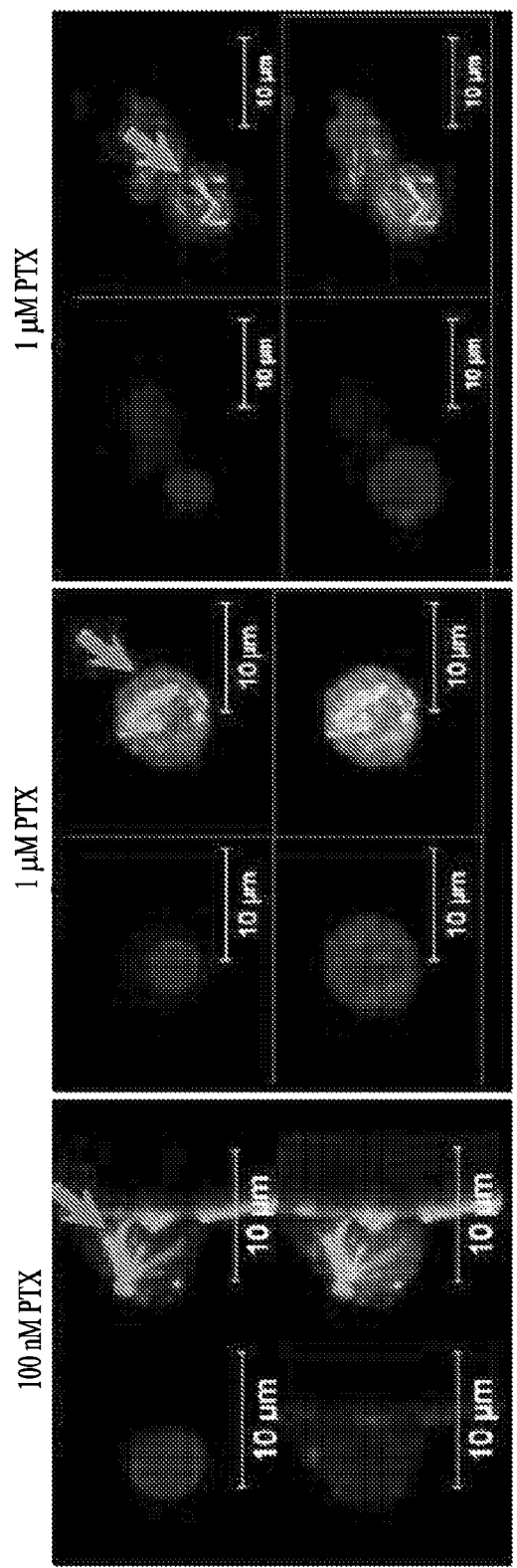
Figure 5F:
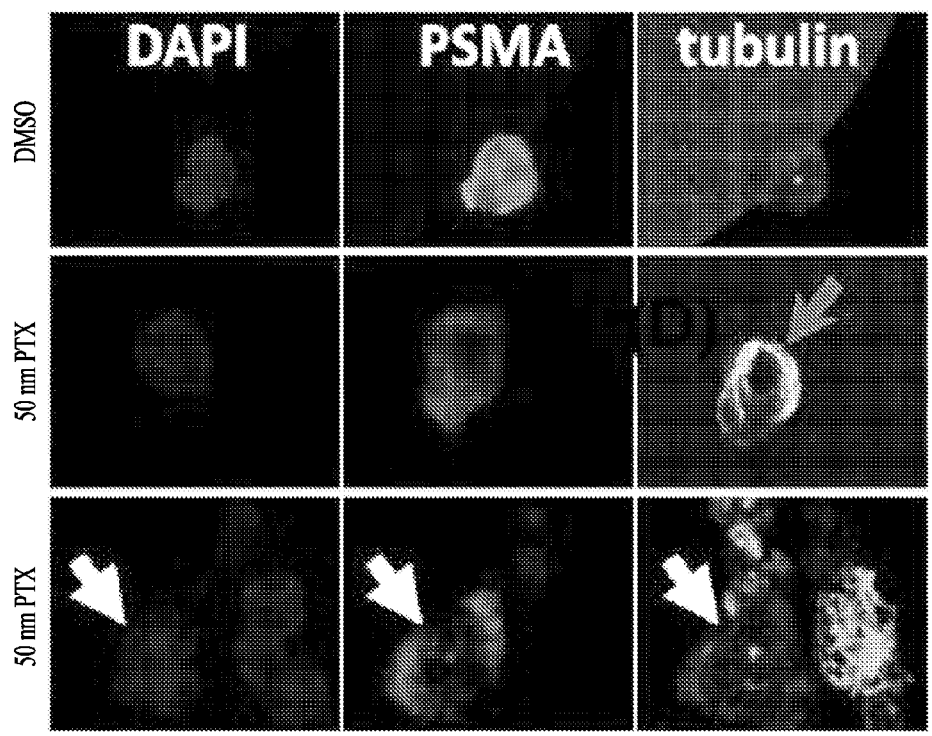

A number of assays were performed to show the potential for functional assay in the described device. In these cases cells captured in the device were treated ex vivo with docetaxel and/or paclitaxel for 24 hr (FIGS. 5B and 4E). These highlight the ability to perform functional assays on chip and assay drug-target engagement in patients in the context of their clinical response. Non-response, as indicated by a lack of evidence of microtubule bundling or apoptotic nuclei following ex-vivo docetaxel treatment, could be observed in some patients. FIG. 5E shows a patient that was non-responsive by the microtubule assay, consistent with this patient's lack of a clinical response using established RECIST and PSAWG2 criteria. This response was often heterogeneous within the captured cell population; FIG. 5F shows images of cells from a patient with heterogeneous response within the PSMA+ circulating tumor cell population, with only 45% of circulating tumor cells displaying clear evidence of microtubule bundling (whereas nearly 100% of the leucocytes present on the chip showed microtubule bundling). Interestingly, cell response was often specific to the taxane used. As an example of this, FIG. 5B (top panel) shows a sample in which ex vivo docetaxel had no effect on the microtubule cytoskeleton of captured circulating tumor cells, whereas isolated circulating tumor cells from the same patient (docetaxel progressor) treated with paclitaxel demonstrated clear evidence of microtubule bundling (FIG. 5B, bottom panel) as well as signs of aberrant mitotic arrest (FIG. 5C). FIG. 5D shows exemplary results of a patient (docetaxel progressor on cabazitaxel) whose circulating tumor cells exhibited apoptotic nuclei with paclitaxel but not with docetaxel.

Example 7

Additional Methods for Evaluation of Androgen Receptor Splice Variants

This Example describes additional materials and methods that have been used for evaluation of androgen receptor splice variants.

Cell Lines and Reagents:

PC3 and HEK293T cells were obtained from ATCC (Manassas, Va.) and a PC3 stable cell line expressing mCherry-tubulin (PC3:mCherry-tub) was generated and maintained as previously described by Darshan et al. (Cancer Res. 71: 6019 (2011)).

M12 stable cell lines expressing untagged wild-type androgen receptor (AR-wt), ARv5,6,7es and ARv7 or expressing Cumate-inducible FLAG-tagged AR-wt or variants were generated in Dr. Plymate's laboratory (University of Washington School of Medicine, Seattle, Wash.) and maintained in RPMI 1640 supplemented with 5% FBS, 0.01 µM dexamethasone (Sigma Aldrich, St Louis, Mo.), 10 ng/ml epidermal growth factor (Invitrogen), 10 ml/L insulin-transferrin-selenium (Cellgro, Manassas, Va.), 100 I.U./ml penicillin plus 100 µg/µl streptomycin and 200 µg/µl G418 (Cellgro, Manassas, Va.) at 37° C. with 5% $CO_2$.

In addition, M12 cells stably expressing GFP-tagged AR-wt, AR or variants were generated in Or Giannakakou's laboratory. GFP+ cells from all three androgen receptor cell lines were sorted using fluorescence activated cell sorting (FACS) on a BD FACSAria II cell sorter (BD Biosciences, Franklin Lakes, N.J., USA) and subsequently expanded in media containing G418 (400 ng/mL).

Unless otherwise stated, all reagents used were from Sigma Aldrich (St. Louis, Mo.). For immunofluorescence the following primary and secondary antibodies were used: rat monoclonal anti α-tubulin (Novus Biologicals, Littleton, Colo.), mouse monoclonal anti-c-Myc (Merck, Darmstadt, Germany) and species-matching Alexa Fluor 488 and Alexa Fluor 568 conjugated antibodies from Invitrogen (Carlsbad, Calif.). For immunoprecipitation rat monoclonal anti α-tubulin, rabbit polyclonal anti-GFP (Novus Biologicals) and mouse anti-dynein (Covance, Emeryville, Calif.) antibodies were used. For the immunoblot assays mouse monoclonal anti-androgen receptor 441 (Novus Biologicals); rabbit monoclonal anti-androgen receptor (EP670Y from Abcam, Cambridge, Mass.) specific for the C-terminus; rat monoclonal anti α-tubulin; rabbit polyclonal anti-GFP (Abcam) and rabbit polyclonal anti-actin (Sigma Aldrich) antibodies were used. Alexa Fluor 680 (Invitrogen) and IRDye 800 (Rockland) conjugated antibodies were used as secondary antibodies. Protease inhibitor cocktail tablets (including serine and cysteine proteases) were purchased from Roche (Indianapolis, Ind.). NLP-005 Methyltrienolone (R1881) was purchased from Perkin Elmer (Boston, Mass.). Nonidet P-40 was purchased from US Biological (Swampscott, Mass.). Paclitaxel was obtained from Sigma Aldrich and docetaxel from Sanofi Aventis (Kansas City, Mo.). Generation of androgen receptor truncated mutants:

The full-length GFP-AR plasmid (pEGFP-C1-AR-Q22) was generously provided by Dr. Michael Mancini (Baylor College of Medicine, Houston, Tex.) and used as the template to generate all androgen receptor-truncated mutant constructs. All PCR-generated androgen receptor-truncated mutant constructs were sub-cloned into the expression vector pEGFP-C1. All cloning was performed using AccuPrime Taq DNA Polymerase High Fidelity (Invitrogen), with 10 µM forward and reverse cloning primers (IDT, San Diego, Calif.). All primers were designed using the human androgen receptor mRNA reference sequence (GenBank NM_000044).

AR 540-724 and AR 725-919 were subcloned into the p3xFLAG-CMV-14 expression vector (Sigma) with the following specific primers:

```
AR 540-724 forward:
                                (SEQ ID NO: 14)
5'-CGCACGATATCGCCACCATGTTGGAGACTGCCAGGGACC-3';

AR 540-724 reverse:
                                (SEQ ID NO: 15)
5'-CGCACGGATCCAGGCAAGGCCTTGGCCCAC-3';
and AR 725-919 forward:
                                (SEQ ID NO: 16)
5'-CGCACGATATCGCCACCATGGGCTTCCGCAACTTACACGTG-3';

AR 725-919 reverse:
                                (SEQ ID NO: 17)
5'-CGCACGGATCCCTGGGTGTGGAAATAGATGGG-3'.
```

Amplification products were analyzed by Sanger sequencing to confirm the integrity of all constructs.
Immunoprecipitation and Western Blotting:

HEK293T cells transiently transfected with GFP-tagged AR-wt AR, ARv5,6,7 or ARv7 were lysed in TNES buffer and subjected to immunoprecipitation as previously described by Darshan et al. (*Cancer Res* 71, 6019 (Sep. 15, 2011)).
Microtubule Co-Sedimentation Assay:

PC3-mCherry-tubulin and HEK293T cells were transiently transfected with GFP-tagged androgen receptor, AR-wt or GFP-ARv7 or HA-tagged ARv5,6,7 and subjected to microtubule co-sedimentation assay as previously described by Giannakakou et al. (*Nat Cell Biol* 2, 709 (October, 2000)). Briefly, 1 mg of total cell lysate was first pre-cleared by high-speed centrifugation, the pellet (HSP) was discarded while the supernatant (HSS) was supplemented exogenous purified with bovine brain tubulin (Cytoskeleton, Denver, Colo.) reconstituted at a final concentration of 10 µM in the presence of 1 mM GTP, and 20 µM paclitaxel (PTX) and subjected to a cycle of polymerization for 30 min at 37° C. Samples were centrifuged at 100,000×g for 30 min at room temperature and the warm supernatant (WS) was separated from the warm pellet (WP), which was resuspended in an equal volume of PEM buffer. Equal volumes from each respective fraction were loaded onto a SDS-PAGE and transferred and immunoblotted with antibodies against androgen receptor, α-tubulin and actin. Densitometry for each respective protein was performed using ImageJ (National Institutes of Health) software and the percentage of the protein present in the pellet fraction was calculated using the following formula: % P=100*WP/(WP+WS).
Quantitative Real Time PCR:

M12-cumate inducible AR-wt or variant cells were treated with cumate (Cu) for 48 h and then starved for 24 h in CSS media. Cells were treated with 1 µM docetaxel (TXT) for 4 h either alone or followed by 10 nM R1881 overnight. QPCR for TMPRSS2, FKBP51 and GAPDH was performed as previously described by Chan et al. (*J Biol Chem* 287, 19736 (Jun. 1, 2012)).
Dynamitin Overexpression, Immunofluorescence and Confocal Microscopy:

M12 cells stably expressing the untagged androgen receptor constructs were transiently transfected with c-Myc-tagged pCMVH50m plasmid containing dynamitin (gifted by R. Vallee, Columbia University, New York, N.Y.) using FuGENE 6, according to the manufacturer's instructions. Twenty four hours post-transfection, the cells were treated with the indicated drugs. Images were acquired by confocal microscopy and image analysis was performed as previously described by Darshan et al. (*Cancer Res* 71, 6019 (Sep. 15, 2011)).
Live Cell Imaging:

PC3-mCherry-tubulin cells were plated on MatTek (Ashland, Mass.) 5 mm, Poly-d-lysine coated glass bottom dishes and cells were pressure-microinjected intranuclearly with plasmids encoding the different GFP-AR cDNAs as previously described by Darshan et al. (*Cancer Res* 71, 6019 (Sep. 15, 2011)). Time-lapse images were taken using a Spinning Disk microscopy system consisting of a Zeiss Axiovert 200 system fitted with a Yokogawa CSU-X1 spinning disk head (Tokio, Japan). Time lapse microscopy and image analyses were performed as previously described by Darshan et al. (*Cancer Res* 71, 6019 (Sep. 15, 2011)).
Xenograft Tumors LuCaP human prostate cancer xenografts were grown as previously described by Mostaghel et al. (*Clin Cancer Res* 17, 5913 (Sep. 15, 2011)) and Wu et al. (*Clin Cancer Res* 12, 6153 (Oct. 15, 2006)) in non-castrated SCID mice. Briefly, when the tumor volume reached an estimated size of 200 mm$^3$ (l×w$^2$/2) mice were treated with either vehicle or docetaxel at 5 or 20-mgm/kg intraperitoneally. weekly until tumors in the control group reached a tumor volume of 1000 mm³. At this time all animals in a group were sacrificed.
Immunohistochemistry Androgen receptor immunostaining of explanted LuCaP tumors was conducted as previously described by Zhang et al. (*PLoS One* 6, e27970 (2011)).
Statistical Analysis:

The p-values for androgen receptor nuclear localization in control, taxane and nocodazole treated cells were calculated using one-way analysis of variance followed by multiple comparisons with Bonferroni adjustments using Stata Statistical Software: release 10. The p-value for androgen receptor nuclear versus cytoplasmic localization in M12 cells were calculated using two-tailed unpaired T-Test.

Example 8

Microtubule Binding is Mediated by the C-Terminal Domain of the Androgen Receptor This Example describes experimental results showing that the C-terminal domain of androgen receptors bind to microtubules.

The inventors have previously shown that wild type androgen receptor (AR-wt) associates with the microtubule cytoskeleton and that this association is important for androgen receptor cytoplasmic to nuclear translocation and transcriptional activity in castration-resistant prostate cancer (Darshan et al., *Cancer Res* 71, 6019 (Sep. 15, 2011); Thadani-Mulero et al., *Cancer Res* 72, 4611 (Sep. 15, 2012)). However, the androgen receptor protein domain required for microtubule association has previously not been identified.

Figure 6A:
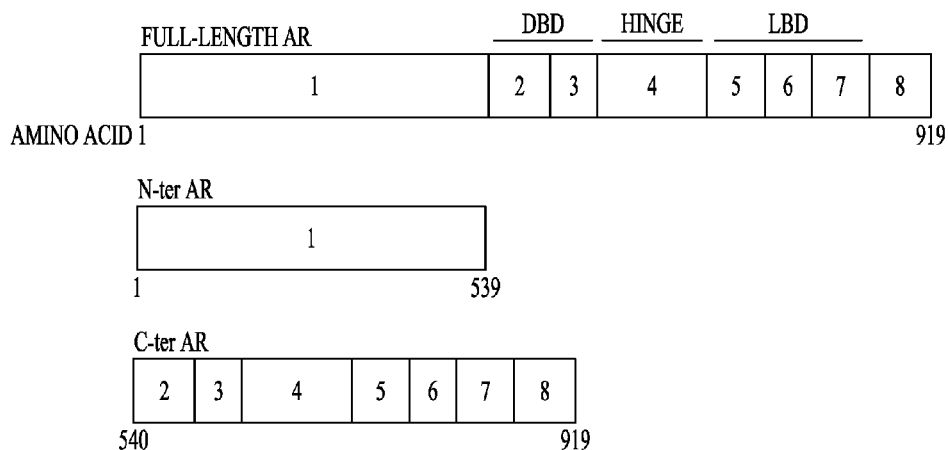
FIG. 6A-6E illustrate that microtubule-binding is mediated by the C-terminal domain of the androgen receptor.

To determine where the microtubule binding domain is within the androgen receptor protein a microtubule co-sedimentation assay was performed using cells expressing overlapping truncated androgen receptor mutants, which were generated by a serial mutagenesis approach. Initially, two large androgen receptor truncations were generated and sub-cloned into a pEGFP-C1 vector: the N-terminal domain (N-ter, amino acids 1-539) encompassing exon 1 of the androgen receptor and the C-terminal domain (C-ter, amino acids 540-919) encompassing the DNA binding domain, the hinge region and the ligand binding domain of AR (FIG. 6A). Each deletion mutant was individually expressed in either PC3:mCherry-tub or HEK293T cells by transient transfection and cells were subjected to microtubule co-sedimentation in order to assess each proteins' association with microtubule polymers. In this assay cell lysates from each condition (HSS) were supplemented with exogenous purified tubulin and subjected to a cycle of microtubule polymerization at 37° C. and in the presence of GTP and Taxol. Under these conditions purified tubulin along with endogenous cellular tubulin is robustly polymerized enabling microtubule interactions with cellular proteins. Following the polymerization reaction, high-speed centrifugation separated microtubule polymers along with any cellular proteins with affinity for them into the warm pellet (WP) fraction, while soluble tubulin and other proteins that did not have affinity for microtubules segregated with the warm supernatant (WS). The distribution of androgen receptor proteins between the WP and WS fractions indicates its ability to associate with the microtubule polymers, as in all conditions the majority of tubulin was identified in the WP fraction indicating efficient polymerization. GFP-tagged AR-wt androgen receptor was used as a positive control for microtubule association.

Figure 6B:
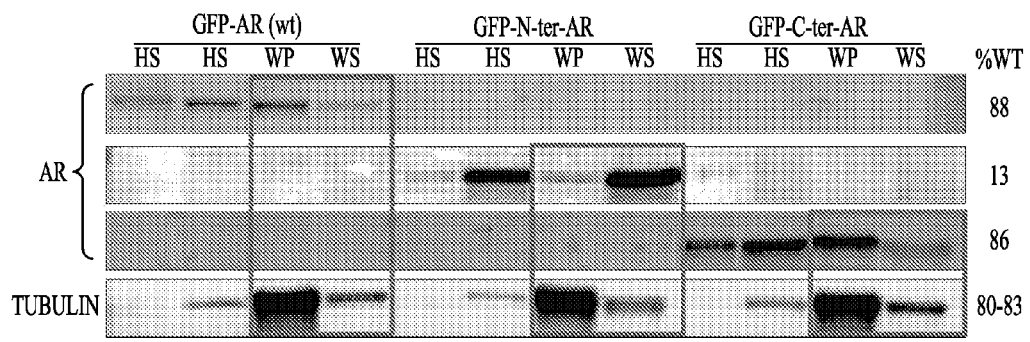
Figure 6D:
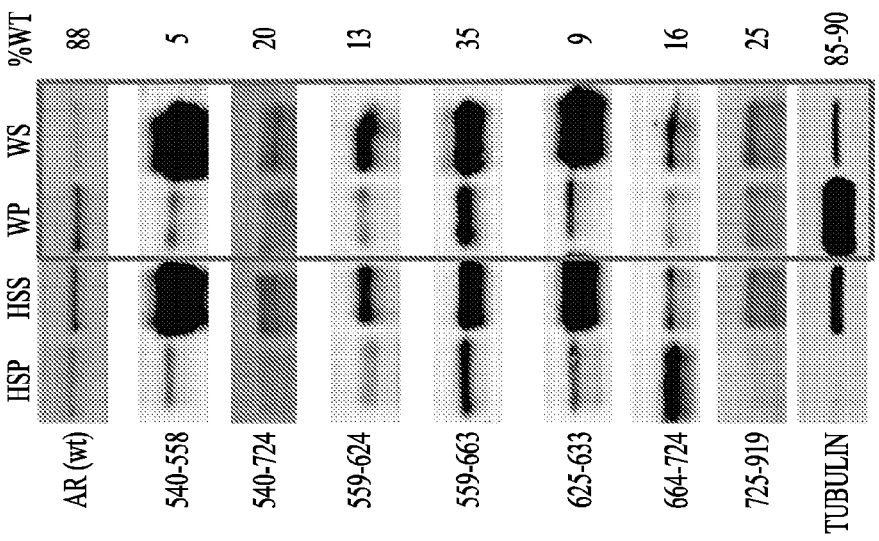
Figure 6C:
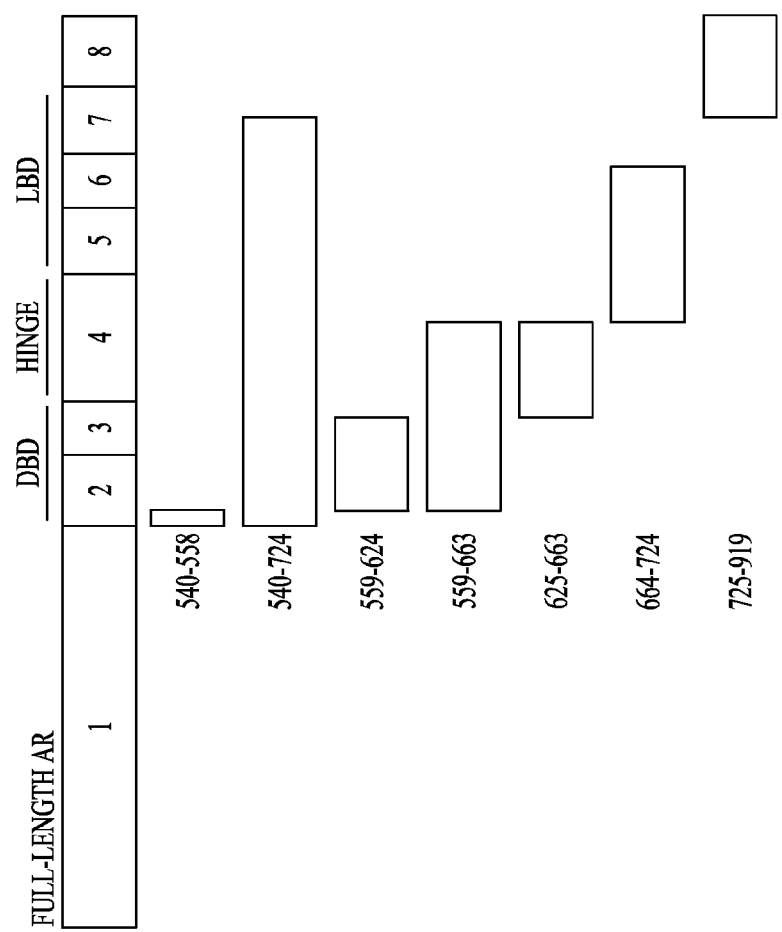
Figure 6E:
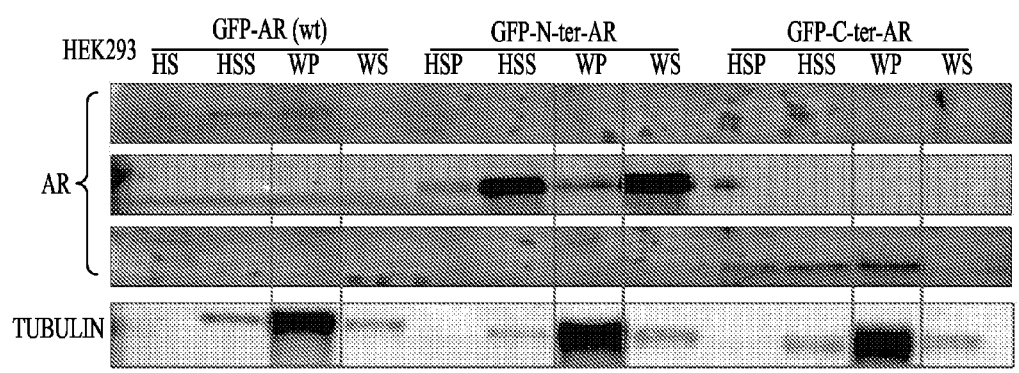

As shown in FIGS. 6B and 6E, the C-terminal domain of the androgen receptor associated preferentially with microtubule polymers in both cell lines. In particular, 86% of the C-terminal androgen receptor co-fractionated with microtubules in the WP fraction, in a manner similar to the AR-wt. In contrast, the N-terminal androgen receptor showed minimal association (13%) with polymerized tubulin (FIGS. 6B and 6E). Tubulin was efficiently polymerized in all conditions as shown by the majority of tubulin (over 80%) found in respective WP fractions.

In order to further narrow down the minimum AR-microtubule binding domain, seven additional androgen receptor truncation mutants were generated within the C-terminal region (FIG. 6C). The truncations were designed to correspond to androgen receptor functional domains as well as to cover the entire C-terminal region. In particular, the following truncations were generated:
the DNA binding domain (amino acids 559-624),
the hinge region (amino acids 625-663),
the DNA binding domain plus the hinge region (amino acids 559-663) and
the 540-724 amino acid fragment,
the 540-558 amino acid fragment,
the 664-724 amino acid fragment, and
the 725-919 amino acid fragment.

These deletion mutants were subcloned into a pEGFP-C1 vector, with the exception of the fragment containing amino acids 540-724 and the fragment containing amino acids 725-919 mutants were subcloned into a p3XFLAG-CMV vector, and with the GFP-tag gave rise to a protein of approximately 50 kDa, which is also the size of tubulin, whose excess made the detection of the truncated proteins very challenging.

Of the seven truncation mutants, the androgen receptor amino acid 559-663 fragment, corresponding to the DNA binding domain plus the hinge region, showed the most extensive association with the microtubule polymers with 35% protein seen in the WP (FIG. 6D). Surprisingly, none of these androgen receptor deletion mutants showed as extensive association with the microtubule polymer fraction as the original C-terminal androgen receptor fragment (FIG. 6B), indicating a likelihood that different parts of the C-terminal region of the androgen receptor contribute to effective tubulin association.

Example 9

ARv5,6,7 Associates More Extensively with Microtubules than ARv7

This Example describes experiments showing that the ARv5,6,7 variant co-fractionated almost exclusively (70%) with microtubule polymers, while the ARv7, only partially co-fractionated with microtubules.

Experiments were performed to investigate whether any of the two most clinically prevalent AR splice variants with truncations in their C-terminus, namely ARv5,6,7 (Sun et al., *J Clin Invest* 120, 2715 (August, 2010)) and ARv7 (Guo et al., *Cancer Res* 69, 2305 (Mar. 15, 2009); Hu et al., *Cancer Res* 69, 16 (Jan. 1, 2009)), would associate with microtubules similar to the AR-wt. Microtubule co-sedimentation revealed that the ARv5,6,7 variant co-fractionated almost exclusively (70%) with microtubule polymers in the WP fraction while ARv7, only partially co-fractionated with microtubules at 42% (FIG. 7B).

Example 10

Nuclear Translocation of ARv5,6,7, but not of ARv7, is Impaired by Microtubule Targeting Drugs This Example describes experiments demonstrating that drugs that target microtubules impair the nuclear translocation of the Arv5,6,7 variant, which affects the transcription of genes normally regulated by the androgen receptor.

The distinct pattern of microtubule association exhibited by the two AR variants suggested potentially distinct mechanisms of nuclear translocation. To test this hypothesis, the microtubule network was perturbed by 2 hr treatment with drugs that either stabilize (docetaxel) or depolymerize (nocodazole) microtubules. The nuclear accumulation of the androgen receptor variants was then assessed in cells microinjected with GFP-tagged ARv5,6,7 or ARv7. Live cell confocal microscopy was then used to image the dynamics of androgen receptor variant nuclear accumulation by obtaining z-stack images every 10 minutes for a total of 120 min.

Representative images from each condition are shown in FIG. 8. As shown in FIG. 8, the nuclear accumulation of ARv5,6,7 was significantly impaired following microtubule perturbation with either of the docetaxel or nocodazole drugs. In contrast, the ARv7 remained largely unaffected and remained substantially localized within the nucleus.

The two variants were found predominantly in the nucleus of untreated cells as soon as the GFP-tagged protein was expressed following microinjection (time 0). Despite their initial nuclear localization at baseline, the two variants exhibited entirely distinct responses to drug-induced microtubule disruption. The extent of nuclear localized ARv5,6,7 was quantified, revealing a significant decrease in its nuclear localization following microtubule perturbation at all time points observed (FIG. 8C and Tables 2 and 3; $p<0.01$ at baseline and $p<0.001$ at all other time points).

TABLE 2

Figure 7A:
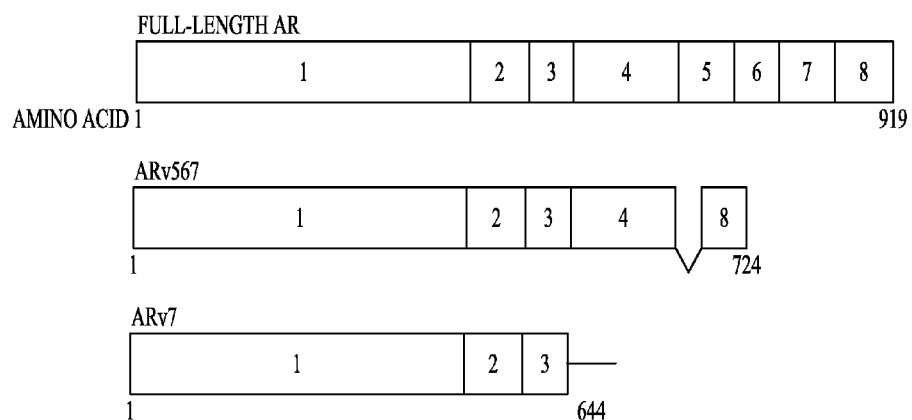
FIG. 7A-7C illustrate that ARv5,6,7, but not ARv7, associates with the microtubule polymer.
Figure 7B:
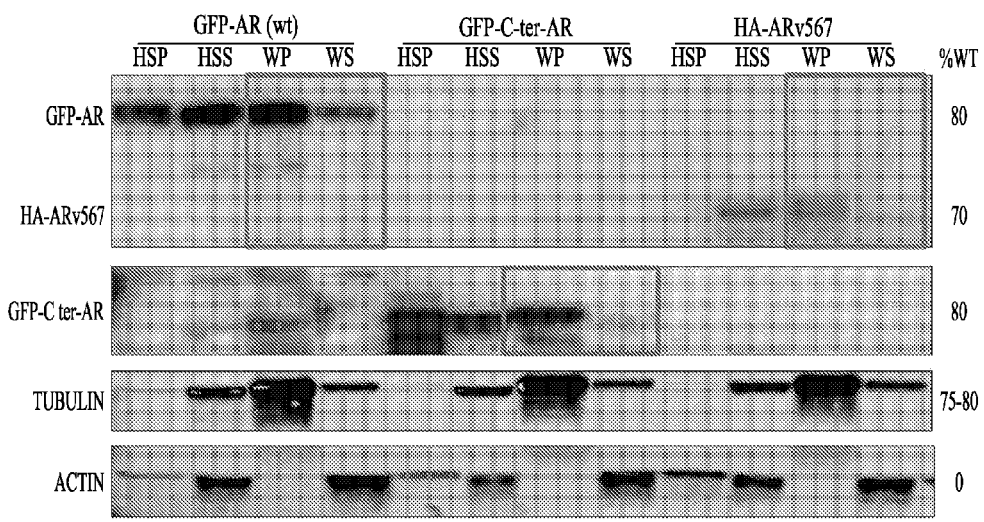
Figure 7C:
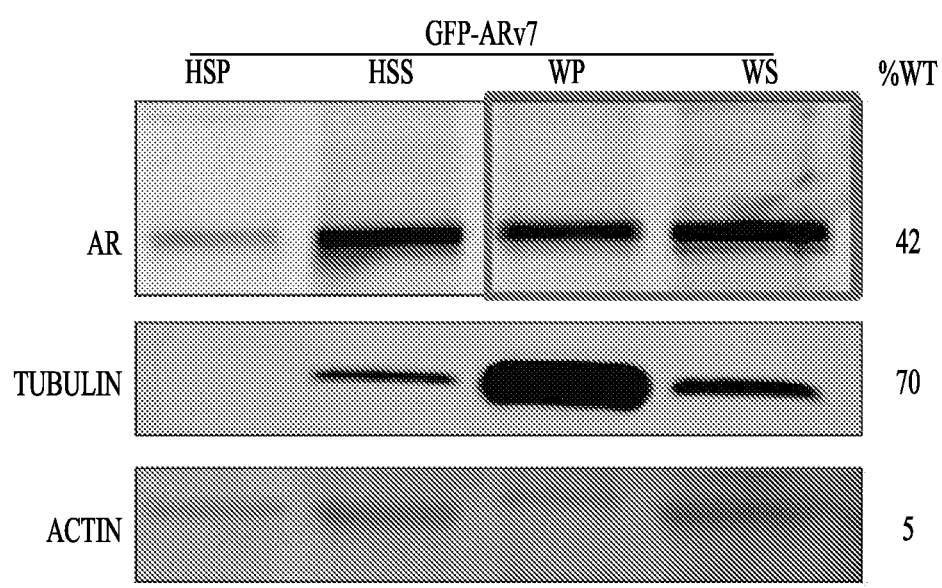

P-values for the live cell imaging experiments with PC3:mCh-tub-ARv5,6,7, shown in FIG. 7C-7D

| Time (min) | P value (Control vs. TXT) | P value (Control vs. Noc) |
|---|---|---|
| 0 | 0.02 | 0.00 |
| 10 | 0.02 | 0.00 |
| 20 | 0.01 | 0.00 |
| 30 | 0.00 | 0.00 |
| 40 | 0.00 | 0.00 |
| 50 | 0.00 | 0.00 |
| 60 | 0.00 | 0.00 |
| 70 | 0.00 | 0.00 |
| 80 | 0.00 | 0.00 |
| 90 | 0.00 | 0.00 |
| 100 | 0.00 | 0.00 |
| 110 | 0.00 | 0.00 |
| 120 | 0.001 | 0.00 |

TABLE 3

P-values for the live cell imaging experiments with PC3:mCh-tub-ARv7 displayed in FIG. 7C and 7D

| Time (min) | P value (Control vs. TXT) | P value (Control vs. Noc) |
|---|---|---|
| 0 | 1.000 | 1.000 |
| 10 | 1.000 | 1.000 |
| 20 | 1.000 | 0.561 |
| 30 | 1.000 | 0.382 |
| 40 | 1.000 | 0.621 |
| 50 | 1.000 | 0.249 |
| 60 | 1.000 | 0.482 |
| 70 | 1.000 | 0.491 |
| 80 | 1.000 | 0.646 |
| 90 | 1.000 | 0.545 |
| 100 | 1.000 | 0.922 |
| 110 | 1.000 | 0.750 |
| 120 | 1.000 | 0.787 |

Figure 8A:
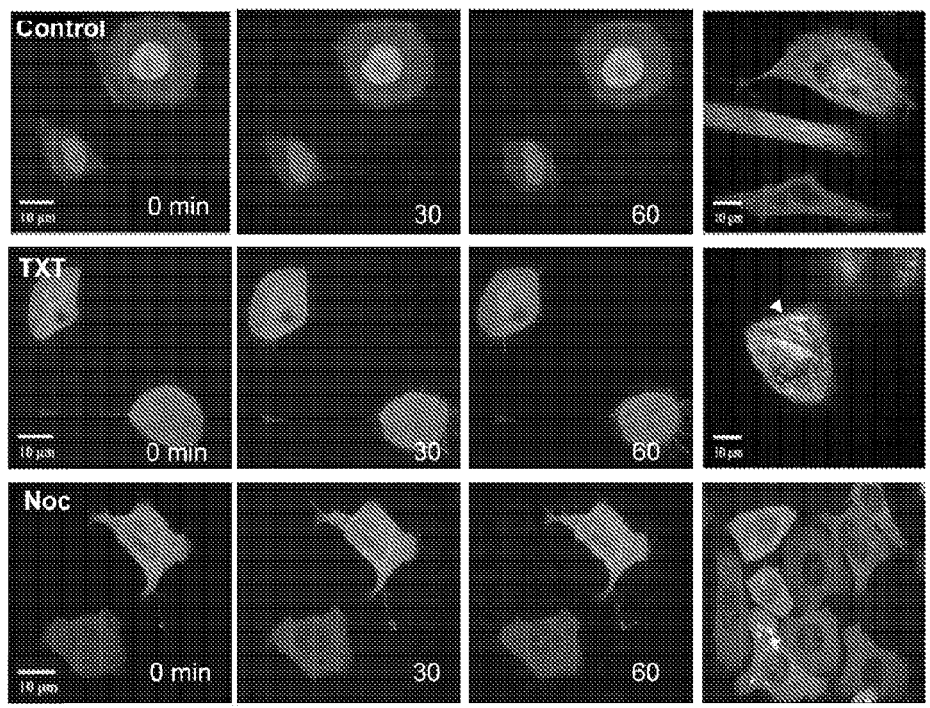
FIGS. 8A-8D illustrate that microtubule targeting drugs inhibit ARv5,6,7 nuclear trafficking but have no effect on ARv7 nuclear accumulation.
Figure 8B:
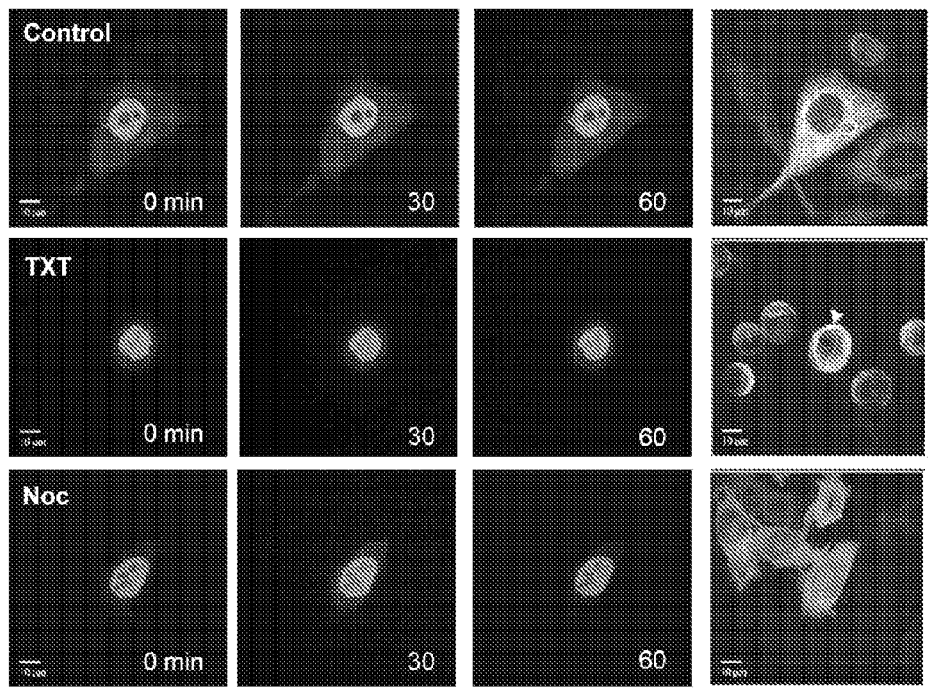
Figure 8C:
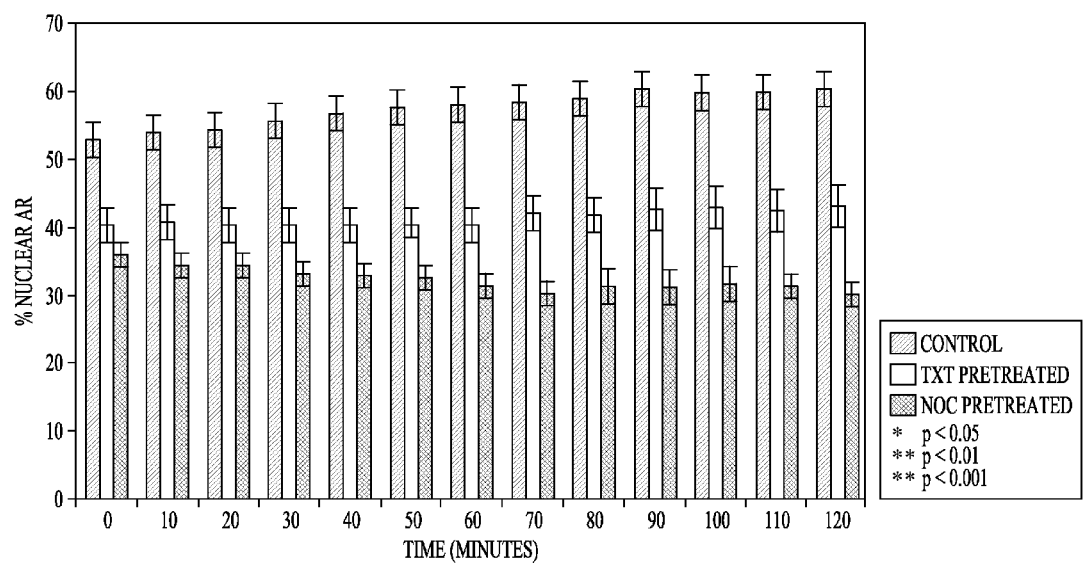

The integrity of the microtubule cytoskeleton was assessed in each condition prior to time lapse image acquisition and is shown in the right panels of FIGS. 8A and 8B, indicating effective drug-target engagement for each of the conditions. Microtubule bundling with docetaxel is shown in FIG. 8A-8B (middle row, arrowhead). Depolymerized tubulin upon nocodazole treatment is also shown in FIG. 8A-8B (third row).

Figure 8D:
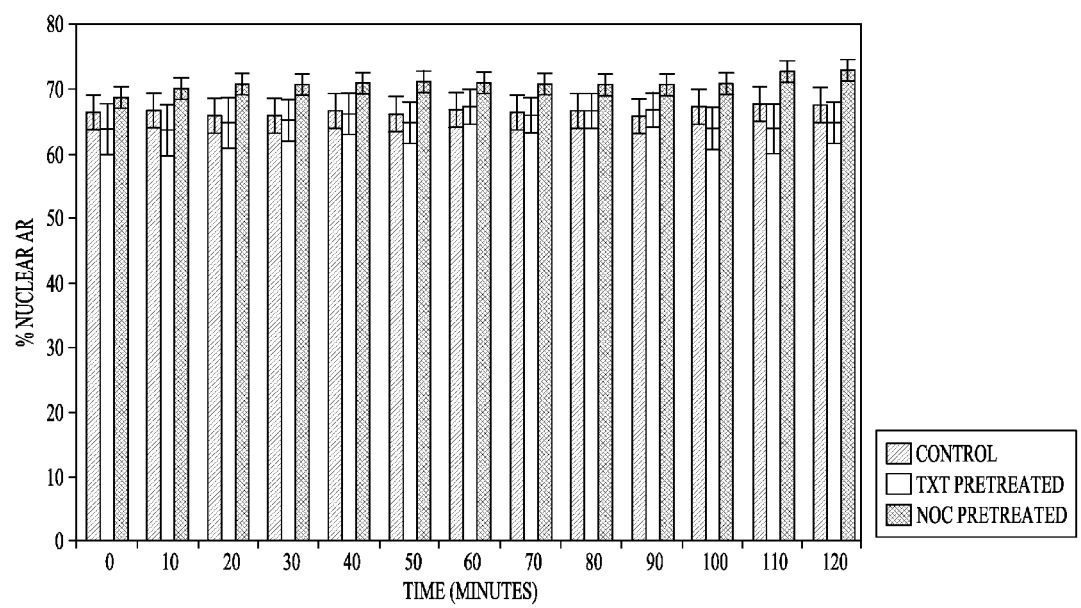

In contrast and despite effective drug-target engagement, drug treatment had no effect on the other clinically relevant and constitutively active androgen receptor splice variant, ARv7. Treatment of the ARv7-microinjected cells with microtubule targeting drugs did not impact this variant's nuclear localization at any time point (FIGS. 8B and 8D and Tables 2 and 3).

Taken together, these data indicate that the ARv5,6,7 variant, but not the ARv7, is dependent on microtubules for effective nuclear accumulation.

These studies were also performed on the M12 prostate cancer cell line, a tumorigenic cell line representative of the metastatic stage of prostate cancer. Isogenic cell lines were engineered to stably express GFP-tagged AR-wt AR, ARv5,6,7 or ARv7. The effects of docetaxel (TXT) treatment on the nuclear localization of each of the GFP-tagged receptors were then investigated in these M12 prostate cancer cells. As seen by the GFP fluorescence exhibited in FIG. 9A-9B), or antibody-based detection (FIG. 9F-9H), docetaxel inhibited ligand-induced AR-wt nuclear accumulation downstream of microtubule stabilization (FIG. 9A, arrowhead for microtubule bundles, arrows for cytoplasmic AR). Docetaxel treatment also inhibited the nuclear localization of the ligand-independent ARv5,6,7 variant (FIG. 9B). Similar results were obtained in the presence of R1881, which did not induce any further nuclear accumulation of ARv5,6,7 (FIG. 9I). However, as shown in FIG. 9C, docetaxel treatment failed to alter the nuclear localization of ARv7 variant in the absence or presence of R1881 (see also, FIG. 9J).

Figure 9D:
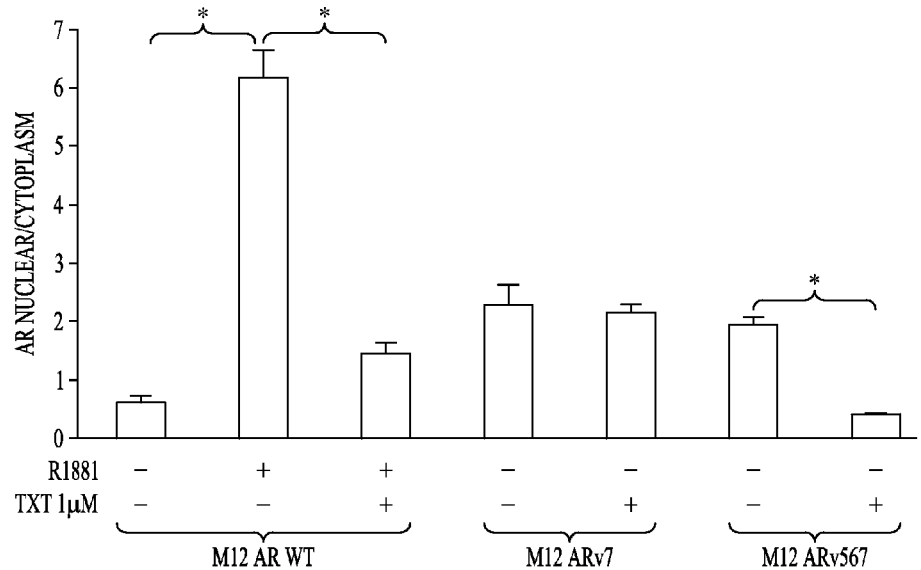

The extent of AR nuclear localization for each variant and condition was quantified by counting the number of cells with androgen receptor in the nucleus versus number of cells with cytoplasmic androgen receptor. FIG. 9D shows the ratio of cells in the nucleus:cytoplasm for cells having the wild type or variant androgen receptors under various drug exposure conditions. This analysis revealed that docetaxel treatment resulted in a significant decrease of nuclear localization in AR-wt and ARv5,6,7, but had no effect on ARv7. These data confirm and corroborate the live cell imaging results showing that ARv7 does not depend on microtubules for its nuclear trafficking.

Figure 9E:
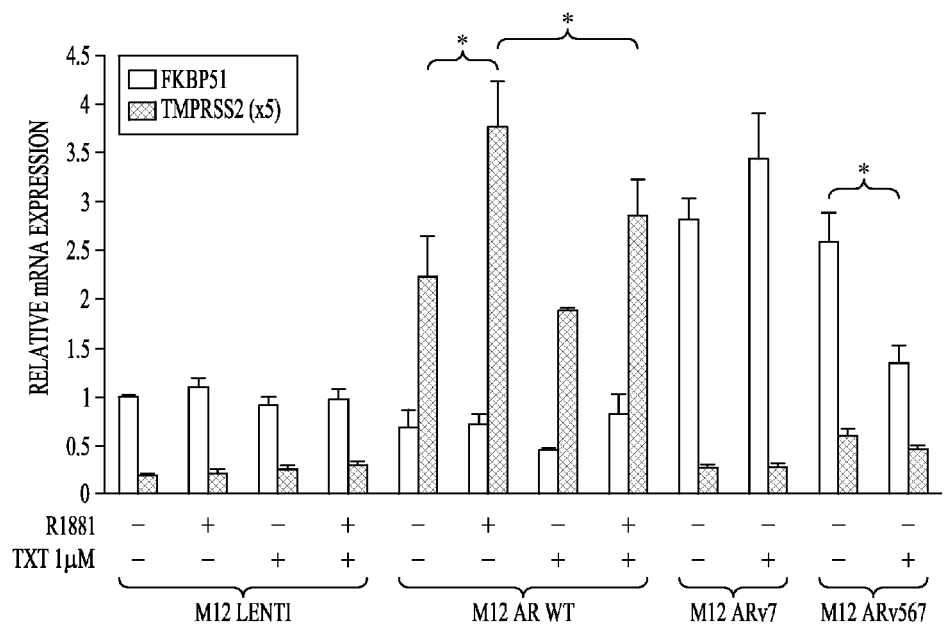
Figure 9F:
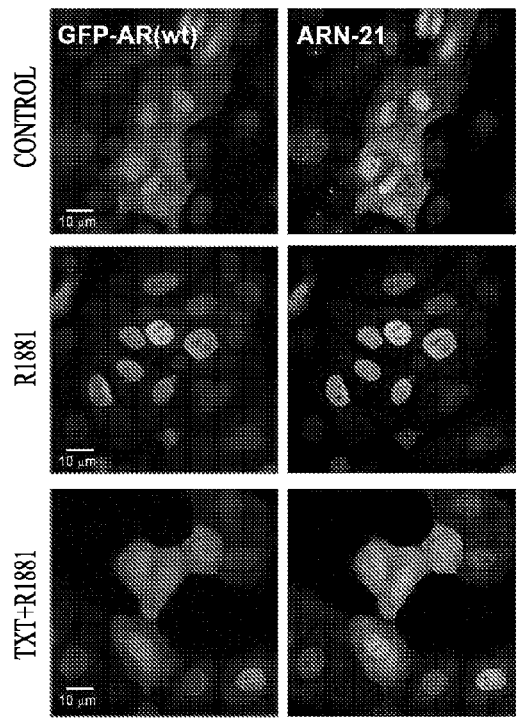
Figures 9G, 9H:
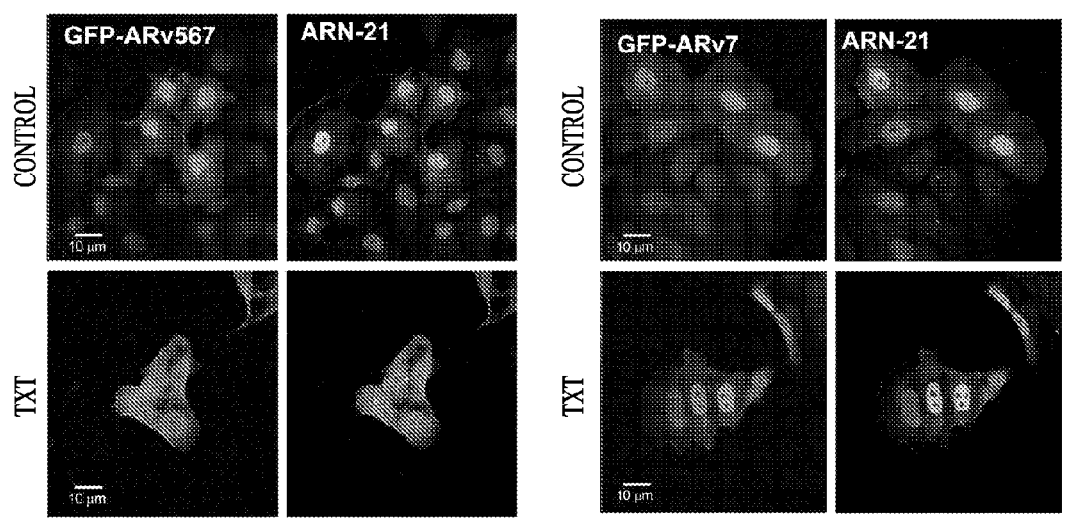

To assess the effect of docetaxel treatment on AR transcriptional activity quantitative real-time PCR was performed using transcriptional targets previously shown to be differentially induced by AR-wt and AR variants. Specifically TMPRSS2 was identified as a target specific for AR-wt while FKBP51 was transcriptionally activated by the AR variants. In this assay M12 cells expressing inducible AR-wt or variants were used. As seen in FIG. 9E, in M12 cells the AR-wt increased TMPRSS2 expression and docetaxel treatment significantly inhibited TMPRSS2 expression, consistent with the drug's effects on androgen receptor cytoplasmic sequestration. In the case of the AR variants, TMPRSS2 expression was no longer regulated while FKBP51 transcription was induced by both ARv7 and ARv5,6,7. Thus, docetaxel treatment significantly inhibited ARv5,6,7 mediated induction of FKBP51 but had no effect on ARv7 transcriptional activity, in agreement with the differential effects of docetaxel on each variant's nuclear localization (FIG. 9B-9C). These data confirm that the AR variants have a distinct transcriptome compared to AR-wt but that nuclear localization is necessary for AR-V and AR-wt activity.

Example 11

Dynamitin Overexpression Impairs ARv5,6,7 Nuclear Translocation, but has No Effect on ARv7

This Example describes experiments demonstrating that Dynamitin adversely affect Arv5,6,7 nuclear translocation but does not affect Arv7 nuclear translocation.

The data described in previous Examples indicate that a functional microtubule network is required for effective nuclear translocation of ARv5,6,7 variant, and for the AR-wt. In contrast, variant ARv7 behaves in a microtubule independent manner in all assays and cell lines tested.

To further dissect the mechanism regulating the cytoplasmic to nuclear translocation of each variant the involvement of the minus-end directed microtubule motor protein dynein was investigated, because the inventors have shown that dynein mediates nuclear translocation (Darshan et al., *Cancer Res* 71, 6019 (Sep. 15, 2011)). Dynein works in concert with several accessory proteins to drive subcellular motile functions including dynactin, which is an adapter that mediates the binding of dynein to cargo structures enhancing dynein's motor function. Overexpression of the dynactin associated protein, dynamitin, disrupts dynein-cargo interactions (Burkhardt et al., *J Cell Biol* 139, 469 (Oct. 20, 1997)). Such dynamitin overexpression was used in experiments to dissect the involvement of dynein in the transport of the androgen receptor splice variants to the nucleus.

Figures 10A, 10B:
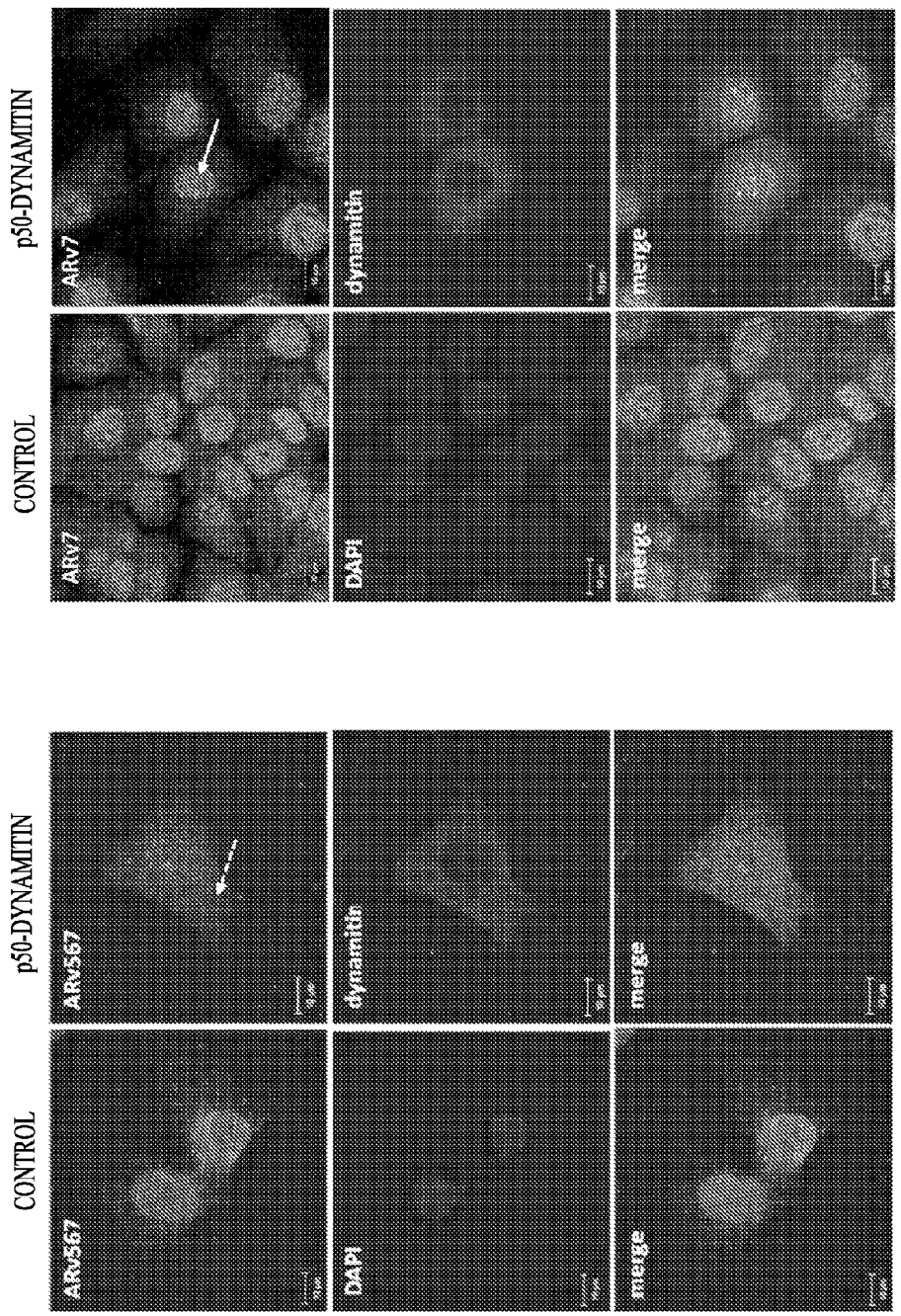
FIG. 10A shows images of M12 cells stably expressing untagged ARv5,6,7.
FIG. 10B shows images of M12 cells stably expressing untagged ARv7. The different cell types were transiently transfected with pCMVH50myc (encoding a c-Myc tagged human dynamitin). Cells were fixed, processed for double immunofluorescence labeling with anti-androgen receptor (lighter staining; green in the original) and c-Myc (darker staining; red in the original) antibodies and analyzed by confocal microscopy. Dashed arrows point to cytoplasmic androgen receptor protein and solid arrows to nuclear androgen receptor protein.
Figure 10C:
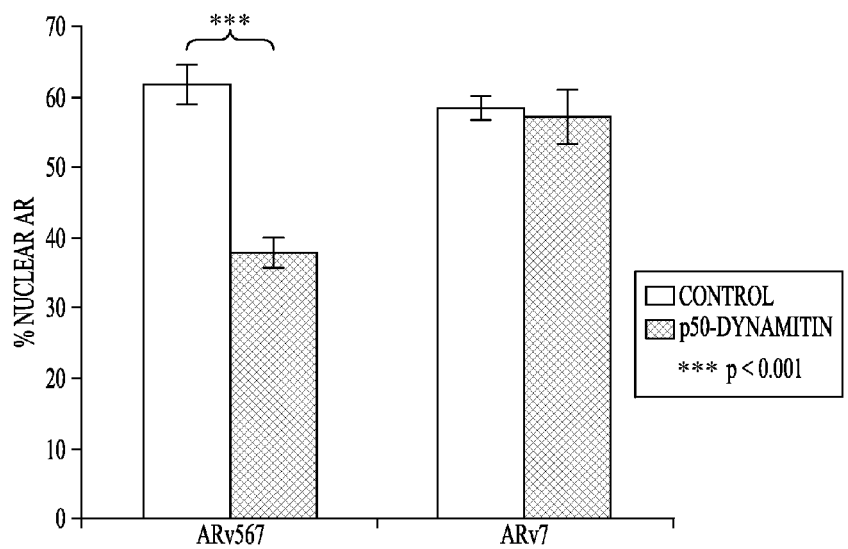
FIG. 10C is a bar graph illustrating the amount of each of the variants in the nucleus. Quantification was performed using Meta-Morph image analysis software. As illustrated, there is a marked decrease of nuclear ARv5,6,7 after dynein-cargo disruption. ARv7, however, remains unaffected by dynamitin overexpression.

M12 cells stably expressing untagged ARv5,6,7 (M12-ARv5,6,7) or ARv7 (M12-ARv7) were transiently transfected with a c-Myc-tagged p50-dynamitin vector and processed for double-labeling immunofluorescence with anti-androgen receptor and anti-c-Myc antibodies. Overexpression of dynamitin impaired nuclear accumulation of ARv5,6,7 (FIG. 10A, dashed arrows point to cytoplasmic androgen receptor). However, overexpression of dynamitin had no effect on the nuclear accumulation of ARv7 (FIG. 10B arrows point to nuclear androgen receptor). Quantification of the extent of nuclear accumulation of androgen receptor proteins revealed a significant decrease of ARv5,6,7 in the nucleus of dynamitin expressing cells as compared with dynamitin-overexpressing M12-ARv7 cells (FIG. 10C). However, no such effect was observed on the nuclear accumulation of ARv7 (FIG. 10C).

Figure 10D:
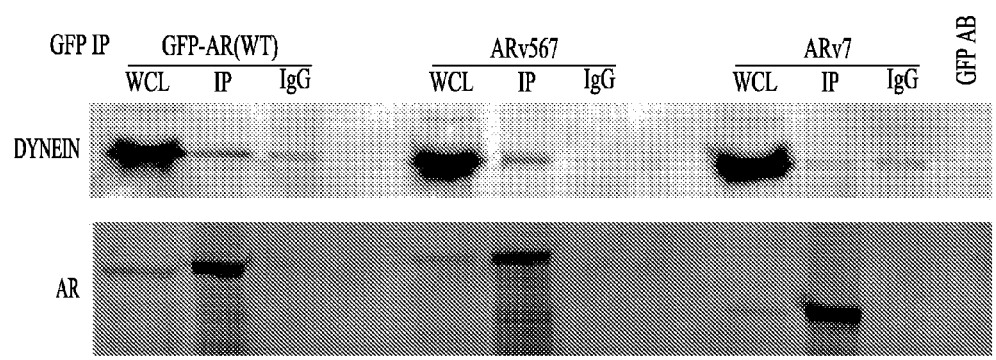
FIG. 10D shows electrophoretically separated immunoprecipitated protein from whole cell lysates of 293T cells that were transiently transfected with GFP-AR(wt), GFP-ARv5,6,7 and GFP-ARv7. The lysates were immunoprecipitated with a GFP antibody or control IgG and immunoblotted for dynein and androgen receptor.

To further investigate the role of the dynein microtubule-based motor protein on androgen receptor variant trafficking, a co-immunoprecipitation (co-IP) experiment was performed in HEK293T cells transiently transfected with GFP-tagged AR-wt AR, ARv5,6,7 or ARv7. Co-precipitation using an antibody against GFP revealed that both the AR-wt AR and ARv5,6,7, but not ARv7, associated with dynein (FIG. 10D).

Taken together these data support a model whereby AR-wt AR and ARv5,6,7 utilize microtubules and dynein-dependent transport for their nuclear accumulation and subsequent activity. On the other hand, ARv7 does not utilize this mechanism of transport and hence remains insensitive to taxane treatment.

Example 12

Docetaxel Treatment Inhibits ARv5,6,7-Mediated Subcutaneous Tumor Growth in SCID Mice This Example shows that Docetaxel is an effective antitumor agent for prostate cancer cells that express Arv5,6,7.

Recent work and the current data suggest that inhibition of the nuclear accumulation and transcriptional activity of androgen receptor is related, as least in part, to the clinical activity of taxanes. In order to determine the impact of androgen receptor variant expression on taxane sensitivity in vivo, the effects of docetaxel on the growth of two LuCaP xenograft tumors grown subcutaneously in SCID mice was evaluated (see Example 7 for a description of the methods employed).

Figure 11A:
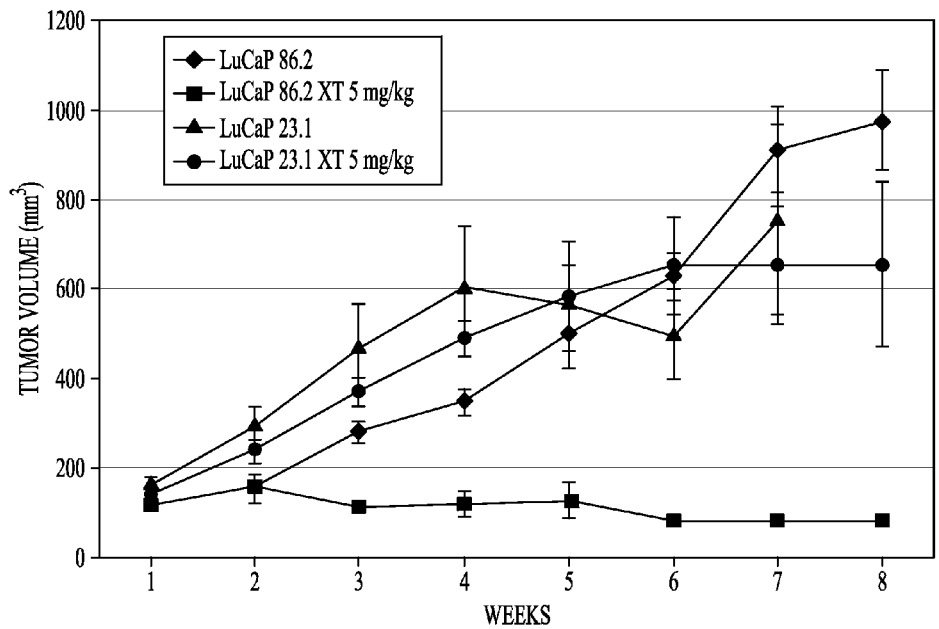
FIG. 11A-11C shows that docetaxel treatment inhibits ARv5,6,7-mediated subcutaneous tumor growth in SCID mice. Mice with human prostate cancer xenografts LuCap 86.2, expressing predominantly ARv5,6,7, and LuCap 23.12 expressing both AR(wt) and ARv7, were treated with docetaxel 5 mg/kg weekly intraperitoneally or with vehicle control. The study was terminated when all mice in the LuCaP 23.1 5 mg/kg group meet UW IACUC criteria for euthanasia. The Y axis shows tumor volumes+/−SEM, as a function of time (x-axis).
Figure 11B:
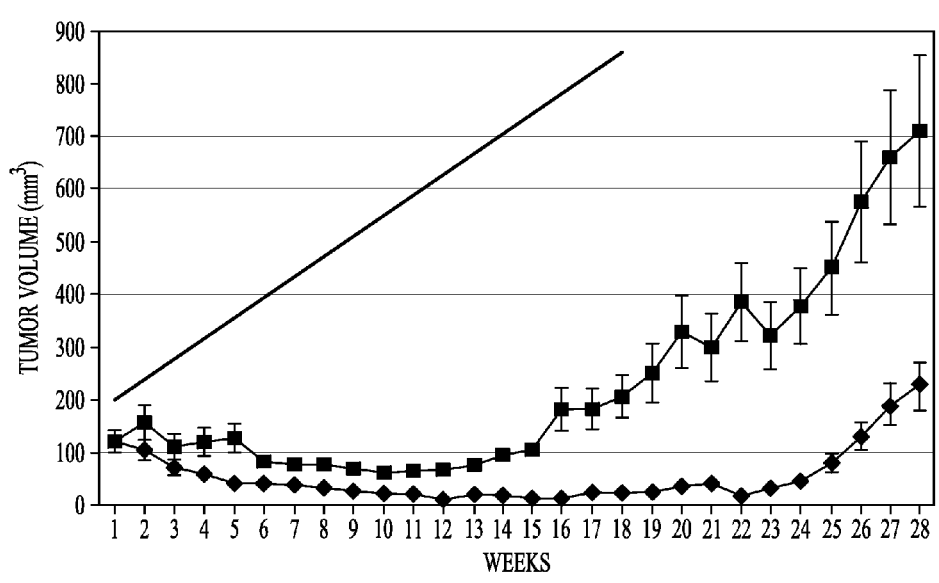
Figure 11C:
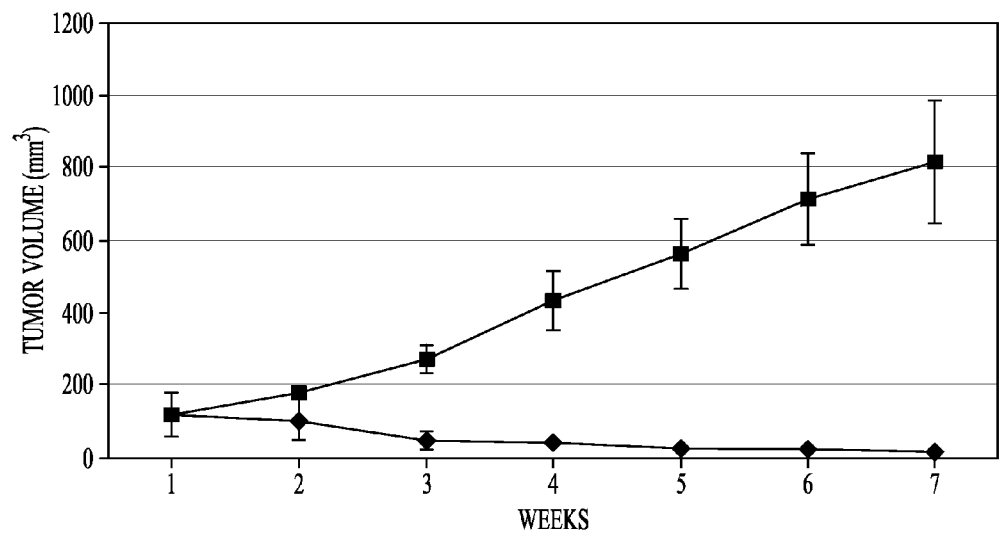

The tumors were LuCaP 86.2, a human xenograft tumor in which the majority of the androgen receptor is ARv5,6,7, and LuCaP 23.1, a human xenograft expressing both AR-wt and ARv7 (Mostaghel et al., *Clin Cancer Res* 17, 5913 (Sep. 15, 2011)). All xenografts were grown in non-castrate SCID mice. There were 15 mice in each group. LuCaP 86.2 tumor cells are resistant to castration. FIG. 11 indicates that LuCaP 86.2 tumor cells are driven by ARv5,6,7, because the growth of these cells is markedly suppressed by a low dose of docetaxel of 5 mg/kg (P<0.01 control vs. docetaxel treated). The inventors have previously shown that the 5 mg/kg dose of docetaxel is ineffective on the growth of LuCaP 35 xenograft expressing primarily AR-wt (Wu et al., *Clin Cancer Res* 12, 6153 (Oct. 15, 2006)). In contrast, there was no effect of docetaxel on the growth of LuCaP23.1 tumors (p=NS control vs. docetaxel treatment).

The effect of docetaxel treatment on androgen receptor nuclear accumulation was further assessed by immunohistochemistry on explanted LuCaP tumors, as previously described by Zhang et al. (*PLoS One* 6, e27970 (2011)). Quantitation of nuclear accumulation of androgen receptor protein in tumors from untreated versus treated animals revealed that docetaxel treatment resulted in a statistically significant reduction of nuclear androgen receptor in LuCaP86.2 tumors, while it had a minimal effect on LuCaP 23.1 tumors (FIGS. 10-11).

These data indicate that drug-induced inhibition of androgen receptor nuclear accumulation underlies taxane antitumor activity. These data also indicated that androgen receptor variant expression can determine whether a prostate cancer patient will respond to treatment with taxanes.

REFERENCES

1. J. Hoffman-Censits, W. K. Kelly, Enzalutamide: a novel antiandrogen for patients with castrate-resistant prostate cancer. *Clin Cancer Res* 19, 1335 (Mar. 15, 2013).

2. C. Tran et al., Development of a second-generation antiandrogen for treatment of advanced prostate cancer. *Science* 324, 787 (May 8, 2009).
3. J. S. de Bono et al., Abiraterone and increased survival in metastatic prostate cancer. *N Engl J Med* 364, 1995 (May 26, 2011).
4. P. S. Nelson, Molecular states underlying androgen receptor activation: a framework for therapeutics targeting androgen signaling in prostate cancer. *J Clin Oncol* 30, 644 (Feb. 20, 2012).
5. J. A. Locke et al., Androgen levels increase by intratumoral de novo steroidogenesis during progression of castration-resistant prostate cancer. *Cancer Res* 68, 6407 (Aug. 1, 2008).
6. C. D. Chen et al., Molecular determinants of resistance to antiandrogen therapy. *Nat Med* 10, 33 (January, 2004).
7. N. Nadiminty, A. C. Gao, Mechanisms of persistent activation of the androgen receptor in CRPC: recent advances and future perspectives. *World J Urol* 30, 287 (June, 2012).
8. D. P. Petrylak et al., Docetaxel and estramustine compared with mitoxantrone and prednisone for advanced refractory prostate cancer. *N Engl J Med* 351, 1513 (Oct. 7, 2004).
9. I. F. Tannock et al., Docetaxel plus prednisone or mitoxantrone plus prednisone for advanced prostate cancer. *N Engl J Med* 351, 1502 (Oct. 7, 2004).
10. M. S. Darshan et al., Taxane-induced blockade to nuclear accumulation of the androgen receptor predicts clinical responses in metastatic prostate cancer. *Cancer Res* 71, 6019 (Sep. 15, 2011).
11. M. L. Zhu et al., Tubulin-targeting chemotherapy impairs androgen receptor activity in prostate cancer. *Cancer Res* 70, 7992 (Oct. 15, 2010).
12. M. Thadani-Mulero, D. M. Nanus, P. Giannakakou, Androgen receptor on the move: boarding the microtubule expressway to the nucleus. *Cancer Res* 72, 4611 (Sep. 15, 2012).
13. J. Mezynski et al., Antitumour activity of docetaxel following treatment with the CYP17A1 inhibitor abiraterone: clinical evidence for cross-resistance? *Ann Oncol* 23, 2943 (November, 2012).
14. S. M. Dehm, L. J. Schmidt, H. V. Heemers, R. L. Vessella, D. J. Tindall, Splicing of a novel androgen receptor exon generates a constitutively active androgen receptor that mediates prostate cancer therapy resistance. *Cancer Res* 68, 5469 (Jul. 1, 2008).
15. Z. Guo et al., A novel androgen receptor splice variant is up-regulated during prostate cancer progression and promotes androgen depletion-resistant growth. *Cancer Res* 69, 2305 (Mar. 15, 2009).
16. R. Hu et al., Ligand-independent androgen receptor variants derived from splicing of cryptic exons signify hormone-refractory prostate cancer. *Cancer Res* 69, 16 (Jan. 1, 2009).
17. S. Sun et al., Castration resistance in human prostate cancer is conferred by a frequently occurring androgen receptor splice variant. *J Clin Invest* 120, 2715 (August, 2010).
18. E. A. Mostaghel et al., Resistance to CYP17A1 inhibition with abiraterone in castration-resistant prostate cancer: induction of steroidogenesis and androgen receptor splice variants. *Clin Cancer Res* 17, 5913 (Sep. 15, 2011).
19. Y. Li et al., Androgen receptor splice variants mediate enzalutamide resistance in castration-resistant prostate cancer cell lines. *Cancer Res* 73, 483 (Jan. 15, 2013).
20. E. Hornberg et al., Expression of androgen receptor splice variants in prostate cancer bone metastases is associated with castration-resistance and short survival. *PLoS One* 6, e19059 (2011).
21. L. Clinckemalie, D. Vanderschueren, S. Boonen, F. Claessens, The hinge region in androgen receptor control. *Mol Cell Endocrinol* 358, 1 (Jul. 6, 2012).
22. M. L. Cutress, H. C. Whitaker, I. G. Mills, M. Stewart, D. E. Neal, Structural basis for the nuclear import of the human androgen receptor. *J Cell Sci* 121, 957 (Apr. 1, 2008).
23. A. Haelens, T. Tanner, S. Denayer, L. Callewaert, F. Claessens, The hinge region regulates DNA binding, nuclear translocation, and transactivation of the androgen receptor. *Cancer Res* 67, 4514 (May 1, 2007).
24. Z. X. Zhou, M. Sar, J. A. Simental, M. V. Lane, E. M. Wilson, A ligand-dependent bipartite nuclear targeting signal in the human androgen receptor. Requirement for the DNA-binding domain and modulation by NH2-terminal and carboxyl-terminal sequences. *J Biol Chem* 269, 13115 (May 6, 1994).
25. P. A. Watson et al., Constitutively active androgen receptor splice variants expressed in castration-resistant prostate cancer require full-length androgen receptor. *Proc Natl Acad Sci USA* 107, 16759 (Sep. 28, 2010).
26. R. Hu et al., Distinct transcriptional programs mediated by the ligand-dependent full-length androgen receptor and its splice variants in castration-resistant prostate cancer. *Cancer Res* 72, 3457 (Jul. 15, 2012).
27. J. K. Burkhardt, C. J. Echeverri, T. Nilsson, R. B. Vallee, Overexpression of the dynamitin (p50) subunit of the dynactin complex disrupts dynein-dependent maintenance of membrane organelle distribution. *J Cell Biol* 139, 469 (Oct. 20, 1997).
28. J. D. Wu et al., Combined in vivo effect of A12, a type 1 insulin-like growth factor receptor antibody, and docetaxel against prostate cancer tumors. *Clin Cancer Res* 12, 6153 (Oct. 15, 2006).
29. X. Zhang et al., Androgen receptor variants occur frequently in castration resistant prostate cancer metastases. *PLoS One* 6, e27970 (2011).
30. N. L. Sharma et al., The androgen receptor induces a distinct transcriptional program in castration-resistant prostate cancer in man. *Cancer Cell* 23, 35 (Jan. 14, 2013).
31. L. R. Bohrer et al., FOXO1 binds to the TAU5 motif and inhibits constitutively active androgen receptor splice variants. *Prostate*, (Feb. 6, 2013).
32. S. N. Mediwala et al., The activity of the androgen receptor variant AR-V7 is regulated by FOXO1 in a PTEN-PI3K-AKT-dependent way. *Prostate* 73, 267 (Feb. 15, 2013).
33. F. Claessens et al., Diverse roles of androgen receptor (AR) domains in AR-mediated signaling. *Nucl Recept Signal* 6, e008 (2008).
34. S. M. Dehm, D. J. Tindall, Alternatively spliced androgen receptor variants. *Endocr Relat Cancer* 18, R183 (October, 2011).
35. T. M. Tanner et al., A 629RKLKK633 motif in the hinge region controls the androgen receptor at multiple levels. *Cell Mol Life Sci* 67, 1919 (June, 2010).
36. S. C. Chan, Y. Li, S. M. Dehm, Androgen receptor splice variants activate androgen receptor target genes and support aberrant prostate cancer cell growth independent of canonical androgen receptor nuclear localization signal. *J Biol Chem* 287, 19736 (Jun. 1, 2012).

37. B. J. Kirby et al., Functional characterization of circulating tumor cells with a prostate-cancer-specific microfluidic device. *PLoS One* 7, e35976 (2012).
38. P. Giannakakou et al., p53 is associated with cellular microtubules and is transported to the nucleus by dynein. *Nat Cell Biol* 2, 709 (October, 2000).
39. Maheswaran S, Haber D A (2010) Circulating tumor cells: a window into cancer biology and metastasis. Current opinion in genetics & development 20: 96-99.
40. Zieglschmid V, Hollmann C, Bocher 0 (2005) Detection of disseminated tumor cells in peripheral blood. Critical reviews in clinical laboratory sciences 42: 155-196.
41. Racila E, Euhus D, Weiss A J, Rao C, McConnell J, et al. (1998) Detection and characterization of carcinoma cells in the blood. Proceedings of the National Academy of Sciences of the United States of America 95: 4589-4594.
42. Krivacic R T, Ladanyi A, Curry D N, Hsieh H B, Kuhn P, et al. (2004) A rare-cell detector for cancer. Proceedings of the National Academy of Sciences of the United States of America 101: 10501-10504.
43. Pantel K, Brakenhoff R H, Brandt B (2008) Detection, clinical relevance and specific biological properties of disseminating tumour cells. Nature reviews Cancer 8: 329-340.
44. Riethdorf S, Pantel K (2010) Advancing personalized cancer therapy by detection and characterization of circulating carcinoma cells. Annals of the New York Academy of Sciences 1210: 66-77.
45. Nagrath S, Sequist L V, Maheswaran S, Bell D W, Irimia D, et al. (2007) Isolation of rare circulating tumour cells in cancer patients by microchip technology. Nature 450: 1235-1239.
46. Stott S L, Hsu C H, Tsukrov D I, Yu M, Miyamoto D T, et al. (2010) Isolation of circulating tumor cells using a microvortex-generating herringbone-chip. Proceedings of the National Academy of Sciences of the United States of America 107: 18392-18397.
47. Stott S L, Lee R J, Nagrath S, Yu M, Miyamoto D T, et al. (2010) Isolation and characterization of circulating tumor cells from patients with localized and metastatic prostate cancer. Science translational medicine 2: 25ra23.
48. Gleghorn J P, Pratt E D, Denning D, Liu H, Bander N H, et al. (2010) Capture of circulating tumor cells from whole blood of prostate cancer patients using geometrically enhanced differential immunocapture (GEDI) and a prostate-specific antibody. Lab on a chip 10: 27-29.
49. Mani S A, Guo W, Liao M J, Eaton E N, Ayyanan A, et al. (2008) The epithelial-mesenchymal transition generates cells with properties of stem cells. Cell 133: 704-715.
50. Polyak K, Weinberg R A (2009) Transitions between epithelial and mesenchymal states: acquisition of malignant and stem cell traits. Nature reviews Cancer 9: 265-273.
51. Munz M, Baeuerle P A, Gires O (2009) The emerging role of EpCAM in cancer and stem cell signaling. Cancer research 69: 5627-5629.
52. Gostner J M, Fong D, Wrulich O A, Lehne F, Zitt M, et al. (2011) Effects of EpCAM overexpression on human breast cancer cell lines. BMC cancer 11: 45.
53. Gradilone A, Raimondi C, Nicolazzo C, Petracca A, Gandini O, et al. (2011) Circulating tumour cells lacking cytokeratin in breast cancer: the importance of being mesenchymal. Journal of cellular and molecular medicine 15: 1066-1070.
54. Coumans F A, Doggen C J, Attard G, de Bono J S, Terstappen L W (2010) All circulating EpCAM+CK+CD45− objects predict overall survival in castration-resistant prostate cancer. Annals of oncology: official journal of the European Society for Medical Oncology/ESMO 21: 1851-1857.
55. Danila D C, Heller G, Gignac G A, Gonzalez-Espinoza R, Anand A, et al. (2007) Circulating tumor cell number and prognosis in progressive castration-resistant prostate cancer. Clinical cancer research: an official journal of the American Association for Cancer Research 13: 7053-7058.
56. Scher H I, Jia X, de Bono J S, Fleisher M, Pienta K J, et al. (2009) Circulating tumour cells as prognostic markers in progressive, castration-resistant prostate cancer: a reanalysis of IMMC38 trial data. The lancet oncology 10: 233-239.
57. Veldscholte J, Ris-Stalpers C, Kuiper G G, Jenster G, Berrevoets C, et al. (1990) A mutation in the ligand binding domain of the androgen receptor of human LNCaP cells affects steroid binding characteristics and response to anti-androgens. Biochemical and biophysical research communications 173: 534-540.
58. Park K, Tomlins S A, Mudaliar K M, Chiu Y L, Esgueva R, et al. (2010) Antibody-based detection of ERG rearrangement-positive prostate cancer. Neoplasia 12: 590-598.
59. de Bono J S, Oudard S, Ozguroglu M, Hansen S, Machiels J P, et al. (2010) Prednisone plus cabazitaxel or mitoxantrone for metastatic castration-resistant prostate cancer progressing after docetaxel treatment: a randomised open-label trial. Lancet 376: 1147-1154.
60. Petrylak D P, Tangen C M, Hussain M H, Lara P N, Jr., Jones J A, et al. (2004) Docetaxel and estramustine compared with mitoxantrone and prednisone for advanced refractory prostate cancer. The New England journal of medicine 351: 1513-1520.
61. Tannock I F, de Wit R, Berry W R, Horti J, Pluzanska A, et al. (2004) Docetaxel plus prednisone or mitoxantrone plus prednisone for advanced prostate cancer. The New England journal of medicine 351: 1502-1512.
62. Marcus A I, Peters U, Thomas S L, Garrett S, Zelnak A, et al. (2005) Mitotic kinesin inhibitors induce mitotic arrest and cell death in Taxol-resistant and -sensitive cancer cells. The Journal of biological chemistry 280: 11569-11577.
63. Extra J M, Rousseau F, Bruno R, Clavel M, Le Bail N, et al. (1993) Phase I and pharmacokinetic study of Taxotere (RP 56976; NSC 628503) given as a short intravenous infusion. Cancer research 53: 1037-1042.
64. Yu M, Stott S, Toner M, Maheswaran S, Haber D A (2011) Circulating tumor cells: approaches to isolation and characterization. The Journal of cell biology 192: 373-382.
65. Cristofanilli M, Budd G T, Ellis M J, Stopeck A, Matera J, et al. (2004) Circulating tumor cells, disease progression, and survival in metastatic breast cancer. The New England journal of medicine 351: 781-791.
66. Cohen S J, Punt C J, Iannotti N, Saidman B H, Sabbath K D, et al. (2008) Relationship of circulating tumor cells to tumor response, progression-free survival, and overall survival in patients with metastatic colorectal cancer. Journal of clinical oncology: official journal of the American Society of Clinical Oncology 26: 3213-3221.
67. de Bono J S, Scher H I, Montgomery R B, Parker C, Miller M C, et al. (2008) Circulating tumor cells predict survival benefit from treatment in metastatic castration- 68. Wicha M S, Hayes D F (2011) Circulating tumor cells: not all detected cells are bad and not all bad cells are detected. Journal of clinical oncology: official journal of the American Society of Clinical Oncology 29: 1508-1511.
69. Attard G, de Bono J S (2011) Utilizing circulating tumor cells: challenges and pitfalls. Current opinion in genetics & development 21: 50-58.
70. Harris L, Fritsche H, Mennel R, Norton L, Ravdin P, et al. (2007) American Society of Clinical Oncology 2007 update of recommendations for the use of tumor markers in breast cancer. Journal of clinical oncology: official journal of the American Society of Clinical Oncology 25: 5287-5312.
71. Danila D C, Fleisher M, Scher H I (2011) Circulating tumor cells as biomarkers in prostate cancer. Clinical cancer research: an official journal of the American Association for Cancer Research 17: 3903-3912.
72. Haber D A, Gray N S, Baselga J (2011) The evolving war on cancer. Cell 145: 19-24.
73. Bander N H, Nanus D M, Milowsky M I, Kostakoglu L, Vallabahajosula S, et al. (2003) Targeted systemic therapy of prostate cancer with a monoclonal antibody to prostate-specific membrane antigen. Seminars in oncology 30: 667-676.
74. Horoszewicz J S, Kawinski E, Murphy G P (1987) Monoclonal antibodies to a new antigenic marker in epithelial prostatic cells and serum of prostatic cancer patients. Anticancer research 7: 927-935.
75. Israeli R S, Powell C T, Corr J G, Fair W R, Heston W D (1994) Expression of the prostate-specific membrane antigen. Cancer research 54: 1807-1811.
76. Israeli R S, Miller W H, Jr., Su S L, Powell C T, Fair W R, et al. (1994) Sensitive nested reverse transcription polymerase chain reaction detection of circulating prostatic tumor cells: comparison of prostate-specific membrane antigen and prostate-specific antigen-based assays. Cancer research 54: 6306-6310.
77. Ananias H J, van den Heuvel M C, Helfrich W, de Jong I J (2009) Expression of the gastrin-releasing peptide receptor, the prostate stem cell antigen and the prostate-specific membrane antigen in lymph node and bone metastases of prostate cancer. The Prostate 69: 1101-1108.
78. Perner S, Hofer M D, Kim R, Shah R B, Li H, et al. (2007) Prostate-specific membrane antigen expression as a predictor of prostate cancer progression. Human pathology 38: 696-701.
79. Chang S S, Reuter V E, Heston W D, Bander N H, Grauer L S, et al. (1999) Five different anti-prostate-specific membrane antigen (PSMA) antibodies confirm PSMA expression in tumor-associated neovasculature. Cancer research 59: 3192-3198.
80. Silver D A, Pellicer I, Fair W R, Heston W D, Cordon-Cardo C (1997) Prostate-specific membrane antigen expression in normal and malignant human tissues. Clinical cancer research: an official journal of the American Association for Cancer Research 3: 81-85.
81. Haffner M C, Kronberger I E, Ross J S, Sheehan C E, Zitt M, et al. (2009) Prostate-specific membrane antigen expression in the neovasculature of gastric and colorectal cancers. Human pathology 40: 1754-1761.
82. Troyer J K, Beckett M L, Wright G L, Jr. (1995) Detection and characterization of the prostate-specific membrane antigen (PSMA) in tissue extracts and body fluids. International journal of cancer Journal international du cancer 62: 552-558.
83. Sokoloff R L, Norton K C, Gasior C L, Marker K M, Grauer L S (2000) A dual-monoclonal sandwich assay for prostate-specific membrane antigen: levels in tissues, seminal fluid and urine. The Prostate 43: 150-157.
84. Scher H I, Jia X, Chi K, de Wit R, Berry W R, et al. (2011) Randomized, open-label phase III trial of docetaxel plus high-dose calcitriol versus docetaxel plus prednisone for patients with castration-resistant prostate cancer. Journal of clinical oncology: official journal of the American Society of Clinical Oncology 29: 2191-2198.
85. Tomlins S A, Rhodes D R, Perner S, Dhanasekaran S M, Mehra R, et al. (2005) Recurrent fusion of TMPRSS2 and ETS transcription factor genes in prostate cancer. Science 310: 644-648.
86. Clark J, Attard G, Jhavar S, Flohr P, Reid A, et al. (2008) Complex patterns of ETS gene alteration arise during cancer development in the human prostate. Oncogene 27: 1993-2003.
87. Attard G, Jameson C, Moreira J, Flohr P, Parker C, et al. (2009) Hormone-sensitive prostate cancer: a case of ETS gene fusion heterogeneity. Journal of clinical pathology 62: 373-376.
88. Meng S, Tripathy D, Frenkel E P, Shete S, Naftalis E Z, et al. (2004) Circulating tumor cells in patients with breast cancer dormancy. Clinical cancer research: an official journal of the American Association for Cancer Research 10: 8152-8162.
89. Komlodi-Pasztor E, Sackett D, Wilkerson J, Fojo T (2011) Mitosis is not a key target of microtubule agents in patient tumors. Nature reviews Clinical oncology 8: 244-250.
90. Jordan M A, Wilson L (2004) Microtubules as a target for anticancer drugs. Nature reviews Cancer 4: 253-265.
91. McDaid H M, Mani S, Shen H J, Muggia F, Sonnichsen D, et al. (2002) Validation of the pharmacodynamics of BMS-247550, an analogue of epothilone B, during a phase I clinical study. Clinical cancer research: an official journal of the American Association for Cancer Research 8: 2035-2043.
92. Darshan M S, Loftus M S, Thadani-Mulero M, Levy B P, Escuin D, et al. (2011) Taxane-Induced Blockade to Nuclear Accumulation of the Androgen Receptor Predicts Clinical Responses in Metastatic Prostate Cancer. Cancer research.

All patents and publications referenced or mentioned herein (as well as those listed in Appendix A) are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following statements summarize and describe aspects of the invention.

Statements:

1. A method of determining whether a prostate cancer patient can benefit from taxane drug treatment comprising testing whether an androgen receptor splice selected from the group consisting of variant v5,6,7, variant v7, or a combination thereof is present in a test sample obtained from the patient.
2. The method of statement 1, wherein the prostate cancer patient can benefit from taxane drug treatment when androgen receptor splice variant v5,6,7 is present in a test sample than variant v7.
3. The method of statement 1 or 2, wherein the prostate cancer patient may not benefit from taxane drug treatment when androgen receptor splice variant v7 is present in a test sample than variant v5,6,7.
4. The method of any of statements 1-3, wherein the test sample comprises circulating tumor cells, a prostate tissue sample, a blood sample, a serum sample, ascites fluid, a urine sample, semen sample, or a combination thereof.
5. The method of any of statements 1-4, further comprising capturing circulating tumor cells from the test sample before the testing.
6. The method of any of statements 1-5, further comprising capturing circulating tumor cells from the test sample in a microfluidic device.
7. The method of any of statements 1-6, further comprising capturing circulating tumor cells from the test sample in a microfluidic device that comprises a solid support with a length and width, a cover sheet, and rows of posts between the solid support and the covers sheet, the device configured for flow of a cell sample through the length of the device from a cell sample application area, to an outlet; wherein each row is perpendicular to the length of the device; and where the posts of one row do not align with the posts of adjacent rows.
8. The method of any of statements 1-7, further comprising capturing circulating tumor cells from the test sample in a microfluidic device comprising rows posts, each row is perpendicular to the length of the device, wherein the posts in each row do not align with the posts of one or two adjacent rows.
9. The method of any of statements 1-8, further comprising capturing circulating tumor cells from the test sample in a microfluidic device comprising rows posts, each row is perpendicular to the length of the device, wherein the posts in each row are offset from the posts in the one or two adjacent rows by 0.1 to 100 microns, or about 0.2 to 75 microns, or about 0.5 to 50 microns, or about 0.75 to 10 microns, or about 1 microns to about 25 microns.
10. The method of any of statements 1-9, further comprising capturing circulating tumor cells from the test sample in a microfluidic device comprising a solid support and/or the cover sheet can comprises include silicon, silica, glass, polydimethylsiloxane (PDMA), cellulose, ethylcellulose, methylcellulose, nitrocellulose, hydroxypropylcellulose, hydroxypropyl methylcellulose, polystyrene, polyethylene, nylon, rayon, cotton, teflon, mica, sephadex, sepharose, polyacrylonitrile, glass, glass-fiber paper, gold, metal, paper, and combinations thereof.
11. The method of any of statements 6-10, wherein a binding entity is immobilized on at least a section of the solid support, the cover sheet, or a combination thereof.
12. The method of statement 11, wherein the binding entity specifically binds to a selected cell type.
13. The method of statement 11 or 12, wherein the binding entity is an anti-PMSA antibody.
14. The method of any of statements 1-13, further comprising capturing circulating tumor cells from the test sample in a microfluidic device, and testing captured circulating tumor cells in the microfluidic device.
15. The method of any of statements 1-14, further comprising capturing circulating tumor cells from the test sample in a microfluidic device, removing captured circulating tumor cells from the device and testing captured circulating tumor cells.
16. The method of any of statements 1-15, wherein testing comprises detection of one or more androgen receptor variant proteins.
17. The method of any of statements 1-16, wherein testing comprises quantification of one or more androgen receptor variant proteins to generate quantified level of androgen receptor variant expression for each androgen receptor variant protein.
18. The method of any of statements 1-17, wherein testing comprises quantification of one or more androgen receptor variant proteins to generate quantified level of androgen receptor variant expression for each androgen receptor variant protein, and comparison of one or more quantified level of androgen receptor variant expression to a control expression level of the same androgen receptor variant.
19. The method of any of statements 1-18, wherein the androgen receptor splice variant v5,6,7 protein has at least 75% sequence identity, or at least 80% sequence identity, or at least 85% sequence identity, or at least 90%, or at least 95% sequence identity to SEQ ID NO:3.
20. The method of any of statements 1-19, wherein the androgen receptor splice variant v7 protein has at least 75% sequence identity, or at least 80% sequence identity, or at least 85% sequence identity, or at least 90%, or at least 95% sequence identity to SEQ ID NO:5.

21. The method of any of statements 1-20, wherein testing comprises an assay of the test sample with an antibody specific for the androgen receptor variant protein.

22. The method of any of statements 1-21, wherein testing comprises an assay comprising contacting the test sample with an antibody having at least 50% or greater selectivity, or 60% greater selectivity, or 70% greater selectivity, or 80% greater selectivity, or 85% greater selectivity, or 90% greater selectivity, or 95% greater selectivity for the androgen receptor splice variant.

23. The method of any of statements 1-22, wherein testing comprises an assay comprising contacting the test sample with an antibody and detecting a signal from a conjugate of the antibody and the androgen receptor variant protein, if binding between the antibody and the androgen receptor variant protein occurs.

24. The method of any of statements 1-23, wherein testing comprises an assay comprising contacting the test sample with an antibody and detecting a signal from a conjugate of the antibody and the androgen receptor variant protein within cells from the test sample, if binding between the antibody and the androgen receptor variant protein occurs.

25. The method of any of statements 1-24, wherein testing comprises an assay comprising contacting the test sample with an antibody and detecting a signal from a conjugate of the antibody and the androgen receptor variant protein within nuclei of cells from the test sample, if binding between the antibody and the androgen receptor variant protein occurs.

26. The method of any of statements 1-25, wherein testing comprises an assay comprising contacting the test sample with an antibody and detecting a signal from a conjugate of the antibody, the androgen receptor variant protein, and cellular microtubules from the test sample cells, if binding between the antibody and the androgen receptor variant protein occurs.

27. The method of any of statements 1-26, wherein testing comprises an assay comprising contacting the test sample with an antibody and detecting a signal from a conjugate of the antibody and the androgen receptor variant protein within cytoplasm of cells from the test sample, if binding between the antibody and the androgen receptor variant protein occurs.

28. The method of any of statements 1-27, wherein testing comprises an assay comprising contacting the test sample with an antibody and a taxane, and detecting a signal from a conjugate of the antibody and the androgen receptor variant protein within cells from the test sample, if binding between the antibody and the androgen receptor variant protein occurs.

29. The method of any of statements 1-28, wherein testing comprises an assay comprising contacting the test sample with an antibody and a taxane, and detecting whether a signal from a conjugate of the antibody and the androgen receptor variant protein is localized within cell nuclei of the test sample.

30. The method of any of statements 1-29, wherein testing comprises an assay comprising contacting the test sample with a directly or indirectly labeled antibody.

31. The method of any of statements 1-30, wherein testing comprises an immunoassay selected from the group consisting of an immunoassay, cell sorting assay, sandwich immunoassay, competition inhibition immunoassay, ELISA (Enzyme-Linked Immunosorbent Assay), immunohistochemical assay, agglutination assay, precipitation assay, radioimmunoassay or antigen-down immunoassay, immunometric assay, competitive binding assay, a direct sandwich immunoassay, an indirect sandwich assay, an immunoprecipitation assay, a nuclear immunostaining assay, an immunoblot assay, or a combination thereof.

32. The method of any of statements 1-15, wherein testing comprises detection of the androgen receptor variant transcript.

33. The method of any of statements 1-15 or 32, wherein testing comprises Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, in situ hybridization, nucleic acid amplification, reverse transcription, polymerase chain reaction, quantitative real time polymerase chain reaction (qRT-PCR), or a combination thereof.

34. The method of any of statements 1-15, 32 or 33, wherein testing comprises an assay comprising contacting the test sample with at least one probe or primer that selectively hybridizes to the androgen receptor splice variant mRNA.

35. The method of any of statements 1-15, 32-34, wherein testing comprises an assay comprising contacting the test sample with at least one probe or primer that selectively hybridizes to the androgen receptor splice variant mRNA, wherein the probe or primer is covalently attached to a label that can emit a detectable signal.

36. The method of any of statements 1-15, 32-35, wherein testing comprises an assay comprising contacting the test sample with at least one probe or primer that selectively hybridizes to the androgen receptor splice variant mRNA, wherein hybridization of the probe or the primer to the androgen receptor splice variant mRNA emits a signal.

37. The method of any of statements 1-15, 32-36, wherein testing comprises an assay comprising contacting the test sample with at least one probe or primer that selectively hybridizes to the androgen receptor splice variant mRNA, wherein primer extension of the androgen receptor splice variant mRNA emits a signal.

38. The method of any of statements 1-15, 32-37, wherein testing comprises an assay comprising contacting the test sample with at least one probe or primer that can hybridize to the androgen receptor splice variant mRNA under high stringency hybridization conditions.

39. The method of any of statements 1-15, 32-38, wherein testing comprises an assay comprising contacting the test sample with at least one probe or primer that can hybridize to the androgen receptor splice variant mRNA under high stringency hybridization conditions comprising a wash in 0.1×SSPE, 1.0% SDS at a temperature of at least 42° C.

40. The method of any of statements 1-15, 32-39, wherein testing comprises quantification of one or more androgen receptor variant mRNAs to generate quantified level of androgen receptor variant expression for each androgen receptor variant mRNA.

41. The method of any of statements 1-15, 32-40, wherein testing comprises quantification of one or more androgen receptor variant mRNAs to generate a quantified level of androgen receptor variant expression for each androgen receptor variant mRNA, and comparison of one or more quantified level of androgen receptor variant expression to a control expression level of the same androgen receptor variant.

42. The method of statement 41, wherein control expression level of the same androgen receptor variant is the expression level of the same androgen receptor variant in non-tumor prostate cells.

43. The method of any of statements 1-15, 32-42 wherein testing comprises quantification of androgen receptor variant v5,6,7 mRNA to generate a quantified level of androgen receptor variant v5,6,7 expression level, and comparison of the quantified level of androgen receptor variant v5,6,7 expression level to a quantified level of androgen receptor variant v7.

44. The method of any of statements 1-15, 32-43 wherein testing comprises quantification of androgen receptor variant v7 mRNA to generate a quantified level of androgen receptor variant v7 expression level, and comparison of the quantified level of androgen receptor variant v7 expression level to a quantified level of androgen receptor variant v5,6,7.

45. The method of any of statements 1-44, wherein a patient is responsive to taxane administration when a quantified level of androgen receptor variant v5,6,7 expression in the patient's test sample is greater than a quantified level of androgen receptor variant v7 expression in the patient's test sample.

46. The method of any of statements 1-45, wherein a patient is non-responsive to taxane administration when a quantified level of androgen receptor variant v7 expression in the patient's test sample is greater than a quantified level of androgen receptor variant v5,6,7 expression in the patient's test sample.

47. The method of any of statements 1-15, wherein testing comprises detection of a gene product or a gene transcript regulated by the androgen receptor splice variant in the test sample.

48. The method of any of statements 1-15 or 47, wherein the gene product or the gene transcript regulated by the androgen receptor splice variant is from AKT1, BAG1, Beta-catenin, BRCA1, C-jun, Calmodulin 1, Caveolin 1, CDK9, COX5B, CREB-binding protein, Cyclin D1, Cyclin-dependent kinase 7, Death associated protein 6, Deleted in Colorectal Cancer, EFCAB6, Epidermal growth factor receptor, FOXO1, GAPDH, Gelsolin, GNB2L1, GSK3B, HDAC1, HSP90AA1, HTATIP, MAGEA11, MED1, MYST2, NCOA1, NCOA2, NCOA3, NCOA4, NCOA6, NCOR2, NONO, PA2G4, PAK6, PATZ1, PIAS2, PRPF6, PTEN, RAD9A, RANBP9, RCHY1, Retinoblastoma protein, RNF15, RNF4, SART3, SMAD3, Small heterodimer partner, Src, SRY, STAT3, SVIL, Testicular receptor 2, Testicular receptor 4, TGFB1I1, TMF1, TRIM68, UBE2I, UXT, ZMIZ1, and any combination thereof.

49. The method of any of statements 1-15, 47 or 48, wherein testing comprises quantification of a selected gene product or a selected gene transcript regulated by the androgen receptor splice variant in the test sample to generate a quantified regulated selected gene expression level, and comparison of the quantified regulated selected gene expression level to a control expression level of the selected regulated gene.

50. The method of statement 49, wherein control expression level of the selected regulated gene is the expression level of the selected gene in non-tumor prostate cells.

51. The method of any of statements 1-50, further comprising administering a taxane to a patient when more androgen receptor splice variant v5,6,7 is present in the patient's test sample than variant v7.

52. The method of statement 51, wherein the taxane is paclitaxel, docetaxel, cabazitaxel, baccatin III, 10-deacetyl-baccatin, hongdoushan A, hongdoushan B, hongdoushan C, or any combination thereof.

53. A microfluidic device for capturing circulating tumor cells, comprising a solid support with a length and width, a cover sheet, and rows of posts between the solid support and the cover sheet, the device configured for flow of a cell sample through the length of the device from a cell sample application area, to an outlet; wherein each row is perpendicular to the length of the device; and where the posts of one row do not align with the posts of adjacent rows.

54. The device of statement 53, wherein each row is perpendicular to the length of the device, and wherein the posts in each row do not align with the posts of one or two adjacent rows.

55. The device of statement 53 or 54, wherein each row is perpendicular to the length of the device, and wherein the posts in each row are offset from the posts in the one or two adjacent rows by 0.1 to 100 microns, or about 0.2 to 75 microns, or about 0.5 to 50 microns, or about 0.75 to 10 microns, or about 1 microns to about 25 microns.

56. The device of any of statements 53-55, wherein the solid support and/or the cover sheet can comprise include silicon, silica, glass, polydimethylsiloxane (PDMA), cellulose, ethylcellulose, methylcellulose, nitrocellulose, hydroxypropylcellulose, hydroxypropyl methylcellulose, polystyrene, polyethylene, nylon, rayon, cotton, teflon, mica, sephadex, sepharose, polyacrylonitrile, glass, glass-fiber paper, gold, metal, paper, and combinations thereof.

57. The device of any of statements 53-56, wherein a binding entity is immobilized on at least a section of the solid support, the cover sheet, or a combination thereof.

58. The device of statement 57, wherein the binding entity specifically binds to a selected cell type.

59. The device of statement 58, wherein the binding entity is an anti-PMSA antibody.

60. A kit comprising instructions for use of the kit components, and any of the following separately packaged components:
(a) at least one probe or primer that specifically binds to and androgen receptor variant v5,6,7, or v7;
(b) a binding entity that specifically binds to and androgen receptor variant v5,6,7, or v7;
(c) the device of any of statements 50-57; or
(d) any combination thereof.

61. The kit of statement 60, wherein the probe or primer specifically binds to and androgen receptor variant v5,6,7 under high stringency conditions.

62. The kit of statement 60 or 61, wherein the probe or primer specifically binds to and androgen receptor variant v7 under high stringency conditions.

63. The kit of any of statements 60-62, further comprising at least one probe, primer or binding entity that specifically binds to full length androgen receptor.

64. The kit of any of statements 60-63, wherein the instructions describe use of the kit components for isolation of circulating tumor cells, immunoassay, cell sorting assay, sandwich immunoassay, competition inhibition immunoassay, ELISA (Enzyme-Linked Immunosorbent Assay), immunohistochemical assay, agglutination assay, precipitation assay, radioimmunoassay or antigen-down immunoassay, immunometric assay, competitive binding assay, a direct sandwich immunoassay, an indirect sandwich assay, an immunoprecipitation assay, a nuclear immunostaining assay, an immunoblot assay, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, in situ hybridization, nucleic acid amplification, reverse transcription, polymerase chain reaction, quantitative real time polymerase chain reaction (qRT-PCR), or a combination thereof.

65. The kit of any of statements 60-64, further comprising at least one vial, needle, syringe, finger-prick device, alcohol swab, gauze square, cotton ball, bandage, latex glove, incubation tray, adhesive label, or data reporting sheet.

66. The kit of any of statements 60-65, further comprising a container comprising a taxane composition.

67. The kit of statement 66, wherein the taxane is paclitaxel, docetaxel, cabazitaxel, baccatin III, 10-deacetylbaccatin, hongdoushan A, hongdoushan B, hongdoushan C, or any combination thereof.

68. A method of determining whether a prostate cancer patient can benefit from taxane drug treatment comprising testing whether an androgen receptor splice variant v5,6,7 is present in a test sample obtained from the patient.

69. The method of statement 68, wherein the androgen receptor splice variant v5,6,7 has SEQ ID NO:3.

70. The method of statement 68 or 69, wherein the test sample is a bodily fluid (e.g. blood) or a tissue sample from the patient.

71. The method of any of statements 68-70, wherein the testing comprises an assay that comprises contacting an antibody specific for the androgen receptor splice variant v5,6,7 with the test sample to form a test mixture, and detecting whether androgen receptor splice variant v5,6,7 binds to the antibody.

72. The method of any of statements 68-71, wherein the testing comprises contacting the test sample with a device comprising an antibody specific for the androgen receptor splice variant v5,6,7 and detecting whether androgen receptor splice variant v5,6,7 binds to the antibody.

73. The method of statement 71 or 72, further comprising separating unbound material from the antibody.

74. The method of any of statements 71-73, further comprising contacting the test mixture or the device with a labeling agent capable of binding to a complex formed between the antibody and androgen receptor splice variant v5,6,7.

75. The method of statement 74, wherein the agent does not detectably bind to the antibody when androgen receptor splice variant v5,6,7 is not bound to the antibody.

76. The method of any of statements 68-75, further comprising administering a taxanes drug to the patient when androgen receptor splice variant v5,6,7 is present in a test sample obtained from the patient.

77. A device comprising a solid surface and an antibody immobilized thereon, wherein the antibody is specific for androgen receptor splice variant v5,6,7, or for androgen receptor splice variant v7.

78. The device of statement 77, wherein the device is configured for flow of a test sample through the device and binding of a cell expressing androgen receptor splice variant v5,6,7 or for androgen receptor splice variant v7 to the antibody.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treating a prostate cancer patient comprising:
   quantifying expression of androgen receptor splice variant v5,6,7, with at least 95% sequence identity to SEQ ID NO:3, in a test sample obtained from the patient;
   quantifying expression of androgen receptor splice variant v7 with at least 95% sequence identity to SEQ ID NO:5 in the test sample; and
   administering a taxane if the quantity of androgen receptor v5,6,7 splice variant is greater than the quantity of androgen receptor splice variant v7 the test sample;
   but not administering a taxane if more androgen receptor splice variant v7 with at least 95% sequence identity to SEQ ID NO:5 is present in a test sample than variant v5,6,7.

2. The method of claim 1, wherein the test sample comprises circulating tumor cells, a prostate tissue sample, a blood sample, a serum sample, ascites fluid, a urine sample, semen sample, or a combination thereof.

3. The method of claim 1, further comprising capturing circulating tumor cells from the test sample before the testing.

4. The method of claim 1, further comprising capturing circulating tumor cells from the test sample in a microfluidic device.

5. The method of claim 1, wherein quantifying comprises an immunoassay, cell sorting assay, sandwich immunoassay, competition inhibition immunoassay, ELISA (Enzyme-Linked Immunosorbent Assay), immunohistochemical assay, agglutination assay, precipitation assay, radioimmunoassay or antigen-down immunoassay, immunometric assay, competitive binding assay, a direct sandwich immunoassay, an indirect sandwich assay, an immunoprecipitation assay, a nuclear immunostaining assay, an immunoblot assay, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays, combined reverse transcription/nucleic acid amplification, nuclease protection, Serial Analysis Gene Expression (SAGE), next generation sequencing, gene expression microarray, in situ hybridization, nucleic acid amplification, reverse transcription, polymerase chain reaction, quantitative real time polymerase chain reaction (qRT-PCR), or a combination thereof.

6. The method of claim 1 wherein the taxane is paclitaxel, docetaxel, cabazitaxel, baccatin III, 10-deacetylbaccatin, hongdoushan A, hongdoushan B, hongdoushan C, or any combination thereof.

7. The method of claim 1, further comprising quantifying the expression of full androgen receptor with at least 95% sequence identity to SEQ ID NO: 1 in the test sample.

* * * * *

SEQUENCE LISTING

```
<160> NUMBER OF SEQ ID NOS: 17

<210> SEQ ID NO 1
<211> LENGTH: 919
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
 1               5                  10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
            85                  90                  95
```

-continued

Ala His Arg Arg Gly Pro Thr Gly Tyr Leu Val Leu Asp Glu Glu Gln
            100                 105                110

Gln Pro Ser Gln Pro Gln Ser Ala Leu Glu Cys His Pro Glu Arg Gly
            115                 120                125

Cys Val Pro Glu Pro Gly Ala Ala Val Ala Ala Ser Lys Gly Leu Pro
            130                 135                140

Gln Gln Leu Pro Ala Pro Pro Asp Glu Asp Ser Ala Ala Pro Ser
145                 150                 155                160

Thr Leu Ser Leu Leu Gly Pro Thr Phe Pro Gly Leu Ser Ser Cys Ser
                165                 170                175

Ala Asp Leu Lys Asp Ile Leu Ser Glu Ala Ser Thr Met Gln Leu Leu
            180                 185                190

Gln Gln Gln Gln Gln Glu Ala Val Ser Glu Gly Ser Ser Ser Gly Arg
            195                 200                205

Ala Arg Glu Ala Ser Gly Ala Pro Thr Ser Ser Lys Asp Asn Tyr Leu
            210                 215                220

Gly Gly Thr Ser Thr Ile Ser Asp Asn Ala Lys Glu Leu Cys Lys Ala
225                 230                 235                240

Val Ser Val Ser Met Gly Leu Gly Val Glu Ala Leu Glu His Leu Ser
                245                 250                255

Pro Gly Glu Gln Leu Arg Gly Asp Cys Met Tyr Ala Pro Leu Leu Gly
            260                 265                270

Val Pro Pro Ala Val Arg Pro Thr Pro Cys Ala Pro Leu Ala Glu Cys
            275                 280                285

Lys Gly Ser Leu Leu Asp Asp Ser Ala Gly Lys Ser Thr Glu Asp Thr
            290                 295                300

Ala Glu Tyr Ser Pro Phe Lys Gly Gly Tyr Thr Lys Gly Leu Glu Gly
305                 310                 315                320

Glu Ser Leu Gly Cys Ser Gly Ser Ala Ala Gly Ser Ser Gly Thr
                325                 330                335

Leu Glu Leu Pro Ser Thr Leu Ser Leu Tyr Lys Ser Gly Ala Leu Asp
            340                 345                350

Glu Ala Ala Ala Tyr Gln Ser Arg Asp Tyr Tyr Asn Phe Pro Leu Ala
            355                 360                365

Leu Ala Gly Pro Pro Pro Pro Pro Pro Pro His Pro His Ala Arg
            370                 375                380

Ile Lys Leu Glu Asn Pro Leu Asp Tyr Gly Ser Ala Trp Ala Ala Ala
385                 390                 395                400

Ala Ala Gln Cys Arg Tyr Gly Asp Leu Ala Ser Leu His Gly Ala Gly
            405                 410                415

Ala Ala Gly Pro Gly Ser Gly Pro Ser Ala Ala Ser Ser Ser
            420                 425                430

Trp His Thr Leu Phe Thr Ala Glu Glu Gly Gln Leu Tyr Gly Pro Cys
            435                 440                445

Gly Gly Gly Gly Gly Gly Gly Gly Gly Gly Gly Gly Gly
            450                 455                460

Gly Gly Gly Gly Gly Gly Gly Glu Ala Gly Ala Val Ala Pro Tyr
465                 470                 475                480

Gly Tyr Thr Arg Pro Pro Gln Gly Leu Ala Gly Gln Glu Ser Asp Phe
            485                 490                495

Thr Ala Pro Asp Val Trp Tyr Pro Gly Gly Met Val Ser Arg Val Pro
            500                 505                510

```
Tyr Pro Ser Pro Thr Cys Val Lys Ser Glu Met Gly Pro Trp Met Asp
            515                 520                 525

Ser Tyr Ser Gly Pro Tyr Gly Asp Met Arg Leu Glu Thr Ala Arg Asp
    530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
    595                 600                 605

Lys Asn Cys Pro Ser Cys Arg Leu Arg Lys Cys Tyr Glu Ala Gly Met
610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Thr Thr
                645                 650                 655

Gln Lys Leu Thr Val Ser His Ile Glu Gly Tyr Glu Cys Gln Pro Ile
                660                 665                 670

Phe Leu Asn Val Leu Glu Ala Ile Glu Pro Gly Val Val Cys Ala Gly
            675                 680                 685

His Asp Asn Asn Gln Pro Asp Ser Phe Ala Ala Leu Leu Ser Ser Leu
    690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
                740                 745                 750

Ser Phe Thr Asn Val Asn Ser Arg Met Leu Tyr Phe Ala Pro Asp Leu
    755                 760                 765

Val Phe Asn Glu Tyr Arg Met His Lys Ser Arg Met Tyr Ser Gln Cys
770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
                820                 825                 830

Asn Tyr Ile Lys Glu Leu Asp Arg Ile Ile Ala Cys Lys Arg Lys Asn
    835                 840                 845

Pro Thr Ser Cys Ser Arg Arg Phe Tyr Gln Leu Thr Lys Leu Leu Asp
850                 855                 860

Ser Val Gln Pro Ile Ala Arg Glu Leu His Gln Phe Thr Phe Asp Leu
865                 870                 875                 880

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
                900                 905                 910

Pro Ile Tyr Phe His Thr Gln
                915
```

```
<210> SEQ ID NO 2
<211> LENGTH: 3568
<212> TYPE: DNA
<213> ORGANISM: Homo sapiens

<400> SEQUENCE: 2
taataactca gttcttattt gcacctactt cagtggacac tgaatttgga aggtggagga      60
ttttgttttt ttcttttaag atctgggcat cttttgaatc tacccttcaa gtattaagag     120
acagactgtg agcctagcag ggcagatctt gtccaccgtg tgtcttcttc tgcacgagac     180
tttgaggctg tcagagcgct ttttgcgtgg ttgctcccgc aagtttcctt ctctggagct     240
tcccgcaggt gggcagctag ctgcagcgac taccgcatca tcacagcctg ttgaactctt     300
ctgagcaaga gaaggggagg cggggtaagg gaagtaggtg aagattcag ccaagctcaa      360 ggatggaagt gcagttaggg ctgggaaggg tctaccctcg gccgccgtcc aagacctacc     420
gaggagcttt ccagaatctg ttccagagcg tgcgcgaagt gatccagaac ccgggcccca     480
ggcacccaga ggccgcgagc gcagcacctc ccggcgccag tttgctgctg ctgcagcagc     540
agcagcagca gcagcagcag cagcagcagc agcagcagca gcagcagcag cagcaagaga     600
ctagccccag gcagcagcag cagcagcagg gtgaggatgg ttctccccaa gcccatcgta     660
gaggccccac aggctacctg gtcctggatg aggaacagca accttcacag ccgcagtcgg     720
ccctggagtg ccaccccgag agaggttgcg tcccagagcc tggagccgcc gtggccgcca     780
gcaaggggct gccgcagcag ctgccagcac ctccggacga ggatgactca gctgccccat     840
ccacgttgtc cctgctgggc ccacttttcc ccggcttaag cagctgctcc gctgaccttg     900
aagacatcct gagcgaggcc agcaccatgc aactccttca gcaacagcag caggaagcag     960
tatccgaagg cagcagcagc gggagagcga ggaggcctc gggggctccc acttcctcca    1020
aggacaatta cttagggggc acttcgacca tttctgacaa cgccaaggag ttgtgtaagg    1080
cagtgtcggt gtccatgggc ctgggtgtgg aggcgttgga gcatctgagt ccaggggaac    1140
agcttcgggg ggattgcatg tacgccccac ttttgggagt tccacccgct gtgcgtccca    1200
ctccttgtgc cccattggcc gaatgcaaag gttctctgct agacgacagc gcaggcaaga    1260
gcactgaaga tactgctgag tattcccctt tcaaggggag ttacaccaaa gggctagaag    1320
gcgagagcct aggctgctct ggcagcgctg cagcagggag ctccgggaca cttgaactgc    1380
cgtctaccct gtctctctac aagtccgag cactggacga ggcagctgcg taccagagtc    1440
gcgactacta caactttcca ctggctctgg ccggaccgcc gccccctccg ccgcctcccc    1500
atccccacgc tcgcatcaag ctggagaacc cgctggacta cggcagcgcc tggggcggctg   1560 cggcggcgca gtgccgctat ggggacctgg cgagcctgca tggcgcgggt gcagcgggac    1620
ccggttctgg gtcaccctca gccgccgctt cctcatcctg gcacactctc ttcacagccg    1680
aagaaggcca gttgtatgga ccgtgtggtg gtggtggggg tggtggcggc ggcggcggcg    1740
gcggcggcgg cggcggcggc ggcggcggcg gcggcggcga ggcgggagct gtagccccct    1800
acggctacac tcggcccccct caggggctgg cgggccagga aagcgacttc accgcacctg    1860
atgtgtggta ccctggcggc atggtgagca gagtgcccta tcccagtccc acttgtgtca    1920
aaagcgaaat gggcccctgg atggatagct actccgacc ttacgggac atgcgtttgg      1980 agactgccag ggaccatgtt ttgcccattg actattactt tccaccccag aagacctgcc    2040
tgatctgtgg agatgaagct tctggtgtgc actatggagc tctcacatgt ggaagctgca    2100
aggtcttctt caaaagagcc gctgaaggga aacagaagta cctgtgcgcc agcagaaatg    2160
```

```
attgcactat tgataaattc cgaaggaaaa attgtccatc ttgtcgtctt cggaaatgtt    2220
atgaagcagg gatgactctg ggagcccgga agctgaagaa acttggtaat ctgaaactac    2280
aggaggaagg agaggcttcc agcaccacca gccccactga ggagacaacc cagaagctga    2340
cagtgtcaca cattgaaggc tatgaatgtc agcccatctt tctgaatgtc ctggaagcca    2400
ttgagccagg tgtagtgtgt gctggacacg acaacaacca gcccgactcc tttgcagcct    2460
tgctctctag cctcaatgaa ctgggagaga dacagcttgt acacgtggtc aagtgggcca    2520
aggccttgcc tggcttccgc aacttacacg tggacgacca gatggctgtc attcagtact    2580
cctggatggg gctcatggtg tttgccatgg gctggcgatc cttcaccaat gtcaactcca    2640
ggatgctcta cttcgcccct gatctggttt tcaatgagta ccgcatgcac aagtcccgga    2700
tgtacagcca gtgtgtccga atgaggcacc tctctcaaga gtttggatgg ctccaaatca    2760
ccccccagga attcctgtgc atgaaagcac tgctactctt cagcattatt ccagtggatg    2820
ggctgaaaaa tcaaaaattc tttgatgaac ttcgaatgaa ctacatcaag gaactcgatc    2880
gtatcattgc atgcaaaaga aaaaatccca catcctgctc aagacgcttc taccagctca    2940
ccaagctcct ggactccgtg cagcctattg cgagagagct gcatcagttc acttttgacc    3000
tgctaatcaa gtcacacatg gtgagcgtgg actttccgga aatgatggca gagatcatct    3060
ctgtgcaagt gcccaagatc ctttctggga aagtcaagcc catctatttc cacacccagt    3120
gaagcattgg aaaccctatt tccccacccc agctcatgcc ccctttcaga tgtcttctgc    3180
ctgttataac tctgcactac tcctctgcag tgccttgggg aatttcctct attgatgtac    3240
agtctgtcat gaacatgttc ctgaattcta tttgctgggc ttttttttc tctttctctc    3300 cttctttttt cttcttccct ccctatctaa ccctcccatg gcaccttcag actttgcttc    3360
ccattgtggc tcctatctgt gttttgaatg gtgttgtatg ctttaaatct gtgatgatcc    3420
tcatatggcc cagtgtcaag ttgtgcttgt ttacagcact actctgtgcc agccacacaa    3480
acgtttactt atcttatgcc acgggaagtt tagagagcta agattatctg gggaaatcaa    3540
aacaaaaaac aagcaaacaa aaaaaaaa                                       3568

<210> SEQ ID NO 3
<211> LENGTH: 739
<212> TYPE: PRT
<213> ORGANISM: Homo sapiens

<400> SEQUENCE: 3

Met Glu Val Gln Leu Gly Leu Gly Arg Val Tyr Pro Arg Pro Pro Ser
 1               5                  10                  15

Lys Thr Tyr Arg Gly Ala Phe Gln Asn Leu Phe Gln Ser Val Arg Glu
             20                  25                  30

Val Ile Gln Asn Pro Gly Pro Arg His Pro Glu Ala Ala Ser Ala Ala
         35                  40                  45

Pro Pro Gly Ala Ser Leu Leu Leu Leu Gln Gln Gln Gln Gln Gln Gln
     50                  55                  60

Gln Gln Gln Gln Gln Gln Gln Gln Gln Gln Gln Gln Gln Gln Gln Gln
 65                  70                  75                  80

Gln Glu Thr Ser Pro Arg Gln Gln Gln Gln Gln Gly Glu Asp Gly
             85                  90                  95

Ser Pro Gln Ala His Arg Arg Gly Pro Thr Gly Tyr Leu Val Leu Asp
            100                 105                 110

Glu Glu Gln Gln Pro Ser Gln Pro Gln Ser Ala Leu Glu Cys His Pro
            115                 120                 125
```

```
Glu Arg Gly Cys Val Pro Glu Pro Gly Ala Val Ala Ala Ser Lys
    130                 135                 140

Gly Leu Pro Gln Gln Leu Pro Ala Pro Pro Asp Glu Asp Ser Ala
145                 150                 155                 160

Ala Pro Ser Thr Leu Ser Leu Leu Gly Pro Thr Phe Pro Gly Leu Ser
                165                 170                 175

Ser Cys Ser Ala Asp Leu Lys Asp Ile Leu Ser Glu Ala Ser Thr Met
                180                 185                 190

Gln Leu Leu Gln Gln Gln Gln Gln Glu Ala Val Ser Glu Gly Ser Ser
            195                 200                 205

Ser Gly Arg Ala Arg Glu Ala Ser Gly Ala Pro Thr Ser Ser Lys Asp
210                 215                 220

Asn Tyr Leu Gly Gly Thr Ser Thr Ile Ser Asp Asn Ala Lys Glu Leu
225                 230                 235                 240

Cys Lys Ala Val Ser Val Ser Met Gly Leu Gly Val Glu Ala Leu Glu
                245                 250                 255

His Leu Ser Pro Gly Glu Gln Leu Arg Gly Asp Cys Met Tyr Ala Pro
                260                 265                 270

Leu Leu Gly Val Pro Pro Ala Val Arg Pro Thr Pro Cys Ala Pro Leu
            275                 280                 285

Ala Glu Cys Lys Gly Ser Leu Leu Asp Asp Ser Ala Gly Lys Ser Thr
290                 295                 300

Glu Asp Thr Ala Glu Tyr Ser Pro Phe Lys Gly Gly Tyr Thr Lys Gly
305                 310                 315                 320

Leu Glu Gly Glu Ser Leu Gly Cys Ser Gly Ser Ala Ala Ala Gly Ser
                325                 330                 335

Ser Gly Thr Leu Glu Leu Pro Ser Thr Leu Ser Leu Tyr Lys Ser Gly
            340                 345                 350

Ala Leu Asp Glu Ala Ala Ala Tyr Gln Ser Arg Asp Tyr Tyr Asn Phe
            355                 360                 365

Pro Leu Ala Leu Ala Gly Pro Pro Pro Pro Pro Pro Pro His Pro
            370                 375                 380

His Ala Arg Ile Lys Leu Glu Asn Pro Leu Asp Tyr Gly Ser Ala Trp
385                 390                 395                 400

Ala Ala Ala Ala Ala Gln Cys Arg Tyr Gly Asp Leu Ala Ser Leu His
                405                 410                 415

Gly Ala Gly Ala Ala Gly Pro Gly Ser Gly Ser Pro Ser Ala Ala Ala
                420                 425                 430

Ser Ser Ser Trp His Thr Leu Phe Thr Ala Glu Glu Gly Gln Leu Tyr
            435                 440                 445

Gly Pro Cys Gly Gly Gly Gly Gly Gly Gly Gly Gly Gly Gly Gly Gly
        450                 455                 460

Gly Gly Gly Gly Gly Gly Gly Gly Gly Gly Gly Gly Gly Gly Glu Ala
465                 470                 475                 480

Gly Ala Val Ala Pro Tyr Gly Tyr Thr Arg Pro Pro Gln Gly Leu Ala
                485                 490                 495

Gly Gln Glu Ser Asp Phe Thr Ala Pro Asp Val Trp Tyr Pro Gly Gly
            500                 505                 510

Met Val Ser Arg Val Pro Tyr Pro Ser Pro Thr Cys Val Lys Ser Glu
            515                 520                 525

Met Gly Pro Trp Met Asp Ser Tyr Ser Gly Pro Tyr Gly Asp Met Arg
530                 535                 540
```

```
Leu Glu Thr Ala Arg Asp His Val Leu Pro Ile Asp Tyr Tyr Phe Pro
545                 550                 555                 560

Pro Gln Lys Thr Cys Leu Ile Cys Gly Asp Glu Ala Ser Gly Cys His
                565                 570                 575

Tyr Gly Ala Leu Thr Cys Gly Ser Cys Lys Val Phe Phe Lys Arg Ala
            580                 585                 590

Ala Glu Gly Lys Gln Lys Tyr Leu Cys Ala Ser Arg Asn Asp Cys Thr
        595                 600                 605

Ile Asp Lys Phe Arg Arg Lys Asn Cys Pro Ser Cys Arg Leu Arg Lys
    610                 615                 620

Cys Tyr Glu Ala Gly Met Thr Leu Gly Ala Arg Lys Leu Lys Lys Leu
625                 630                 635                 640

Gly Asn Leu Lys Leu Gln Glu Glu Gly Glu Ala Ser Ser Thr Thr Ser
                645                 650                 655

Pro Thr Glu Glu Thr Thr Gln Lys Leu Thr Val Ser His Ile Glu Gly
                660                 665                 670

Tyr Glu Cys Gln Pro Ile Phe Leu Asn Val Leu Glu Ala Ile Glu Pro
            675                 680                 685

Gly Val Val Cys Ala Gly His Asp Asn Asn Gln Pro Asp Ser Phe Ala
        690                 695                 700

Ala Leu Leu Ser Ser Leu Asn Glu Leu Gly Glu Arg Gln Leu Val His
705                 710                 715                 720

Val Val Lys Trp Ala Lys Ala Leu Pro Asp Cys Glu Arg Ala Ala Ser
                725                 730                 735

Val His Phe

<210> SEQ ID NO 4
<211> LENGTH: 2442
<212> TYPE: DNA
<213> ORGANISM: Homo sapiens

<400> SEQUENCE: 4
aggatggaag tgcagttagg gctgggaagg gtctaccctc ggccgccgtc caagacctac      60
cgaggagctt tccagaatct gttccagagc gtgcgcgaag tgatccagaa cccgggcccc     120
aggcacccag aggccgcgag cgcagcacct cccggcgcca gtttgctgct gctgcagcag     180
cagcagcagc agcagcagca gcagcagcag cagcagcagc agcagcagca gcagcagcag     240
cagcaagaga ctagccccag gcagcagcag cagcagcagg gtgaggatgg ttctcccaa      300 gcccatcgta gaggccccac aggctacctg gtcctggatg aggaacagca accttcacag     360
ccgcagtcgg ccctggagtg ccaccccgag agaggttgcg tcccagagcc tggagccgcc     420
gtggccgcca gcaaggggct gccgcagcag ctgccagcac ctccggacga ggatgactca     480
gctgccccat ccacgttgtc cctgctgggc cccactttcc ccggcttaag cagctgctcc     540
gctgacctta agacatcct gagcgaggcc agcaccatgc aactcctca gcaacagcag     600 caggaagcag tatccgaagg cagcagcagc gggagagcga gggaggcctc ggggctccc     660 acttcctcca aggacaatta cttaggggc acttcgacca tttctgacaa cgccaaggag     720
ttgtgtaagg cagtgtcggt gtccatgggc ctggtgtgg aggcgttgga gcatctgagt     780
ccaggggaac agcttcgggg ggattgcatg tacgccccac ttttgggagt tccaccgct     840 gtgcgtccca ctccttgtgc cccattggcc gaatgcaaag gttctctgct agacgacagc     900
gcaggcaaga gcactgaaga tactgctgag tattcccctt tcaagggagg ttacaccaaa     960
gggctagaag gcgagagcct aggctgctct ggcagcgctg cagcagggag ctccgggaca    1020
```

```
cttgaactgc cgtctaccct gtctctctac aagtccggag cactggacga ggcagctgcg    1080
taccagagtc gcgactacta caactttcca ctggctctgg ccggaccgcc gccccctccg    1140
ccgcctcccc atccccacgc tcgcatcaag ctggagaacc cgctggacta cggcagcgcc    1200
tgggcggctg cggcggcgca gtgccgctat ggggacctgg cgagcctgca tggcgcgggt    1260
gcagcgggac ccggttctgg gtcaccctca gccgccgctt cctcatcctg cacactctc     1320 ttcacagccg aagaaggcca gttgtatgga ccgtgtggtg gtggtggggg tggtggcggc    1380
ggcggcggcg gcggcggcgg cggcggcggc ggcggcggcg gcggcggcgg cggcggcgag    1440
gcgggagctg tagccccta cggctacact cggcccctc aggggctggc gggccaggaa      1500
agcgacttca ccgcacctga tgtgtggtac cctggcggca tggtgagcag agtgccctat    1560
cccagtccca cttgtgtcaa aagcgaaatg ggcccctgga tggatagcta ctccggacct    1620
tacggggaca tgcgtttgga gactgccagg gaccatgttt tgcccattga ctattacttt    1680 ccacccccaga agacctgcct gatctgtgga gatgaagctt ctgggtgtca ctatggagct    1740
ctcacatgtg aagctgcaa ggtcttcttc aaaagagccg ctgaagggaa acagaagtac     1800
ctgtgcgcca gcagaaatga ttgcactatt gataaattcc gaaggaaaaa ttgtccatct    1860
tgtcgtcttc ggaaatgtta tgaagcaggg atgactctgg gagcccggaa gctgaagaaa    1920
cttggtaatc tgaaactaca ggaggaagga gaggcttcca gcaccaccag ccccactgag    1980
gagacaaccc agaagctgac agtgtcacac attgaaggct atgaatgtca gcccatcttt    2040
ctgaatgtcc tggaagccat tgagccaggt gtagtgtgtg ctggacacga caacaaccag    2100
cccgactcct ttgcagcctt gctctctagc ctcaatgaac tgggagagag acagcttgta    2160
cacgtggtca agtgggccaa ggccttgcct gattgcgaga gagctgcatc agttcacttt    2220
tgacctgcta atcaagtcac acatggtgag cgtggacttt ccggaaatga tggcagagat    2280
catctctgtg caagtgccca agatcctttc tgggaaagtc aagcccatct atttccacac    2340
ccagtgaagc attggaaacc ctatttcccc accccagctc atgccccctt tcagatgtct    2400
tctgcctgtt ataactctgc actactcctc tgcagtgcct tg                       2442
```

<210> SEQ ID NO 5  
<211> LENGTH: 645  
<212> TYPE: PRT  
<213> ORGANISM: Homo sapiens

<400> SEQUENCE: 5

Met Glu Val Gln Leu Gly Leu Gly Arg Val Tyr Pro Arg Pro Pro Ser  
 1               5                  10                  15

Lys Thr Tyr Arg Gly Ala Phe Gln Asn Leu Phe Gln Ser Val Arg Glu  
             20                  25                  30

Val Ile Gln Asn Pro Gly Pro Arg His Pro Glu Ala Ala Ser Ala Ala  
         35                  40                  45

Pro Pro Gly Ala Ser Leu Leu Leu Gln Gln Gln Gln Gln Gln Gln Gln  
     50                  55                  60

Gln Gln Gln Gln Gln Gln Gln Gln Gln Gln Gln Gln Gln Gln Gln Gln  
 65                  70                  75                  80

Gln Gln Gln Gln Gln Glu Thr Ser Pro Arg Gln Gln Gln Gln Gln Gln  
                 85                  90                  95

Gly Glu Asp Gly Ser Pro Gln Ala His Arg Arg Gly Pro Thr Gly Tyr  
            100                 105                 110

```
Leu Val Leu Asp Glu Glu Gln Gln Pro Ser Gln Pro Gln Ser Ala Leu
            115                 120                 125

Glu Cys His Pro Glu Arg Gly Cys Val Pro Glu Pro Gly Ala Ala Val
            130                 135                 140

Ala Ala Ser Lys Gly Leu Pro Gln Gln Leu Pro Ala Pro Pro Asp Glu
145                 150                 155                 160

Asp Asp Ser Ala Ala Pro Ser Thr Leu Ser Leu Leu Gly Pro Thr Phe
                165                 170                 175

Pro Gly Leu Ser Ser Cys Ser Ala Asp Leu Lys Asp Ile Leu Ser Glu
            180                 185                 190

Ala Ser Thr Met Gln Leu Leu Gln Gln Gln Gln Glu Ala Val Ser
            195                 200                 205

Glu Gly Ser Ser Ser Gly Arg Ala Arg Glu Ala Ser Gly Ala Pro Thr
            210                 215                 220

Ser Ser Lys Asp Asn Tyr Leu Gly Gly Thr Ser Thr Ile Ser Asp Asn
225                 230                 235                 240

Ala Lys Glu Leu Cys Lys Ala Val Ser Val Ser Met Gly Leu Gly Val
                245                 250                 255

Glu Ala Leu Glu His Leu Ser Pro Gly Glu Gln Leu Arg Gly Asp Cys
            260                 265                 270

Met Tyr Ala Pro Leu Leu Gly Val Pro Pro Ala Val Arg Pro Thr Pro
            275                 280                 285

Cys Ala Pro Leu Ala Glu Cys Lys Gly Ser Leu Leu Asp Asp Ser Ala
            290                 295                 300

Gly Lys Ser Thr Glu Asp Thr Ala Glu Tyr Ser Pro Phe Lys Gly Gly
305                 310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
            340                 345                 350

Tyr Lys Ser Gly Ala Leu Asp Glu Ala Ala Ala Tyr Gln Ser Arg Asp
            355                 360                 365

Tyr Tyr Asn Phe Pro Leu Ala Leu Ala Gly Pro Pro Pro Pro Pro Pro
            370                 375                 380

Pro Pro His Pro His Ala Arg Ile Lys Leu Glu Asn Pro Leu Asp Tyr
385                 390                 395                 400

Gly Ser Ala Trp Ala Ala Ala Ala Gln Cys Arg Tyr Gly Asp Leu
                405                 410                 415

Ala Ser Leu His Gly Ala Gly Ala Ala Gly Pro Gly Ser Gly Ser Pro
            420                 425                 430

Ser Ala Ala Ala Ser Ser Ser Trp His Thr Leu Phe Thr Ala Glu Glu
            435                 440                 445

Gly Gln Leu Tyr Gly Pro Cys Gly Gly Gly Gly Gly Gly Gly Gly Gly
            450                 455                 460

Gly Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
            500                 505                 510

Val Pro Tyr Pro Ser Pro Thr Cys Val Lys Ser Glu Met Gly Pro Trp
            515                 520                 525
```

```
Met Asp Ser Tyr Ser Gly Pro Tyr Gly Asp Met Arg Leu Glu Thr Ala
        530                 535                 540

Arg Asp His Val Leu Pro Ile Asp Tyr Tyr Phe Pro Pro Gln Lys Thr
545                 550                 555                 560

Cys Leu Ile Cys Gly Asp Glu Ala Ser Gly Cys His Tyr Gly Ala Leu
                565                 570                 575

Thr Cys Gly Ser Cys Lys Val Phe Phe Lys Arg Ala Ala Glu Gly Lys
                580                 585                 590

Gln Lys Tyr Leu Cys Ala Ser Arg Asn Asp Cys Thr Ile Asp Lys Phe
            595                 600                 605

Arg Arg Lys Asn Cys Pro Ser Cys Arg Leu Arg Lys Cys Tyr Glu Ala
        610                 615                 620

Gly Met Thr Leu Gly Glu Lys Phe Arg Val Gly Asn Cys Lys His Leu
625                 630                 635                 640

Lys Met Thr Arg Pro
                645

<210> SEQ ID NO 6
<211> LENGTH: 3641
<212> TYPE: DNA
<213> ORGANISM: Homo sapiens

<400> SEQUENCE: 6
gacactgaat ttggaaggtg gaggattttg ttttttttctt ttaagatctg ggcatctttt      60
gaatctaccc ttcaagtatt aagagacaga ctgtgagcct agcagggcag atcttgtcca     120
ccgtgtgtct tcttctgcac gagactttga ggctgtcaga gcgcttttttg cgtggttgct    180 cccgcaagtt tccttctctg gagcttcccg caggtgggca gctagctgca gcgactaccg     240
catcatcaca gcctgttgaa ctcttctgag caagagaagg ggaggcgggg taagggaagt     300
aggtggaaga ttcagccaag ctcaaggatg gaagtgcagt tagggctggg aagggtctac     360
cctcggccgc cgtccaagac ctaccgagga gctttccaga atctgttcca gagcgtgcgc     420
gaagtgatcc agaacccggg ccccaggcac ccagaggccg cgagcgcagc acctcccggc     480 gccagttttgc tgctgcagca gcagcagcag cagcagcagc agcagcagca gcagcagcag     540
cagcagcagc agcagcagca gcagcagcag cagcagcagc aagagactag ccccaggcag     600
cagcagcagc agcagggtga ggatggttct ccccaagccc atcgtagagg ccccacaggc     660
tacctggtcc tggatgagga acagcaacct tcacagccgc agtcggccct ggagtgccac     720
cccgagagag gttgcgtccc agagcctgga gccgccgtgg ccgccagcaa ggggctgccg     780
cagcagctgc agcagcctcc ggacgaggat gactcagctg ccccatccac gttgtccctg     840
ctgggcccca cttttcccgg cttaagcagc tgctccgctg accttaaaga catcctgagc     900
gaggccagca ccatgcaact ccttcagcaa cagcagcagg aagcagtatc cgaaggcagc     960
agcagcggga gcgagggga ggcctcgggg gctcccactt cctccaagga caattactta    1020
gggggcactt cgaccatttc tgacaacgcc aaggagttgt gtaaggcagt gtcggtgtcc    1080
atgggcctgg gtgtggaggc gttggagcat ctgagtccag ggaacagct tcggggggat    1140 tgcatgtacg ccccactttt gggagttcca cccgctgtgc gtcccactcc ttgtgcccca    1200
ttggccgaat gcaaaggttc tctgctagac gacagcgcag gcaagagcac tgaagatact    1260
gctgagtatt ccccttttcaa ggaggttac accaaagggc tagaaggcga gagcctaggc    1320
tgctctggca gcgctgcagc agggagctcc gggacacttg aactgccgtc tacctgtct    1380 ctctacaagt ccggagcact ggacgaggca gctgcgtacc agagtcgcga ctactacaac    1440
```

-continued

```
tttccactgg ctctggccgg accgccgccc cctccgccgc ctccccatcc ccacgctcgc    1500
atcaagctgg agaacccgct ggactacggc agcgcctggg cggctgcggc ggcgcagtgc    1560
cgctatgggg acctggcgag cctgcatggc gcgggtgcag cgggacccgg ttctgggtca    1620
ccctcagccg ccgcttcctc atcctggcac actctcttca cagccgaaga aggccagttg    1680
tatggaccgt gtggtggtgg tgggggtggt ggcggcggcg gcggcggcgg cggcggcggc    1740
ggcggcggcg aggcgggagc tgtagccccc tacggctaca ctcggccccc tcagggctg     1800 gcgggccagg aaagcgactt caccgcacct gatgtgtggt accctggcgg catggtgagc    1860
agagtgccct atcccagtcc cacttgtgtc aaaagcgaaa tgggcccctg gatggatagc    1920
tactccggac cttacgggga catgcgtttg gagactgcca gggaccatgt tttgcccatt    1980
gactattact ttccaccccca gaagacctgc ctgatctgtg gagatgaagc ttctgggtgt    2040
cactatggag ctctcacatg tggaagctgc aaggtcttct tcaaaagagc cgctgaaggg    2100
aaacagaagt acctgcgcg cagcagaaat gattgcacta ttgataaatt ccgaaggaaa     2160
aattgtccat cttgtcgtct tcggaaatgt tatgaagcag ggatgactct gggagaaaaa    2220 ttccggggttg gcaattgcaa gcatctcaaa atgaccagac cctgaagaaa ggctgacttg    2280
cctcattcaa aatgagggct ctagagggct ctagtggata gtctggagaa acctggcgtc    2340
tgaggcttag gagcttaggt ttttgctcct caacacagac tttgacgttg gggtggggg    2400 ctactctctt gattgctgac tccctccagc gggaccaata gtgttttcct acctcacagg    2460
gatgttgtga ggacgggctg tagaagtaat agtggttacc actcatgtag ttgtgagtat    2520
catgattatt gtttcctgta atgtggcttg gcattggcaa agtgcttttt gattgttctt    2580
gatcacatat gatgggggcc aggcactgac tcaggcggat gcagtgaagc tctggctcag    2640
tcgcttgctt ttcgtggtgt gctgccagga agaaactttg ctgatgggac tcaaggtgtc    2700
accttggaca agaagcaact gtgtctgtct gaggttcctg tggccatctt tatttgtgta    2760
ttaggcaatt cgtatttccc ccttaggttc tagccttctg gatcccagcc agtgacctag    2820
atcttagcct caggccctgt cactgagctg aaggtagtag ctgatccaca gaagttcagt    2880
aaacaaggac cagatttctg cttctccagg agaagaagcc agccaacccc tctcttcaaa    2940
cacactgaga gactacagtc cgactttccc tcttacatct agccttactg tagccacact    3000
ccttgattgc tctctcacat cacatgcttc tcttcatcag ttgtaagcct ctcattcttc    3060
tcccaagcca gactcaaata ttgtattgat gtcaaagaag aatcacttag agtttggaat    3120
atcttgttct ctctctgctc catagcttcc atattgacac cagtttcttt ctagtggaga    3180
agtggagtct gtgaagccag ggaaacacac atgtgagagt cagaaggact ctccctgact    3240
tgcctggggc ctgtctttcc caccttctcc agtctgtcta acacacaca cacacacaca    3300 cacacacaca cacacacaca cacgctctc ctctctctct ccccccccaa cacacacaca    3360
ctctctctct cacacacaca cacatacaca cacacttctt tctctttccc ctgactcagc    3420
aacattctgg agaaaagcca aggaaggact tcaggagggg agtttccccc ttctcagggc    3480
agaattttaa tctccagacc aacaagaagt tccctaatgt ggattgaaag gctaatgagg    3540
tttattttta actactttct atttgtttga atgttgcata tttctactag tgaaatttc     3600 ccttaataaa gccattaata cacccaaaaa aaaaaaaaaa a                        3641
```

<210> SEQ ID NO 7
<211> LENGTH: 20
<212> TYPE: DNA

<213> ORGANISM: Homo sapiens

<400> SEQUENCE: 7
catcagttcg cttttgacct                                              20

<210> SEQ ID NO 8
<211> LENGTH: 20
<212> TYPE: DNA
<213> ORGANISM: Homo sapiens

<400> SEQUENCE: 8
catcagttca cttttgacct                                              20

<210> SEQ ID NO 9
<211> LENGTH: 20
<212> TYPE: DNA
<213> ORGANISM: Homo sapiens

<400> SEQUENCE: 9
catcagttcg cttttgacct                                              20

<210> SEQ ID NO 10
<211> LENGTH: 18
<212> TYPE: DNA
<213> ORGANISM: Homo sapiens

<400> SEQUENCE: 10
ccttgcctga ttgcgaga                                                18

<210> SEQ ID NO 11
<211> LENGTH: 23
<212> TYPE: DNA
<213> ORGANISM: Homo sapiens

<400> SEQUENCE: 11
ccttgctctc tagcctcaat gaa                                          23

<210> SEQ ID NO 12
<211> LENGTH: 26
<212> TYPE: DNA
<213> ORGANISM: Homo sapiens

<400> SEQUENCE: 12
cttgattagc aggtcaaaag tgaact                                       26

<210> SEQ ID NO 13

<400> SEQUENCE: 13

000

<210> SEQ ID NO 14
<211> LENGTH: 39
<212> TYPE: DNA
<213> ORGANISM: Artificial Sequence
<220> FEATURE:
<223> OTHER INFORMATION: A synthetic primer

<400> SEQUENCE: 14
cgcacgatat cgccaccatg ttggagactg ccagggacc                         39

<210> SEQ ID NO 15
<211> LENGTH: 30
<212> TYPE: DNA

```
<213> ORGANISM: Artificial Sequence
<220> FEATURE:
<223> OTHER INFORMATION: A synthetic primer

<400> SEQUENCE: 15
cgcacggatc caggcaaggc cttggcccac                                        30

<210> SEQ ID NO 16
<211> LENGTH: 41
<212> TYPE: DNA
<213> ORGANISM: Artificial Sequence
<220> FEATURE:
<223> OTHER INFORMATION: A synthetic primer

<400> SEQUENCE: 16
cgcacgatat cgccaccatg ggcttccgca acttacacgt g                           41

<210> SEQ ID NO 17
<211> LENGTH: 32
<212> TYPE: DNA
<213> ORGANISM: Artificial Sequence
<220> FEATURE:
<223> OTHER INFORMATION: A synthetic primer

<400> SEQUENCE: 17
cgcacggatc cctgggtgtg gaaatagatg gg                                     32
```